United States Patent
Wittwer et al.

(10) Patent No.: US 7,273,749 B1
(45) Date of Patent: Sep. 25, 2007

(54) CONTAINER FOR CARRYING OUT AND MONITORING BIOLOGICAL PROCESSES

(75) Inventors: Carl T. Wittwer, Salt Lake City, UT (US); Kirk M. Ririe, Idaho Falls, ID (US)

(73) Assignee: University of Utah Research Foundation, Salt Lake City, UT (US)

( * ) Notice: Subject to any disclaimer, the term of this patent is extended or adjusted under 35 U.S.C. 154(b) by 801 days.

(21) Appl. No.: 09/631,339

(22) Filed: Aug. 3, 2000

Related U.S. Application Data

(60) Division of application No. 08/869,275, filed on Jun. 4, 1997, now Pat. No. 7,081,226, which is a continuation-in-part of application No. 08/658,993, filed on Jun. 4, 1996, now abandoned, which is a continuation-in-part of application No. 08/537,612, filed on Oct. 2, 1995, now abandoned, which is a continuation-in-part of application No. 08/179,969, filed on Jan. 10, 1994, now Pat. No. 5,455,175, and a continuation-in-part of application No. 07/815,966, filed on Jan. 2, 1992, now abandoned, which is a continuation-in-part of application No. 07/534,029, filed on Jun. 4, 1990, now abandoned.

(51) Int. Cl.
*C12M 1/34* (2006.01)

(52) U.S. Cl. ............... 435/287.2; 435/288.2; 435/288.7; 435/303.1; 435/808; 422/100; 422/102

(58) Field of Classification Search ............ 435/288.1, 435/288.2, 287.2, 288.7, 304.1–304.3, 307.1, 435/303.1; 422/72, 73, 100, 102, 914, 918, 422/923, 924; 356/246; 73/864.01, 864.02
See application file for complete search history.

(56) References Cited

U.S. PATENT DOCUMENTS

| 1,006,767 A | 10/1911 | Mauger |
| 1,456,005 A | 5/1923 | Harris |
| 2,379,474 A | 7/1945 | Bramson |

(Continued)

FOREIGN PATENT DOCUMENTS

| AU | 528259 | 4/1983 |

(Continued)

OTHER PUBLICATIONS

Barnes, W.M., "PCR Amplification of up to 35-kb DNA with High Fidelity and High Yield from λ Bacteriophage Templates," Proc. Natl. Acad. Sci. USA, vol. 91, pp. 2216-2220 (1994).
Brown, A.B., et al., "Rapid Cycle Amplification For Construction of Competitive Templates," *Genetic Engineering with PCR*, Edited by: Horton, R.M., Horizon Scientific Press, Wymondham, U.K., Chap. 4 (1997).

(Continued)

*Primary Examiner*—William H Beisner
(74) *Attorney, Agent, or Firm*—Barnes & Thornburg LLP

(57) ABSTRACT

A thermal cycling method and device is disclosed. The device comprises a sample chamber whose temperature can be rapidly and accurately modulated over a range of temperatures needed to carry out a number of biological procedures, such as the DNA polymerase chain reaction. Biological samples are placed in containers each comprising a reservoir and a reaction portion, wherein the reaction portion has a small volume. The small volume reaction portion permits the rapid and accurate temperature modulation. With an optically transmissible reaction portion, DNA amplification may be monitored by fluorescence during PCR.

17 Claims, 58 Drawing Sheets

U.S. PATENT DOCUMENTS

| | | | |
|---|---|---|---|
| 3,045,494 A * | 7/1962 | Horace | 73/864.02 |
| 3,219,416 A | 11/1965 | Natelson | |
| 3,518,804 A * | 7/1970 | Gerarde | 53/471 |
| 3,556,659 A * | 1/1971 | Hawes | 356/301 |
| 3,616,264 A | 10/1971 | Ray et al. | |
| 3,718,133 A | 2/1973 | Perry et al. | |
| 3,876,376 A * | 4/1975 | Bauman et al. | 436/63 |
| 3,914,985 A * | 10/1975 | von Behrens | 73/61.72 |
| 4,038,055 A | 7/1977 | Varano et al. | |
| 4,168,017 A | 9/1979 | Anderwald | |
| 4,286,456 A | 9/1981 | Sisti et al. | |
| 4,420,679 A | 12/1983 | Howe | |
| 4,468,423 A | 8/1984 | Hall | |
| 4,481,405 A | 11/1984 | Malick | |
| 4,599,169 A | 7/1986 | Ray | |
| 4,675,300 A | 6/1987 | Zare et al. | |
| 4,683,195 A | 7/1987 | Mullis et al. | |
| 4,683,202 A | 7/1987 | Mullis | |
| 4,684,465 A | 8/1987 | Leaseburge et al. | |
| 4,701,415 A | 10/1987 | Dutton et al. | |
| 4,708,782 A | 11/1987 | Andresen et al. | |
| 4,865,986 A | 9/1989 | Coy et al. | |
| 4,868,103 A | 9/1989 | Stavrianopoulos et al. | |
| 4,889,818 A | 12/1989 | Gelfand et al. | |
| 4,902,624 A | 2/1990 | Columbus et al. | |
| 4,908,112 A | 3/1990 | Pace | |
| 4,965,188 A | 10/1990 | Mullis et al. | |
| 4,981,801 A | 1/1991 | Suzuki et al. | |
| 5,038,852 A | 8/1991 | Johnson et al. | |
| 5,114,551 A | 5/1992 | Hjerten et al. | |
| 5,116,471 A | 5/1992 | Chien et al. | |
| 5,131,998 A | 7/1992 | Jorgenson et al. | |
| 5,137,695 A | 8/1992 | Rusnak et al. | |
| 5,141,621 A | 8/1992 | Zare et al. | |
| 5,142,143 A * | 8/1992 | Fite et al. | 250/288 |
| 5,169,511 A | 12/1992 | Allington et al. | |
| 5,169,521 A | 12/1992 | Oka et al. | |
| 5,173,163 A | 12/1992 | Tehrani | |
| 5,187,084 A | 2/1993 | Hallsby | |
| 5,210,015 A | 5/1993 | Gelfand et al. | |
| 5,234,586 A | 8/1993 | Afeyan et al. | |
| 5,240,577 A | 8/1993 | Jorgenson et al. | |
| 5,241,363 A | 8/1993 | Garner | |
| 5,260,032 A * | 11/1993 | Muller | 422/102 |
| 5,316,913 A | 5/1994 | Butcher et al. | |
| 5,333,675 A | 8/1994 | Mullis et al. | |
| 5,346,672 A | 9/1994 | Stapleton et al. | |
| 5,348,853 A | 9/1994 | Wang et al. | |
| 5,364,790 A | 11/1994 | Atwood et al. | |
| 5,380,489 A | 1/1995 | Sutton et al. | |
| 5,415,839 A | 5/1995 | Zaun et al. | |
| 5,425,921 A | 6/1995 | Coakley et al. | |
| 5,436,134 A | 7/1995 | Haugland et al. | |
| 5,455,175 A | 10/1995 | Wittwer et al. | |
| 5,563,037 A | 10/1996 | Sutherland et al. | |
| 5,565,322 A | 10/1996 | Heller | |
| 5,585,242 A | 12/1996 | Bouma et al. | |
| 5,599,504 A | 2/1997 | Hosoi et al. | |
| 5,785,926 A * | 7/1998 | Seubert et al. | 422/100 |
| 6,144,448 A | 11/2000 | Mitoma | |

FOREIGN PATENT DOCUMENTS

| | | |
|---|---|---|
| DE | 3 808 942 A1 | 9/1989 |
| EP | 0 229 943 A2 | 1/1985 |
| EP | 0 171 140 A2 | 2/1986 |
| EP | 0 211 334 A1 | 2/1987 |
| EP | 0 236 069 A2 | 2/1987 |
| EP | 0 318 255 | 5/1989 |
| EP | 0 404 258 | 12/1990 |
| EP | 0 459 241 A1 | 5/1991 |
| EP | 0 475 760 A2 | 9/1991 |
| EP | 0 488 769 A2 | 11/1991 |
| EP | 0 519 623 A2 | 12/1992 |
| EP | 0 566 751 | 10/1993 |
| EP | 0 580 362 A1 | 1/1994 |
| EP | 0 640 828 A1 | 8/1994 |
| EP | 0 636 413 | 2/1995 |
| EP | 0 643 140 | 3/1995 |
| EP | 0 674 009 | 9/1995 |
| EP | 0 686 699 | 12/1995 |
| FR | 2 122 187 | 8/1972 |
| JP | 6 212 986 | 3/1987 |
| WO | WO89 09437 | 10/1989 |
| WO | WO92 20778 | 11/1992 |
| WO | WO93/20240 | 10/1993 |
| WO | WO94/27137 | 11/1994 |
| WO | WO95 13399 | 5/1995 |
| WO | WO95/21266 | 8/1995 |
| WO | WO95 21382 | 8/1995 |
| WO | WO95 30139 | 11/1995 |
| WO | WO95 32306 | 11/1995 |
| WO | WO96 00901 | 1/1996 |
| WO | WO96 06354 | 2/1996 |

OTHER PUBLICATIONS

Cao, T.M., "A Simple and Inexpensive System to Amplify DNA for PCR," *BioTechniques*, vol. 7, No. 6, pp. 566-567 (1989).

Cardullo, R.A., et al., "Detection of Nucleic Acid Hybridization by Nonradiative Fluorescence Resonance Energy Transfer," Proc. Natl. Acad. Sci. USA, vol. 85, pp. 8790-8794 (1988).

Cotton, R. G. H, "Detection of Single Base Changes in Nucleic Acids", *The Biochemical Journal*, vol. 263, pp. 1-10, Oct. 1, 1989.

Denton, P., et al., "A Low-Cost Air-Driven Cycling Oven," *PCR Protocols: A Guide to Methods and Applications*, Edited by M.A. Innis, et al., Academic Press, Inc., San Diego, Chap. 52, pp. 435-441 (1990).

Findlay, J.B., et al., "Automated Closed-Vessel System for in Vitro Diagnostics Based on Polymerase Chain Reacton," *Clinical Chemistry*, vol. 39, No. 9, pp. 1927-1933 (1993).

Ghosh, S.S., et al., "Real Time Kinetics of Reduction Endonuclease Cleavage Monitored by Fluorescence Resonance Energy Transfer," *Nucleic Acids Research*, vol. 22, No. 15, pp. 3155-3159 (1994).

Goldner, H., "PCR update: New Techniques Multiply Uses," *R & D Magazine*, vol. 36, No. 4, pp. 55 (Mar. 1994).

Graham, A., "A Haystack of Needles: Applying the Polymerase Chain Reaction," *Chemistry and Industry*, No. 18, pp. 718 (Sep. 19, 1994).

Gustafson, C.E., et al., "Effect of Heat Denaturation of Target DNA on the PCR Amplification," *Gene*, vol. 123, pp. 241-244 (1993).

Higuchi, R., et al., "Simultaneous Amplification and Detection of Specific DNA Sequences," *Bio/Technology*, vol. 10, pp. 413-417 (1992).

Higuchi, R., et al., "Kinetic PCR Analysis: Real-time Monitoring of DNA Amplification Reactions," *Bio/Technology*, vol. 11, pp. 1026-1030 (1993).

Hillen, W., et al., "High Resolution Experimental and Theoretical Thermal Denaturation Studies on Small Overlapping Restriction Fragments Containing the *Escherichia coli* Lactose Genetic Control Region," *The Journal of Biological Chemistry*, vol. 256, No. 6, pp. 2761-2766 (1981).

Hiyoshi, M., et al., "Assay of DNA Denaturation by Polymerase Chain Reaction-Driven Fluorescence Resonance Energy Transfer," *Analytical Biochemistry*, vol. 221, pp. 306-311 (1994).

Hoffman, L.M., et al., "Use of a Gas Chromatograph Oven for DNA Amplification by the Polymerase Chain Reaction," *BioTechniques*, vol. 6, No. 10, pp. 932-936 (1988).

Holland, P.M., et al., "Detection of Specific Polymerase Chain Reaction Product by Utilizing the 5'- 3' Exonuclease Activity of *Thermus Aquaticus* DNA Polymerase," Proc. Natl. Acad. Sci. USA, vol. 88, pp. 7276-7280 (1991).

Hopfenbeck, J.A., et al., "Digoxigenin-Labeled Probes Amplified from Genomic DNA Detect T-Cell Gene Rearrangements," American Jouranl of Clincal Pathology, vol. 97, No. 5, pp. 638-644 (1992).

Ishiguro, T., et al., "Homogeneous Quantitative Assay of Hepatitis C Virus RNA by Polymerase Chain Reaction in the Presence of a Fluorescent Intercalater," Analytical Biochemistry, vol. 229, pp. 207-213 (1995).

Kang, J., et al., "Exact Quantification of DNA-RNA Copy Numbers by PCR-TGGE," PCR Strategies, Academic Press, Inc., Chap 15, pp. 189-198 (1995).

Ke, S., et al., "Influence of Nearest Neighbor Sequence on the Stability of Base Pair Mismatches in Long DNA: Determined by Temperature-Gradient Gel Electrophoresis," Nucleic Acids Research, vol. 21, No. 22, pp. 5137-5143 (1993).

Lee, L.G., et al., "Allelic Discrimination by Nick-Translation PCR with Flurogenic Probes," Nucleic Acids Research, vol. 21, No. 16, pp. 3761-3766 (1993).

Linz, U., "Thermocycler Temperature Variation Invalidates PCR Results," Biotechniques, vol. 9, No. 3, pp. 286-290 (1990).

Livak, K.J., et al., "Oligonucleotides with Fluorescent Dyes at Opposite Ends Provide a Quenched Probe System Useful for Detecting PCR Products and Nucleic Acid Hybridization," PCR Methods and Application, vol. 4, pp. 357-362 (1995).

Livak, K.J., "Quantitation of DNA-RNA Using Real-Time PCR Detection," Perkin-Elmer Applied Biosystems Report (1996).

Morrison, L.E., "Detection of Energy Transfer and Fluorescence Quenching," Nonisotopic DNA Probe Techniques, Edited by: Larry J. Kricka, Academic Press, Inc., San Diego, Chap. 13, pp. 311-352 (1992).

Morrison, L.E., et al., "Sensitive Fluorescence-Based Thermodynamic and Kinetic Measurements of DNA Hybridization in Solution," Biochemistry, vol. 32, pp. 3095-3104 (1993).

Nilsson, P., et al., "Real-Time Monitoring of DNA manipulations Using Biosensor Technology," Analytic Biochemistry, vol. 224, pp. 400-408 (1995).

Oste, C.C., "PCR Instrumentation: Where Do We Stand?," The Polymerase Chain Reaction, Edited by Mullis, et al., Birkhauser, Boston, Chap. 14 (1994).

Perry, R.H., et al., "Heat Transmission by Radiation," Chemical Engineers' Handbook, 5th ed., McGraw Hill Book Co., York, Chap. 10, pp. 45-56, no date provided.

Ririe, K.M., et al., "Product Differentiation by Analysis of DNA Melting Curves during the Polymerase Chain Reaction," Analytical Biochemistry, vol. 254, pp. 154-160 (1997).

Segal, G.H., et al., "Identification of Monoclonal B-cell Populations by Rapid Cycle Polymerase Chain Reaction," The American Journal of Pathology, vol. 141, No. 6, pp. 1291-1297 (1992).

Service, R.E., "The Incredible Shrinking Laboratory: Microchips Allow Miniaturization of Analytical Laboratories," Science, vol 268, No. 5207, p. 26 (Apr. 7, 1995).

Stimpson, D.I., "Real-time Detection of DNA Hybridization and Melting on Oligonucleotide Arrays by Using Optical Wave Guides," Proc. Natl. Acad. Sci. USA, vol. 92, pp. 6379-6383 (1995).

Swerdlow, H., et al., "Fully Automated DNA Reaction and Analysis in a Fluidic Capillary Instrument," Anal. Chem., vol. 69, pp. 848-855 (1997).

Tombler, E.R., et al., "Spectrofluorometric Assay for Hybridization of Oligodeoxynucleotides Using Ethidium Dimer," BioTechniques, vol. 15, No. 6, pp. 1060-1064 (1993).

Tyagi, S., et al., "Molecular Beacons: Probes that Fluoresce upon Hybridization," Nature Biotechnology, vol. 14, pp. 303-308 (1996).

Weis, J.H., et al., "Detection of Rare mRNAs via Quantitative RT-PCR," Trends in Genetics, vol. 8, No. 8, pp. 263-264 (1992).

Wilding, et al., "PCR in Silicon Microstructure," Clinical Chemistry, vol. 40, No. 9, pp. 1815-1818, (1994).

Willard, H.H., et al., "Gas Chromatography," Instrumental Methods of Analysis, 6th cd, Wedsworth Publishing Co., Belmont, CA, Chap. 16, pp. 454, no date provided.

Wittwer, C.T., et al., "Minimizing the Time Required for DNA Amplification by Efficient Heat Transfer to Small Samples," Analytical Biochemistry, vol. 186, pp. 328-331 (1990).

Wittwer, C.T., et al., "Automated Polymerase Chain Reaction in Capillary Tubes with Hot Air," Nucleic Acids Research, vol. 17, No. 11, pp. 4353-4357 (1989).

Wittwer, C.T., et al., "Rapid Cycle DNA Amlification Time and Temperature Optimization," BioTechniques, vol. 10, No. 1, pp. 76-83 (1991).

Wittwer, C.T., et al., "Rapid Cycle Allele-Specific Amplification: Studies with the Cystic Fibrosis $\Delta F_{508}$ Locus," Clinical Chemistry, vol. 39, No. 5, pp. 804-809 (1993).

Wittwer, C.T., et al., "Rapid Cycle DNA Amplification," The Polymerase Chain Reaction, Edited by: Mullis, et al., Birkhauser, Boston Chap. 15 (1994).

Wittwer, C.T., et al.,"Continuous Fluorescence Monitoring of Rapid Cycle DNA Aplification," Bio Techniques, vol. 22, pp. 130-138 (1997).

Wittwer, C.T., et al., "The LightCycler: A Microvolume Multisample Fluorimeter with Rapid Temperature Control," Bio Techniques, vol. 22, pp. 176-181 (1997).

Wittwer, C. T., et al., "Fluorescence Monitoring of Rapid Cycle PCR For Quantification," Gene Quantification, Edited by: Ferre, F., Birkhauser, Boston (1998).

Yguerabide, J., et al., "Quantitative Fluorescence Method for Continuous Measurement of DNA Hybridization Kinetics Using a Fluorescent Intercalator," Analytical Biochemistry, vol. 228, pp. 208-220 (1995).

Biotherm Corporation Advertisement, BioOven (1991).

Ericomp Advertisement, Twinblock System (1991).

Techne Adertisement, PHC-l Dri-Block (1988).

Hybaid Advertisement, Hybaid Heating and Cooling Block (1988).

Eppendorf Advertisement, Eppendorf MicroCycler (1988).

COY Advertisement, Tempcycler Model 50 Microtube Incubator (1991).

Idaho Technology Advertisement and Specification Sheets for 1605 Product (1991).

Perkin-Elmer Advertisement, ABI Prism 7700 Sequence Detection System (1991).

Clark, et al., "Cassettes Simplify Small-sample Dialysis," R & D Magazine, p. 31, Sep. 1995.

"Let the Microchip Fall Where Diagnostics Lies: Implications: A Diagnostic Revolution?," Genesis Report-Dx, vol. 4, No. 3. 1994.

"Let the Microchip Fall Where Diagnostics Lies: Implications: Affymetrix: DNA on a Chip," Genesis Report-Dx, vol. 4, No. 3 (1994).

"PCR Detection Blows Cover on Lyme Disease, Q Fever," Biotechnology Newswatch, vol. 10, No. 1 (Jan. 1, 1990).

Schoffner et al., "Chip PCR. I. Surface passivation of microfabricated silicon-glass chips or PCR", Nucleic Acids Research, vol. 24, No. 2, pp. 375-379, 1996.

Cheng et al., "Chip PCR II. Investigation of different PCR amplification systems in microfabricated silicon-glass chips", Nucleic Acids Research, vol. 24, No. 2, pp. 380-385, 1996.

Operation manual for HP-5880A Gas Chromatograph, no date provided.

Operation manual for the MIC 6000, no date provided.

\* cited by examiner

Effect of Annealing Time on Product Yield and Background Amplification

| 92 to 55 °C Ramp Time (sec) | Time at 55 °C (sec) |
|---|---|
| 9 | <1 |
| 25 | <1 |
| 25 | 5 |
| 25 | 10 |
| 25 | 20 |
| 25 | 40 |
| 25 | 80 |
|  | PhiX174 RF Hae III Digest |

Effect of Denaturation Time on Product Yield

| Time at 92-94 °C (sec) |
|---|
| <1 |
| 2 |
| 4 |
| 8 |
| 16 |
| 32 |
| 64 |
| PhiX174 RF Hae III Digest |

Initial Template Copies

- ♦ $10^9$
- □ $10^8$
- ▲ $10^7$
- × $10^6$
- ◇ $10^5$
- ● $10^4$
- + $10^3$
- - $10^2$
- – $10$
- ■ $1$
- △ $0$

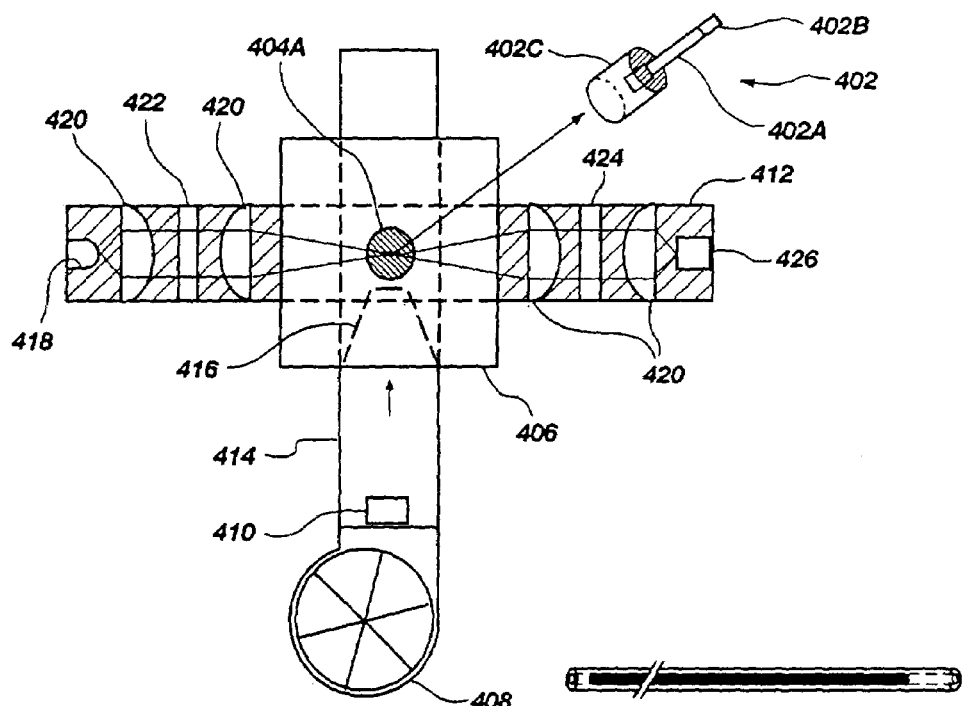
Fig. 19
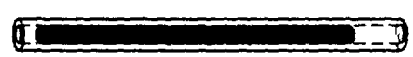
Fig. 19A
Fig. 19B
Fig. 19C
Fig. 19D
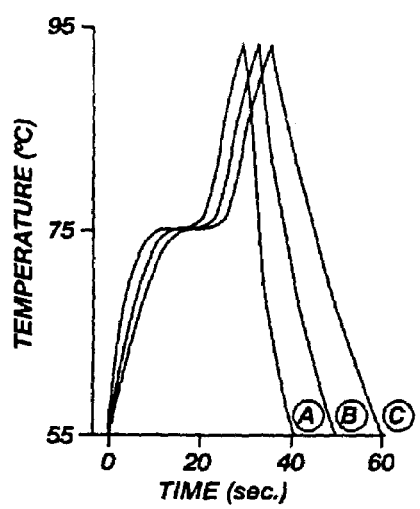
Fig. 19E Load Sample  Centrifuge  Seal  Cycle

CONTAINER FOR CARRYING OUT AND MONITORING BIOLOGICAL PROCESSES

RELATED APPLICATIONS

This is a divisional of U.S. patent application Ser. No. 08/869,275, filed Jun. 4, 1997 now U.S. Pat. No. 7,081,226, entitled System And Method For Monitoring PCR Processes which is a continuation-in-part of U.S. patent application Ser. No. 08/658,993, filed Jun. 4, 1996 (now abandoned) entitled System And Method For Monitoring PCR Processes which is a continuation-in-part of U.S. patent application Ser. No. 08/537,612, filed Oct. 2, 1995 now abandoned, entitled Method For Rapid Thermal Cycling of Biological Samples which is a continuation-in-part of U.S. patent application Ser. No. 08/179,969, filed Jan. 10, 1994 (now U.S. Pat. No. 5,455,175), entitled Rapid Thermal Cycling Device which is a continuation-in-part of U.S. patent application Ser. No. 07/815,966 filed Jan. 2, 1992 (now abandoned) entitled Rapid Thermal Cycling Device which is a continuation-in-part of U.S. patent application Ser. No. 07/534,029 filed Jun. 4, 1990 (now abandoned), entitled Automated Polymerase Chain Reaction Device, each of the above-identified applications are now each individually incorporated herein by reference in their entireties.

The U.S. application filed in the U.S. Patent and Trademark on Jun. 4, 1997 entitled Monitoring Hybridization During PCR as Ser. No. 08/869,276 now U.S. Pat. No. 6,174,670 and naming Carl T. Wittwer, Kirk M. Ririe, and Randy P. Rasmussen as inventors is hereby incorporated by reference in its entirety.

BACKGROUND

1. The Field of the Invention

This invention relates generally to apparatus which are used to carry out biological processes, such as the polymerase chain reaction. More specifically, the present invention relates to apparatus and methods which carry out thermal cycling and monitoring of various biological reactions, such as the polymerase chain reaction.

2. The Background Art

In numerous areas of industry, technology, and research there is a need to reliably and reproducibly subject samples to thermal cycling. The need to subject a sample to repeated thermal cycles is particularly acute in biotechnology applications. In the biotechnology field, it is often desirable to repeatedly heat and cool small samples of materials over a short period of time. One such biological process that is regularly carried out is cyclic DNA amplification.

Cyclic DNA amplification, using a thermostable DNA polymerase, allows automated amplification of primer specific DNA, widely known as the "polymerase chain reaction" or "PCR." Automation of this process requires controlled and precise thermal cycling of reaction mixtures usually contained in a plurality of containers. In the past, the container of preference has been a standard, plastic microfuge tube.

Commercial programmable metal heat blocks have been used in the past to effect the temperature cycling of samples in microfuge tubes through the desired temperature versus time profile. However, the inability to quickly and accurately adjust the temperature of the heat blocks through a large temperature range over a short time period, has rendered the use of heat block type devices undesirable as a heat control system when carrying out processes such as the polymerase chain reaction.

Moreover, the microfuge tubes which are generally used have disadvantages. The material of the microfuge tubes, their wall thickness, and the geometry of microfuge tubes is a hindrance to rapid heating and cooling of the sample contained therein. The plastic material and the thickness of the wall of microfuge tubes act as an insulator between the sample contained therein and the surrounding medium thus hindering transfer of thermal energy. Also, the geometry of the microfuge tube presents a small surface area to whatever medium is being used to transfer thermal energy. The continued use of microfuge tubes in the art, with their suboptimal geometry, indicates that the benefits of improved thermal transfer (which come by increasing the surface area of a sample container for a sample of constant volume) has heretofore not been recognized.

Furthermore, devices using water baths with fluidic switching, (or mechanical transfer) have also been used as a thermal cycler for the polymerase chain reaction. Although water baths have been used in cycling a polymerase chain reaction mixture through a desired temperature versus time profile necessary for the reaction to take place, the high thermal mass of the water (and the low thermal conductivity of plastic microfuge tubes), has been significantly limiting as far as performance of the apparatus and the specificity of the reaction are concerned.

Devices using water baths are limited in their performance. This is because the water's thermal mass significantly restricts the maximum temperature versus time gradient which can be achieved thereby. Also, the water bath apparatus has been found to be very cumbersome due to the size and number of water carrying hoses and external temperature controlling devices for the water. Further the need for excessive periodic maintenance and inspection of the water fittings for the purpose of detecting leaks in a water bath apparatus is tedious and time consuming. Finally, it is difficult with the water bath apparatus to control the temperature in the sample tubes with the desired accuracy.

U.S. Pat. No. 3,616,264 to Ray shows a thermal forced air apparatus for cycling air to heat or cool biological samples to a constant temperature. Although the Ray device is somewhat effective in maintaining a constant temperature within an air chamber, it does not address the need for rapidly adjusting the temperature in a cyclical manner according to a temperature versus time profile such as is required for biological procedures such as the polymerase chain reaction.

U.S. Pat. No. 4,420,679 to Howe and U.S. Pat. No. 4,286,456 to Sisti et al. both disclose gas chromatographic ovens. The devices disclosed in the Howe and Sisti et al. patents are suited for carrying out gas chromatography procedures but do not provide thermal cycling which is substantially any more rapid than that provided by any of the earlier described devices. Rapid thermal cycling is useful for carrying out many procedures. Devices such as those described in the Howe and Sisti et al. patents are not suitable for efficiently and rapidly carrying out such reactions.

In particular, the polymerase chain reaction (PCR) is a fundamental DNA amplification technique essential to modern molecular biology. Despite its usefulness and popularity, the current understanding of PCR is not highly advanced. Amplifications must be optimized by trial and error and protocols are often followed blindly. The limited understanding of PCR found in the art is a good example of how those skilled in the art are content to utilize a powerful technique without reflection or comprehension.

Biological processes such as PCR require temperature cycling of the sample. Not only does the prior art, as explained above, carry out temperature cycling slowly, the prior art also ignores the underlying principles which allow PCR to work and could be used to make PCR even more useful. Thus, it would be a great advance in the art to provide methods and apparatus which are particularly adaptable for rapidly carrying out PCR and analyzing the reaction which is taking place, particularly if such reaction is analyzed as it is taking place, that is, in real time.

BRIEF SUMMARY AND OBJECTS OF THE INVENTION

In view of the above described state of the art, the present invention seeks to realize the following objects and advantages.

It is an object of the present invention to provide an apparatus for accurately controlling the temperature of biological samples.

It is a further object of the present invention to provide a thermal cycling apparatus for quickly and accurately varying the temperature of biological samples according to a predetermined temperature versus time profile.

It is another object of the present invention to provide an apparatus suitable for subjecting a number of different biological samples to rapid thermal cycling.

It is also an object of the present invention to provide a thermal cycling apparatus having a thermal transfer medium of low thermal mass which can effectively subject samples to a large temperature gradient over a very short period of time.

It is a further object of the present invention to provide an apparatus which can subject a biological sample to rapid thermal cycling using air as a thermal transfer medium.

It is another object of the present invention to provide a thermal cycling apparatus which will heat samples located in a fluid chamber therein, by means of an internal heater, and will subsequently cool the samples by moving ambient fluid into the chamber, at the proper time in the thermal cycle, to cool the samples.

It is an object of the present invention to provide a system and method for performing PCR rapidly and for simultaneously monitoring the reaction.

It is another object of the present invention to provide a system and method for performing PCR rapidly and also continuously monitoring the reaction while it is ongoing.

It is a further object of the present invention to provide a system and method for performing PCR rapidly while also adjusting the reaction parameters while the reaction is ongoing.

It is another object of the present invention to replace the nucleic acid probes by synthetic nucleic acid analogs or derivatives, e.g., by peptide nucleic acids (PNA), provided that they can also be labeled with fluorescent compounds.

These and other objects and advantages of the invention will become more fully apparent from the description and claims which follow, or may be learned by the practice of the invention.

In accordance with one aspect of the present invention, an apparatus is provided which is particularly suited for subjecting biological samples to rapid thermal cycling in order to carry out one or more of a number of procedures or processes. In one of its preferred forms, the apparatus includes a means for holding a biological sample. In some preferred embodiments, the structure which holds a biological sample, also referred to as a sample chamber, is provided with an insulation means for retaining thermal energy and also a means for heating the interior of the sample chamber.

In some preferred embodiments, an incandescent lamp functions as a means for heating the interior of the sample chamber. In further embodiments, hot or cool air is conveyed into and out of a chamber holding the biological sample. In some preferred embodiments, a thermal insulator is disposed along the interior of the sample chamber and functions to retain the heat generated by the lamp within the sample chamber and serves as an insulation means.

In order to rapidly cool the sample chamber, the preferred apparatus includes a means for forcing air into the sample chamber and a means for dispersing the air forced into the sample chamber. The preferred structures included in some embodiments are a high velocity fan which functions to force air into the sample chamber and a rotating paddle which functions to disperse the air into the chamber. In some embodiments, a means for venting allows the air to escape from the sample chamber taking the unwanted heat with it. The present invention allows heating and cooling of a sample to take place both quickly and uniformly.

In accordance with the method and the apparatus of the present invention, a control structure provides means for operating the system through a desired time versus temperature profile. The present invention is particularly well suited for carrying out automated polymerase chain reaction procedures.

The controller of the present invention allows the biological samples to pass through a predetermined temperature cycle corresponding to the denaturation, annealing and elongation steps in the polymerase chain reaction. In use, the apparatus of the present invention allows rapid optimization of denaturation, annealing, and elongation steps in terms of time and temperature, and shortened time periods (ramp times) between the temperatures at each step.

The present invention particularly decreases the total time required for completion of polymerase chain reaction cycling over prior art thermal cycling devices while at the same time significantly increasing specificity and yield.

In accordance with another aspect of the present invention, the present invention provides methods and apparatus for monitoring of DNA amplification so as to track the progress of such procedures. In particular, the present invention provides methods and apparatus for continuous fluorescence monitoring of the polymerase chain reaction procedure. In preferred embodiments of the present invention, optical components are combined with structures to provide rapid temperature cycling in order to continuously monitor DNA amplification by a variety of different fluorescence techniques. Glass capillary sample containers and composite plastic/glass sample containers allow rapid heat transfer from the preferred thermal transfer medium (allowing 30 amplification cycles in less than 15 minutes when a gas such as air is used as the thermal transfer medium) and simultaneous monitoring of the reaction.

In accordance with another aspect of the present invention, optical techniques are used to monitor the progress of the reaction as the reaction is ongoing. In some preferred embodiments of the invention, fluorescent probes are added to the reaction mixture. The present invention then monitors the fluorescence at least once during a temperature transition, and preferably the fluorescence is acquired two or more times during a temperature transition, either from a single sample or from multiple samples. In some preferred embodiments a rotating carousel is included to sequentially move the samples, one-by-one, to a monitoring location with all of the samples being simultaneously subjected to rapid thermal cycling. Desirably, embodiments of the present invention provide for monitoring of fluorescence once per amplification cycle or monitoring temperature, time, and fluorescence continuously throughout each amplification cycle.

Using the present invention, a 3-dimensional plot of temperature, time, and fluorescence, can be obtained. Fluorescence vs. temperature plots of hybridization probes discriminate between the cumulative, irreversible signal of exonuclease cleavage and the temperature-dependent, reversible hybridization of adjacent probes. Hybridization probes are more useful than hydrolysis probes because the temperature dependence of fluorescence can be followed and used to detect alterations in product sequence, i.e., polymorphisms and mutations. Using dyes that fluoresce in the presence of double stranded DNA, product denaturation, reannealing and extension can be followed within each cycle. The present invention provides apparatus and methods for rapidly carrying out DNA amplification reactions which combines amplification and analysis of the reaction in under fifteen minutes and more preferably in under fifteen minutes and most preferably in under ten minutes.

BRIEF DESCRIPTION OF THE DRAWINGS

In order to better appreciate how the above-recited and other advantages and objects of the invention are obtained, a more particular description of the invention briefly described above will be rendered by reference to specific embodiments thereof which are illustrated in the appended drawings. Understanding that these drawings depict only typical embodiments of the invention and are not therefore to be considered limiting of its scope, the invention will be described and explained with additional specificity and detail through the use of the accompanying drawings in which:

FIG. 19 represents another preferred embodiment of the present invention configured for continuous monitoring of a sample.

FIGS. 19A-19D are representations of different sample container configurations.

FIG. 19E is a chart which shows the effect of the different sample container configurations of FIGS. 19A-D on the temperature response of the sample itself.

FIGS. 21A-D show composite plastic/glass containers into which biological samples are loaded.

DETAILED DESCRIPTION OF THE PREFERRED EMBODIMENTS

Reference will now be made to the drawings wherein like structures will be provided with like reference designations.

Figure 1:
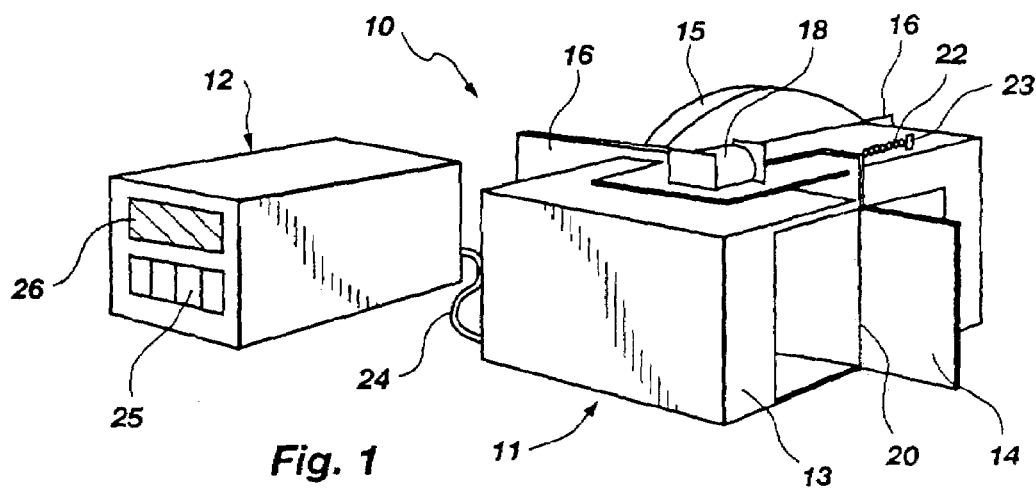
FIG. 1 shows a perspective view of a thermal cycling apparatus adapted for thermal cycling of biological samples and adapted especially for use in cyclic DNA amplification, according to the concepts of the present invention.

As shown in FIG. 1, the one preferred thermal cycling device 10 includes a closed loop fluid (most preferably air) chamber, generally designated at 11, which is adapted to accept samples to be cycled through vent door 14. The closed loop fluid chamber 11 includes a plurality of compartments each of which will be described shortly. The device 10 also includes a controller 12 which can be programmed by means of input keys 25 and display 26 to cause the chamber 11 to be cycled through a series of temperatures over a predetermined period of time. The thermal cycling of chamber 11 can be used to carry out numerous procedures and is particularly suited for amplification of primer specific DNA from samples containing reaction mixtures as will be explained below.

The closed loop fluid chamber 11 is enclosed in a generally box shaped configuration by housing 13. Blower mounting boards 16, if desired, can be located so as to section off a smaller rectangular section of the chamber 11 and function to support and secure a generally cylindrically shaped lower housing 15 thereto. Alternatively, the fan of the blower 28 may be housed integrally within chamber housing 13.

The interior of blower housing 15 contains the blades and shaft of the blower. The blower motor (not shown) is located externally of blower housing 15, and therefore exteriorly of the enclosed chamber 11. In this configuration, the blades and shaft are the only parts of the blower which become exposed to the circulating hot fluid within chamber 11. It would be disadvantageous to mount the motor within the chamber which would subject the motor to temperature variations and also would add the thermal mass of the motor to that which is subject to heating and cooling. The reduction of thermal mass exposed to the fluid in chamber 11 is desirable to the overall performance of the device 10 in its function of subjecting samples placed therein to a desired temperature versus time profiles, using either predetermined profiles or by altering one or more reaction parameters as the reaction continues, as will be more fully explained below.

The blower 28 is a well known type of blower usually identified as an "in line" type blower which preferably employs a propeller type fan, due to its generally low thermal mass, or if desired, a squirrel cage type fan, the fan preferably having a 75 cubic feet per minute minimum capacity.

The solenoid platform 17 has secured thereto a solenoid 18. The solenoid armature 19 is attached to upper end 21 of rod 20 which is rigidly attached to vent door 14 and rotatably attached to housing 13 at points above and below the vent door 14. The rod 20 therefore allows vent door 14 to freely rotate relative to the housing 13 about the rod's longitudinal axis.

A spring 22 is attached at one of its ends to the housing 13 by support post 23. The opposite end of spring 22 is attached to the top end 21 of rod 20 directly adjacent the attachment of solenoid armature 19. The spring 22 is drawn between these two attachment points so as to be in tension. The spring 22 therefore tends to draw top end 21 toward the support post 23, which in turn tends to rotate vent door 14 to its closed position. When solenoid 18 is actuated, armature 19 tends to pull top end 21 of the rod 20 in the direction of the solenoid 18, which is opposite the direction of pull of spring 22, and which tends to open the vent door 14.

Controller, generally designated at 12, is electrically attached to the chamber 11 by means of a transmission cable 24. The cable 24 also supplies power to the blower motor (not shown), and to the heat coil 31. Further, the controller 12 also is connected to thermocouple sensor 35 for receiving signals corresponding to temperature data, and to solenoid 18 for triggering the solenoid armature.

Controller 12 can be any well known type of temperature controller unit which is programmable to control the heat coil 31, vent door 14, and blower so as to achieve predetermined temperatures as a function of time within the chamber 11, and which is also capable of being programmed to actuate a relay output for driving a solenoid at predetermined time periods and chamber temperature levels. A preferred temperature controller 12 for use in the embodiment of FIGS. 1-3 is a Partlow MIC-6000 proportional temperature controller, available through Omega Engineering Inc, of Stanford, Conn., as the Model No. CN8600 process controller.

Figure 2:
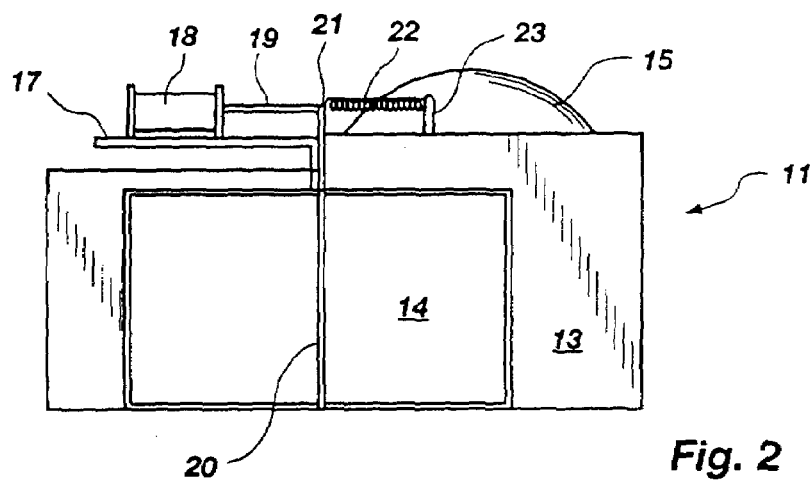
FIG. 2 is a side elevation view of the fluid chamber portion of the apparatus of FIG. 1.
Figure 3:
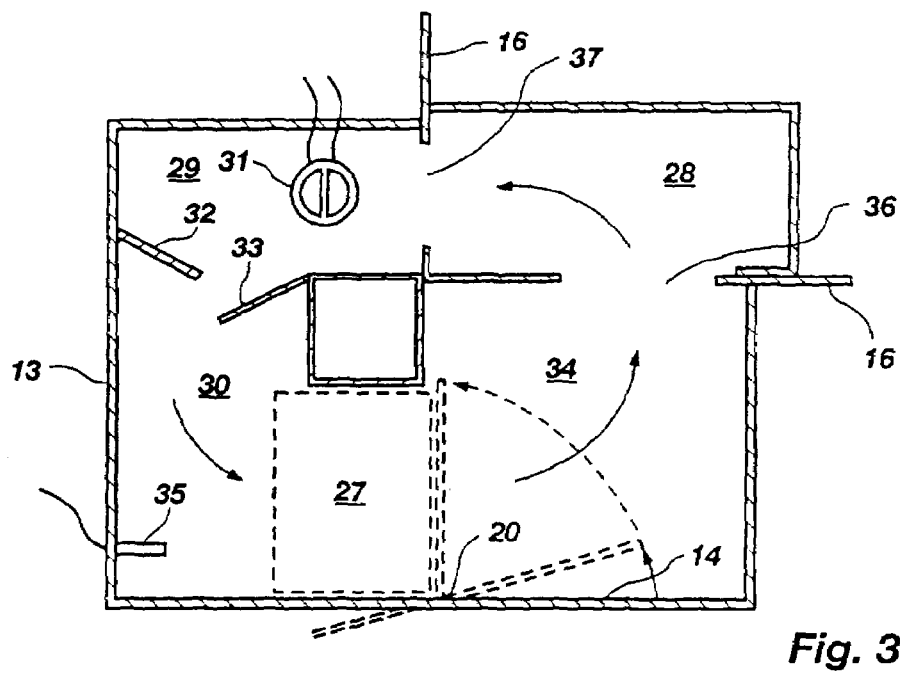
FIG. 3 is an interior plan view of the fluid chamber portion of the apparatus illustrated in FIG. 1.

As shown in FIGS. 2 and 3, the interior of chamber 11 is sectioned off into four main compartments. The blower compartment 28 is formed of the blower housing 15 and the blower mounting plates 16. The entirety of blower compartment 28 is filled with the fan and shaft portions of a blower as has been described above. The blower can be any of a number of well-known designs, as has been described above, and has therefore been omitted from FIG. 3 for purposes of clarity. It is sufficient for the present invention to understand that the fan located in blower compartment 28 draws fluid into the blower compartment 28 through inlet opening 36 and pushes the fluid out of exit opening 37.

It is preferred that the fluid be driven by the blower at a rate of at least 75 cubic feet per minute. It is important however, in regard to the present invention, to realize that the fluid located in chamber 11 only contacts the fan and a portion of the drive shaft of the blower, the blower motor itself being located outside of the blower housing 15 so as to avoid any contact thereof with fluid in the chamber 11. This consideration contributes to the speed of operation of the invention to minimize the material which contacts the fluid inside the chamber 11 so as to minimize the thermal mass of material which must be heated and/or cooled thereby during the cycling process. By minimizing the thermal mass which must be heated or cooled by the fluid, the response time necessary to bring the contents of chamber 11 to a uniform temperature is greatly diminished.

Fluid exiting blower compartment 28 through outlet opening 37 enters heating compartment 29. Fluid passing into heating compartment 29 must pass by heating coils 31. If the heating coils 31 get hotter than the fluid passing into heating compartment 29, the fluid will become heated thereby as it is forced through the compartment. The heating coil is preferably a 1,000 watt (125 VAC) nichrome wire coil wound around a microsupport. However, any heating unit suitable for heating the type of fluid present in the chamber may be used. The particular heating coil of embodiment of FIGS. 1-3 is manufactured by Johnstone Supply, of Portland, Oreg.

The heating coil is activated by an output relay included in the controller 12. The preferred relay is a 25 A, 125 VAC solid state relay manufactured by Omega Engineering Inc. of Stanford, Conn. as Model No. Omega SSR 240 D25.

Fluid passing through heating compartment 29 becomes incident on baffles 32 and 33 before passing into the reaction compartment 30. Baffles 32 and 33 tend to break up any laminar fluid flow and generate turbulence therein to effectively mix the fluid so that it arrives in reaction compartment 30 at an homogenous temperature.

Thermocouple sensor 35 provides an electrical input signal to controller 12 which corresponds to the fluid temperature in the reaction compartment 30. Temperature monitoring during operation of the thermal cycling device 10 is preferably achieved by a 30-gauge iron-constantan "J-type" thermocouple. The controller uses this information to regulate the heat coil 31 according to the predetermined temperature versus time profiles programmed therein and to actuate solenoid 18, as will be explained momentarily.

The fluid passing from the reaction compartment 30 to the return air compartment 34 must pass through sample compartment 27 (as shown in dashed lines). Sample compartment 27 will also be explained momentarily.

The fluid in return compartment 34 has been slightly cooled due to the heat transfer therefrom into samples located in sample compartment 27. The fluid in return compartment 34 is drawn through inlet opening 36 into blower compartment 28 where it is again forced, by action of the fan, out through outlet opening 37 into the heating compartment 39. Thus, the fluid chamber 11, when operating with vent door 14 closed, is a closed loop fluid chamber which continuously recirculates the fluid along a closed loop path through each compartment thereof in order to bring the contents therein to a uniform temperature. Continuous circulation of the air in the air chamber 11 allows the samples in sample compartment 27 to be brought to a predetermined temperature as quickly as possible, and then to be held at that temperature, if desired.

When the device 10 must be used to not only heat material located in the reaction compartment 27, but also to subsequently cool these materials as quickly as possible to a temperature at or above the ambient fluid (air) temperature, the controller 12 can be programmed to actuate solenoid 18 to cause vent door 14 to open and allow large quantities of ambient fluid to immediately flood the compartment 11 while heated fluid therein simultaneously escapes.

Deactivation of the heating coil 31 while continuing activation of the blower with vent door 14 open, will draw ambient fluid into return compartment 34 and from there into the blower compartment 28. The blower will then push this ambient fluid through heating compartment 29 where it will pass directly into reaction compartment 30 without being heated by coil 31. The ambient fluid then passes through the sample compartment 27 and escapes out of chamber 11 through the vent door 14. Due to the minimum thermal mass of material located in chamber 11, and the action of the blower fan, vast quantities of ambient fluid will be forced past the sample compartment 27, and from there out of the chamber 11. Thus, rapid cooling of samples or material located in the reaction compartment 27 is obtained.

The sample compartment 27 is sized so as to allow a plurality of samples, such as hollow elongate glass tubes containing a sample therein, to be easily located in a spaced apart orientation so that fluid may be evenly distributed around each sample. If desired, the sample compartment 27 may be sized and configured so as to allow insertion of a rack, basket, or the like which has been configured so as to accept a plurality of samples in uniform spaced apart configuration so as to simplify loading the samples into the sample chamber 27. Access to sample compartment 27 is accomplished by rotation of the vent door 14 to its open position. Once the vent door 14 is rotated to approximately 90 degrees from it's closed position, the sample compartment 27 is easily accessible there through. Also, as can be seen in FIGS. 1-3, rotation of vent door 14 approximately 90 degrees from its closed position causes return fluid compartment 34 to be substantially closed off from the reaction compartment 30. Thus, when the device 10 of the present invention is in a "cooling" mode, ambient fluid enters directly into the return fluid compartment 34 and is forced through the blower compartment 28, heating compartment 29, reaction compartment 30, and sample compartment 27 substantially along the same path as the closed loop fluid flow path described above. The fluid is then forced out of the air chamber 11 and prevented from passing back into air return compartment 34 by the positioning of the vent door 14 between the sample compartment 27 and the return fluid compartment 34.

Thus, the vent door 14 not only allows ambient fluid to enter the chamber 11, it can also prevent the fluid from recirculating in a loop fashion through the chamber 11. Instead, fluid is forced to pass through the sample compartment 27 and then out of the chamber 11 to aid in the rapid cooling of the sample contents and chamber 11.

When the device 10 of the present invention is used for cyclic DNA amplification, repetitive cycling through different temperatures is required. Samples containing a reaction mixture for the polymerase chain reaction generally must be cycled approximately 30 times through temperature changes which correspond to the denaturation, annealing and elongation phases of the amplification process.

The device 10 of the present invention, due to its novel characteristics described above, is capable of cycling samples in significantly shortened periods compared to the prior art. For example, the DNA amplification application of the embodiment represented in the figures can pass through a temperature versus time profile cycle in 30-60 seconds (see FIG. 5). This same cycle using prior art devices would take approximately 5-10 times longer. These low cycle times have proven also to increase yield and specificity of the polymerase chain reaction over prior art cycling.

EXAMPLE 1

The polymerase chain reaction was run in a 10 μl volume with 50 ng of human genomic template DNAes, 0.5 mM of each deoxynucleotide, 500 nM of each of two oligonucleotide primers GGTTGGCCAATCTACTCCCAGG (SEQ ID NO:5) and GCTCACTCAGTGTGGCAAAG (SEQ ID NO:6) in a reaction buffer consisting of 50 mM Tris-HCl (pH 8.5 at 25° C.), 3.0 mM magnesium chloride, 20 mM KCl, and 500 μg/ml bovine serum albumin. Thermus aquaticus DNA polymerase (0.4μ) was added, the samples placed in 8 cm long, thin-walled capillary tubes (manufactured by Kimble, Kimax 46485-1), and the ends fused with laboratory gas burner so that an air bubble was present on both ends of each tube.

The capillary tubes were then placed vertically in a holder constructed of 1 mm thick "prepunched perfboard" (manufactured by Radio Shack). The mixture was cycled 30 times through denaturation (90-92° C.), annealing (50-55° C.), and elongation (72-75° C.) to give the temperature versus time profile of FIG. 5. Temperature monitoring of the capillary tubes was done with a miniature thermocouple (IT-23, Sensortek, Clifton, N.J.) placed in 10 μl of deionized water and connected to a thermocouple monitor (BAT-12, Sensortek). Amplification products were fractionated by electrophoresis on a 1.5% agarose gel. Specific amplification products were obtained in good yield.

Due to the fact that the device 10 of the present invention uses air as the thermal transfer medium instead of water, it has the advantage that heat transfer occurs through a low heat capacity medium (air) which can be warmed very rapidly.

Figure 5:
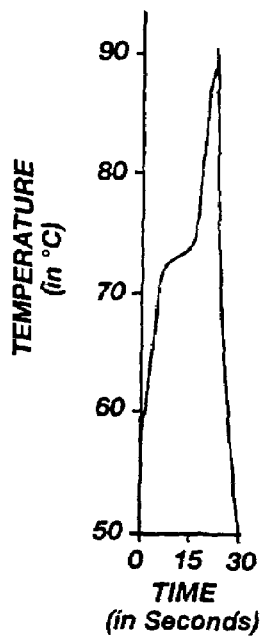
FIG. 5 shows an optimized temperature versus time profile for a polymerase chain reaction using the thermal cycling device of the present invention.

The response time for sample cooling is very fast due to the use of thin walled glass capillary tubes for holding samples, instead of plastic microfuge tubes as has been done in the past with prior art processes, and by minimizing the thermal mass of material inside the chamber 11 (see FIG. 5). Such response times can allow for optimization of the time and temperature requirements for the denaturation, annealing, and elongation steps in the polymerase chain reaction.

Further, shortened "ramp" times are obtained, i.e., the time required to bring the temperature of the sample from one temperature level to the next temperature level corresponding to phases in the amplification process is shortened. This decreases the time required for a complete amplification, as well as allowing specific study of annealing, denaturation and enzyme kinetics within a polymerase chain reaction protocol.

Figure 4:
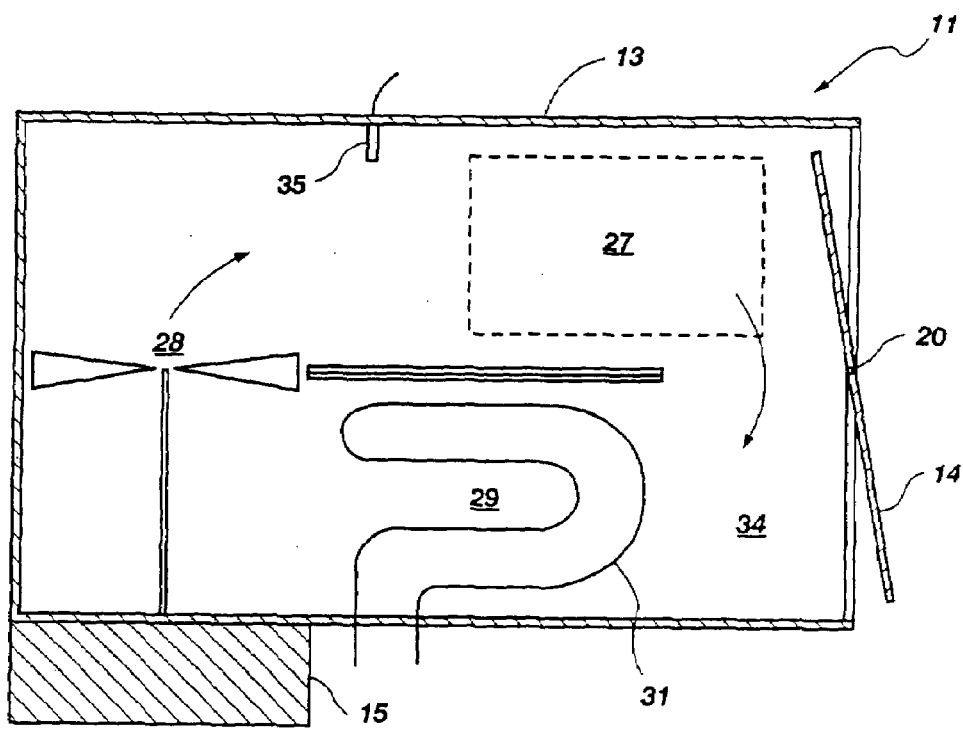
FIG. 4 shows an interior plan view of the fluid chamber of another embodiment of the present invention.

The baffles 32 and 33 (as shown in FIG. 3) may be used if desired to achieve better temperature homogeneity within the sample compartment 27. As shown in this embodiment, baffles 32 and 33 decrease the temperature variation in the reaction compartment 30 from about 110° C., to about 2° C. If desired, further (or more complicated) baffles may be used to further decrease the temperature variation in reaction compartment 30. Alternately, as shown in FIG. 4 the fan may be positioned downstream from the heating coil 31, but before the sample compartment 27 to achieve more uniform mixing.

Amplification products obtained through the use of apparatus 10 are at least qualitatively and quantitatively as desirable as those obtained through the manual water bath cycling method. However, advantages in specificity and yield are possible with rapid thermal control of the reaction mixture.

Figure 6:
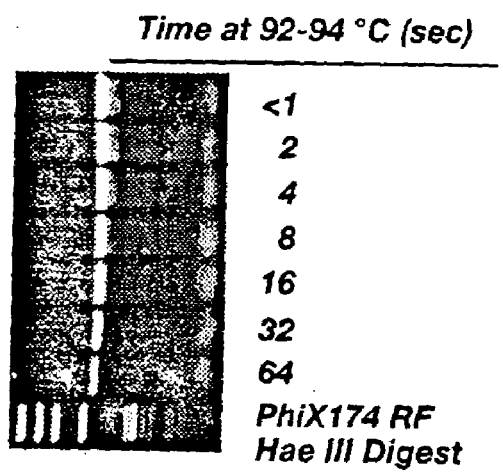
FIG. 6 shows graphically the effect of denaturation time on polymerase chain reaction yields using one thermal cycling device of the present invention.

FIG. 6 shows the effect of the temperature versus time profile of FIG. 5 as used with the thermal cycling apparatus 10 on specificity (i.e., one specific product yield as opposed to a plurality of similar or "shadow" products). As can be seen, the shorter the ramp and annealing time, the greater the product specificity. The rapid temperature response of the apparatus 10 allows improved specificity and yield which is not possible with prior art systems.

Figure 7:
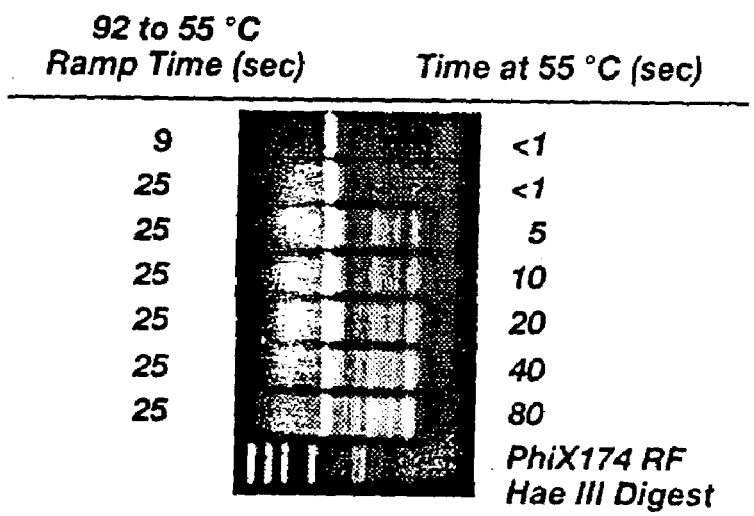
FIG. 7 shows graphically the effect of annealing time on polymerase chain reaction specificity and yields using the thermal cycling device of the present invention.

FIG. 7 shows the effect of varying the denaturation time of the temperature versus time profile of FIG. 5 as used with the thermal cycling apparatus 10 of the present invention on DNA amplification yields. The brighter vertical lines each correspond to a particular time at a denaturation temperature. As can be seen, the yield is greatest at the shortest possible denaturation time. Such a result is not possible with prior art systems.

As has been shown, by decreasing the thermal capacity (thermal mass) of the apparatus 10, the present invention can markedly decrease the total time required for carrying out the polymerase chain reaction. In addition, the use of small sample volumes further shortens the total time required for the reaction and also reduces the amounts of expensive reagents which must be used by up to about 90%, thus further reducing the cost of carrying out procedures using the present invention. For example, in the embodiment represented in FIGS. 1-3, capillary tubes 108 having inner diameters in the range from about 0.25 mm to about 1.0 mm can desirably be used. In some applications, capillary tubes 108 having inner diameters in the range from about 0.02 mm to about 0.1 mm can also be desirably used.

The apparatus 10 of the present invention is useful for amplifying DNA from any source. Although particular configurations and arrangements of the present invention have been discussed in connection with the specific embodiments of the thermal cycling device 10 as constructed in accordance with the teachings of the present invention, other arrangements and configurations may be utilized. For example, various fluids other than air, of generally low thermal mass, may alternatively be used in the device 10.

Figure 8A:
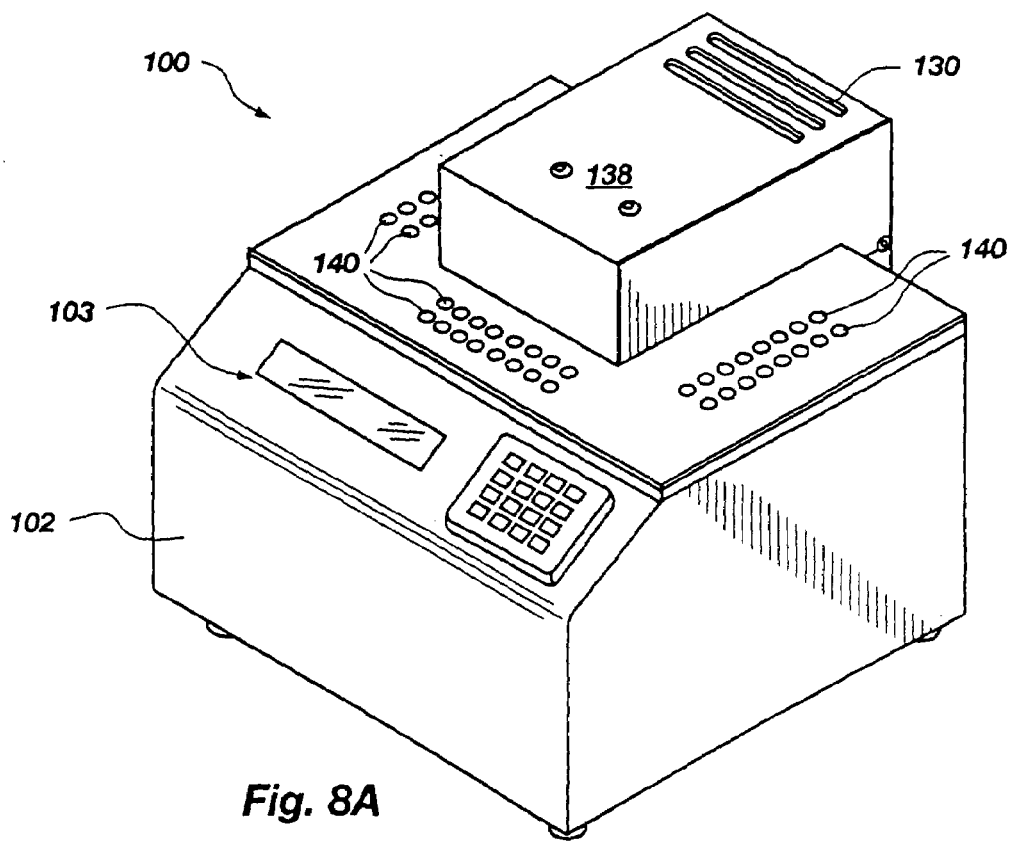
FIGS. 8A-B, which are perspective and elevational cross sectioned views, respectively, of another preferred embodiment of the present invention.
Figure 8B:
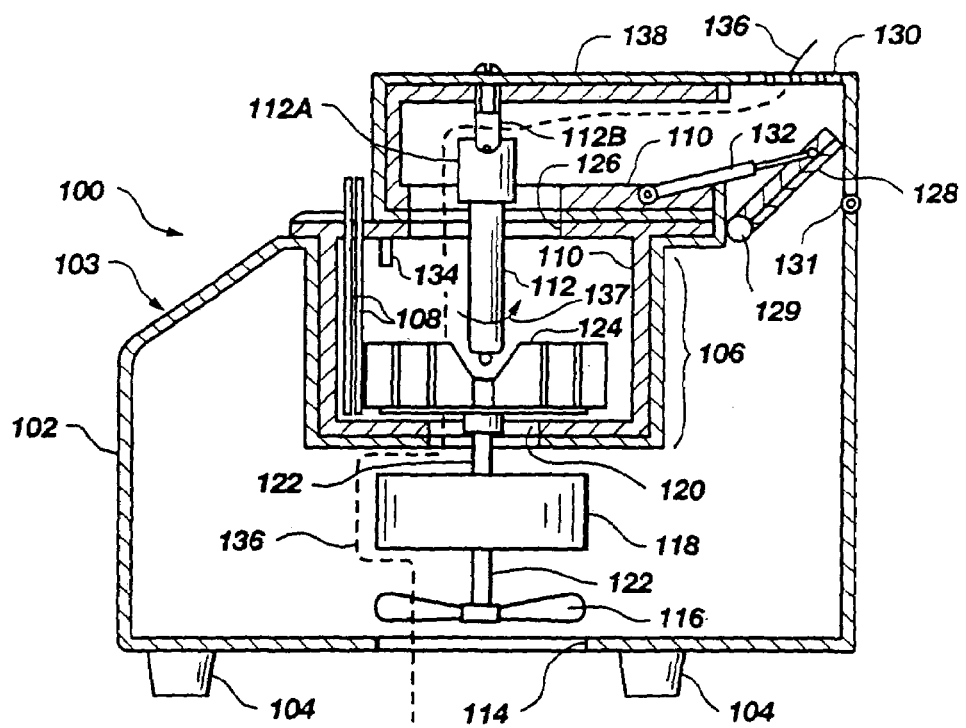
Figure 8C:
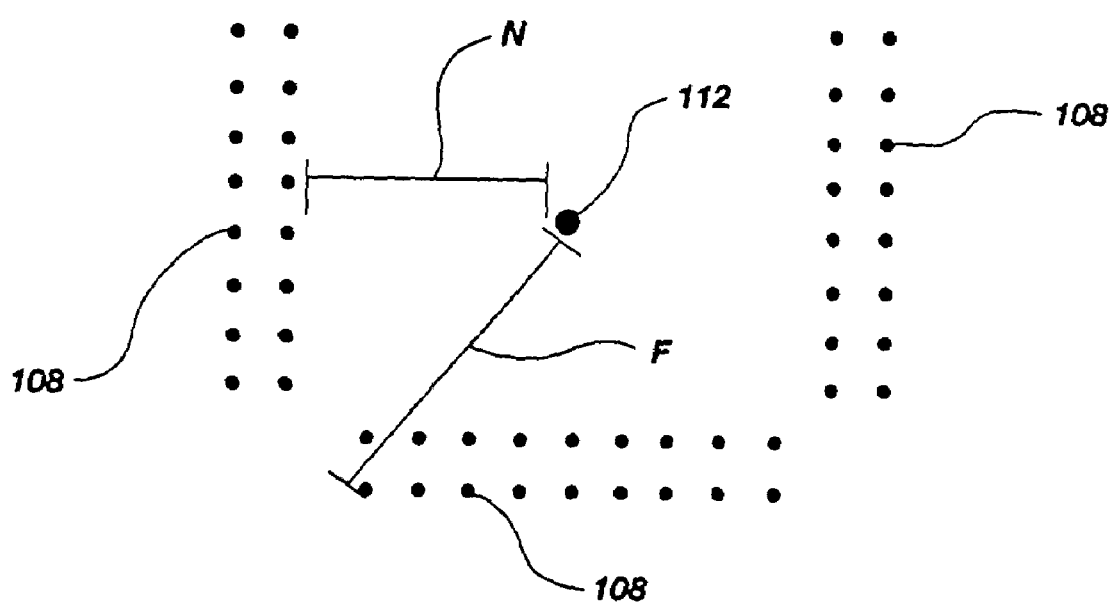
FIG. 8C is a diagrammatic representation of the relationship of the heat producing element and the capillary tubes holding the biological samples in the embodiment illustrated in FIGS. 8A-B.

Another embodiment of the present invention is represented in FIGS. 8A-C. FIG. 8A is a perspective view and FIG. 8B is an elevational cross sectioned view of the additional embodiment. It will be understood that many of the earlier explained components and teachings also have application in the embodiment illustrated in FIGS. 8A-C. Thus, only the pertinent additional information concerning this embodiment will be provided below. Importantly, in the embodiment of FIGS. 8A-C, the heat producing element is adjacent to the biological sample containers allowing faster heating and cooling of biological samples as explained below.

As will be appreciated shortly, the apparatus of FIGS. 8A-C provides even greater improvement over the prior art in the speed at which thermal cycling can be carried out, e.g., 15 or 30 cycles of DNA amplification in 30, 15, 10, or even fewer, minutes. Furthermore, the apparatus 100 provides better thermal homogenization throughout the samples than previously possible.

Shown in FIG. 8A is the general configuration of the housing 102 of the embodiment. The housing 102 rests on feet 104 (best seen in FIG. 8B) and functions to hold the other described structures in place and to isolate those structures which become hot from the surrounding environment. Included in the embodiment 100 of FIG. 8A are input keys 25 and a display 26 as in the previously described apparatus 10. The previously described control structures can readily be modified or used as a pattern for a control means for use in the embodiment of FIGS. 8A-C.

As shown best in the cross sectional view of FIG. 8B, a sample chamber is designated by bracket 106. A lid 138 connected to the housing 102 by a hinge 131 can be opened to allow access to the sample chamber 106. The sample chamber 106 is preferably cylindrical in shape but can be of any shape or size required by the particular application.

The sample chamber 106 is preferably lined with a black colored foam material 110 whose surface has light absorbing characteristics with the bulk of the thickness of the foam having insulating characteristics. The black foam material can be one which is readily available in the art and one fabricated from a plastic material. The foam 110 is preferably a material which is readily cooled by the air passing there over, i.e., the material has low thermal conductivity and a porous surface.

The dark or black porous surface of the material converts shorter wavelength radiation striking the surface into longer wavelength radiation, i.e., heat, which is radiated into the sample chamber.

The foam 110 functions to thermally isolate the sample chamber from the surrounding air space in the housing and also to convert the light emitted by lamp 112 into thermal energy. The foam 110 can be replaced with other structures. For example, a material having a black, dark, or other nonreflective surface, such as a thin sheet of polycarbonate having one surface painted black, can be backed by an insulative material, such as a fiberglass or foam material. The black or dark surface, which can be painted on a number of different substrates, converts shorter wavelength radiation striking it into thermal radiation while the insulative material thermally isolates the sample chamber from the surrounding environment. Thus, using the teachings provided herein, those skilled in the art can utilize many different materials and structures as a lining for the sample chamber.

The lamp 112 is preferably a 500 watt halogen lamp. If appropriate control devices are used, higher power lamps or a plurality of lamps, such as four 500 watt halogen lamps, can be used. A lamp socket 112A is attached to the housing 102 by a support 112B. The lamp 112 is able to very rapidly and uniformly heat the sample chamber 106 to the desired temperature. Other sources of heat, i.e. infrared radiation, such as the earlier described nichrome wire element, can also be used within the scope of the present invention.

Represented in FIG. 8B are two thin-walled capillary tubes 108 such as those described earlier. While two thin-walled capillary tubes 108 are shown, the sample chamber 106 can hold many such tubes. The thin-walled capillary tubes 108 have several important advantages over previously used devices as described earlier and, together with the sample chamber 106, function as the one presently preferred example of a means for holding a biological sample.

It will be appreciated that many other structures performing equivalent or similar functions can also be used. The thin-walled capillary tubes 108 are preferably left partially extending out of the sample chamber through apertures 140 for ease of access but may be completely contained within the sample chamber 106 as may numerous other fluid holding structures which are suited to particular applications. The preferred thin-walled capillary tubes 108 have a capacity of about 10 µl. As will be understood, the volume of the sample should be keep small, and the surface area of the sample holding structure relatively large, and together they present a relatively small thermal mass. It is also preferred that the sample holding structure contain a volume anywhere from about 1 pl to about 10,000 µl but those skilled in the art will appreciate that other volumes of samples can also be used within the scope of the present invention if the different thermal mass of the structure is considered.

The lamp 112 and the insulative foam 110 together provide rapid and uniform heating of the sample contained in the thin-walled capillary tubes 108 and the air contained within the sample chamber 106. A thermocouple 134 is included within the sample chamber 106 to sense the temperature within the chamber and is used to maintain the desired temperature within the sample chamber as earlier described.

The thermocouple 134 is preferably one available in the art whose thermal response substantially matches the thermal response of the biological sample and the container holding the same. Such thermocouples can be commercially obtained from sources such as Idaho Labs which manufactures a line of thermocouples referred to as metal sheathed, J-type thermocouples. The matching of the thermal response of the thermocouple to that of the biological sample and container can be preferably carried out by inserting a micro thermocouple, such as the model IT-23 thermocouple available from PhysiTemp as known in the art, into a typical biological sample being held by the chosen container and subjecting the sample and the thermocouple under test to the same temperature changes. The thermocouple under test, or some external criteria, can be changed until the thermal response of the thermocouple suitably matches the thermal response of the sample and its container.

The arrangement represented in FIG. 8B provides more uniform heating and cooling of the sample than previously available devices. In previously available devices, transfer of heat throughout the sample is carried out by convection through the sample. Convection induced movement of the sample within whatever structure is used to hold the sample is caused by temperature gradients or differences in the generally small biological samples (e.g., 10-100 µl).

The effect of temperature gradients within the sample become more pronounced and more difficult to control as the cycle time for a sample decreases. The existence of uneven temperatures within a sample, and particularly the reliance on "mixing by convection" within the sample relied upon by the prior art devices, generally increases the cycle time for a sample and likely has deleterious effects on the biological sample. The apparatus 100 is capable of providing heating and cooling such that thermal differences within a 10 µl sample are maintained at not greater than ±1° C. at all times during a 30 second cycle.

In order to promote uniform heating and cooling, it is preferred that the thin-walled capillary tubes 108 be at least somewhat uniformly spaced from the heat source, for example, lamp 112 in apparatus 100. FIG. 8C provides a diagrammatic top view of the lamp 112 and the plurality of thin-walled capillary tubes 108 as arranged in the apparatus 100 represented in FIGS. 8A-B.

In the arrangement represented in FIG. 8C, the thin-walled capillary tubes 108 which are farthest from the lamp 112 (as indicated by line F) are preferably no more than substantially 40%, and more preferably no more than substantially 25%, farther from the lamp 112 than the distance between the lamp 112 and those thin-walled capillary tubes 108 which are closest to the lamp 112 (as indicated by line N). For example, the distance indicated by line N can be about 7.3 cm while the distance indicated by line F can be about 8.5 cm.

It will be appreciated that the arrangement of the thin-walled capillary tubes 108 can be other than that represented in the figures, for example, circular or semi-circular. Moreover, it will appreciated that the point from which to measure the distance between the heat producing element and the sample containers will vary as the type and size of the heat producing element varies. For example, the heat producing element may comprise a plurality of lamps or electric resistive elements which vary in shape and size. In some embodiments, it may also become important to consider the distance from the sample chamber wall the sample containers are positioned. In the illustrated embodiment, the apertures 140 (see FIG. 8A) function as a means for holding the sample containers but other structures performing equivalent functions can also be used in accordance with the present invention.

The apparatus 100 also cools the samples contained in the capillary tubes 108 very rapidly and uniformly. In order to cool the sample chamber 106, air from outside the housing 102 is drawn into the interior of the housing through a lower housing portal 114 by a fan 116 which is connected to a motor shaft 122 driven by a motor 118. Since rapid cooling of the sample chamber is desired, it is preferred that the combination of the motor 118 and the fan 116 be able to move sufficient volumes of air into the sample chamber 106 and then disperse that air inside the sample chamber 106, as will be explained shortly. Arrangements other than the motor 118 and fan 116 illustrated in FIG. 8B can also be used within the scope of the present invention.

The use of air as the thermal transfer medium, in contrast to other gases and liquids, has the advantages of being inexpensive, readily available, easily mixed, and never making a mess. In the case of the described embodiments, the high surface area-to-volume ratio of the sample containing capillary tubes provides for rapid thermal transfer using air as the thermal transfer medium.

During cooling portions of the thermal cycle, the action of the fan 116 draws ambient temperature air into the housing 102. A vent door 128, articulating on hinge 129, is provided. The vent door 128 is automatically opened by way of a solenoid 132 so that the interior of the housing 102 is sealed off from the upper housing portal 130. In some embodiments, the solenoid 132 is preferably replaced by a stepper motor as is known in the art. The use of a stepper motor allows the vent door 128 to be accurately and incrementally opened and closed in accordance with the needs for heating and cooling the samples. Those skilled in the art will be able to derive an appropriate control mechanism for use with a stepper motor, for example an SC-149 stepper motor controller (available from Alpha Products) as known in the art, using the information set forth herein.

Due to the arrangement of the lower sample chamber portal 120 and the larger cross sectional area and position of the upper sample chamber portal 126, room temperature air is moved into the sample chamber 106 and is dispersed and mixed within the sample chamber 106 by a paddle 124 which is connected to the motor shaft 122. The paddle 124 should rotate at a relatively high rate, for example, fast enough to create air velocities of around preferably about 250, more preferably 500, and most preferably 1000 meters per minute within the sample chamber 106. With the paddle 124, which can be a single or a multivane paddle, rotating at a high speed, air is moved, or drawn, into the sample chamber 106 and vented out of the sample chamber 106 following the path indicated by the dashed line 136. The rotation of the paddle 124 also promotes mixing of the air entering the sample chamber 106 and ensures the most efficient transfer of thermal energy from the surfaces of the thin-walled capillary tubes 108 to the air passing through the sample chamber 106. It will be appreciated that structures other than those illustrated herein can perform equivalent functions.

As the solenoid 132 is actuated to open the vent door 128, all of the room temperature air moved into the sample chamber 106 is exhausted through a sample chamber upper portal 126 and then through the upper housing portal 130 carrying the heat from the sample chamber 106 to the surrounding atmosphere. The rapid mixing of the air that passes through, and is disbursed in, the sample chamber 106 results in rapid and uniform cooling of the samples.

EXAMPLE 2

Figure 9A:
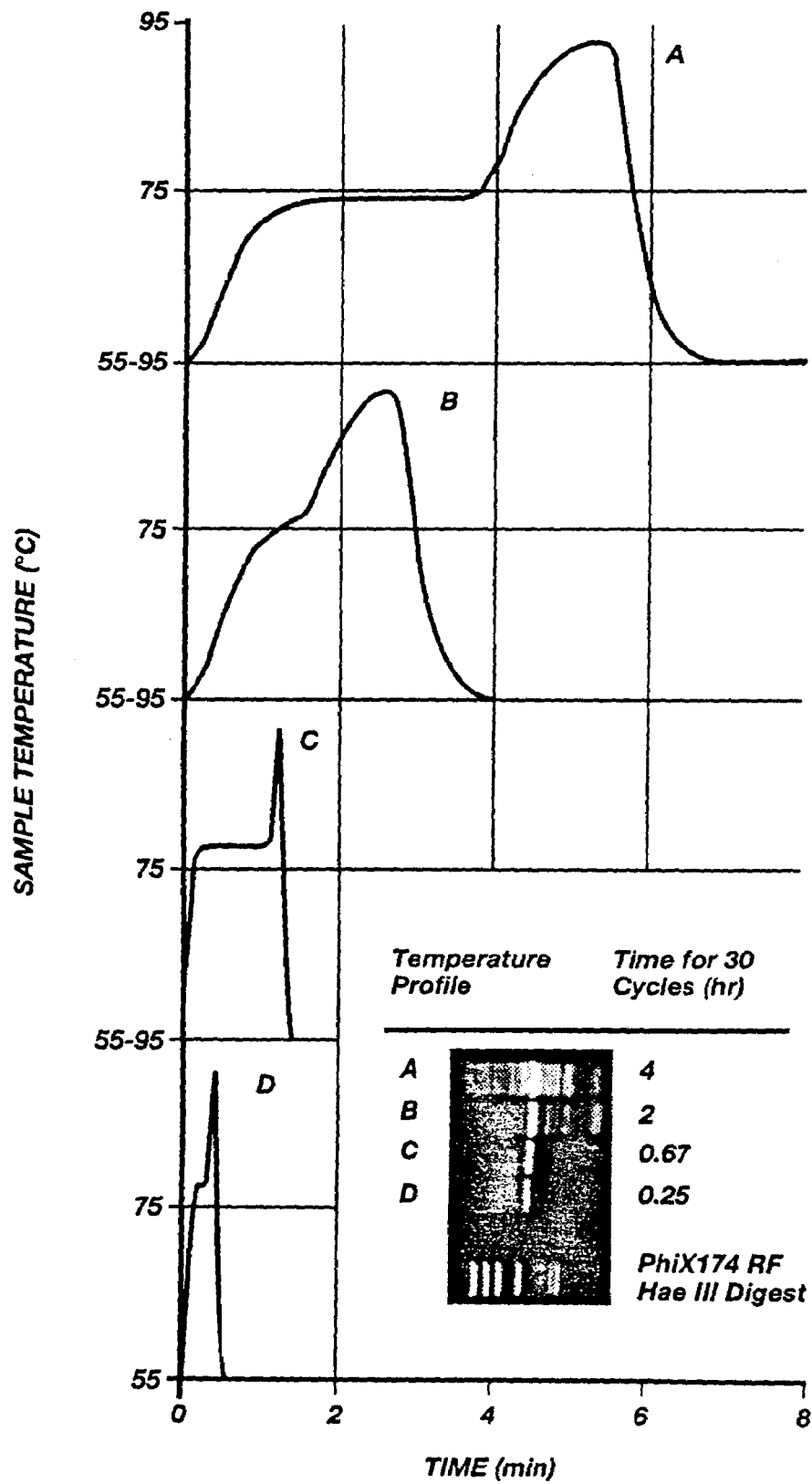
FIG. 9A shows the results of four different temperature/time profiles (A-D) and their resultant amplification products after thirty cycles (A-D).

FIG. 9A shows the results of four different temperature/time profiles (A-D) and their resultant amplification products after thirty cycles (A-D). The profiles A and B in FIG. 9A were obtained using a prior art heating block device using the prior art microfuge tube. As can be seen in FIG. 9A, the transitions between temperatures are slow and many nonspecific bands are present in profiles A and B. Profile B shows improvement in eliminating some of the nonspecific bands (in contrast to profile A) by limiting the time each sample remains at each temperature thus indicating that shorter times produce more desirable results.

Profiles C and D were obtained using the apparatus of FIGS. 8A-B. As can be seen in FIG. 9A, amplification is specific and, desirably, even though yield is maximal in C (60 second elongation) it is still entirely adequate in D (10 seconds elongation).

The optimal times and temperatures for the amplification of a 536 bp fragment of β-globin from human genomic DNA were also determined. Amplification yield and product specificity were optimal when denaturation (93° C.) and annealing (55° C.) were less than 1 second. No advantage was found to longer denaturation or annealing times. The yield increased with longer elongation times at (77° C.) but there was little change with elongation times longer than 10-20 seconds. These unexpected results indicate that the previously available devices used for DNA amplification are not maximizing the conditions needed to optimize the physical and enzymatic requirements of the reaction.

Further information can be obtained from: Wittwer, Carl T., Marshall, Bruce C., Reed, Gudrun B., and Cherry, Joshua L., "Rapid Cycle Allele-Specific Amplification with Cystic Fibrosis $\Delta F_{508}$ Locus," 39 *Clinical Chemistry* 804 (1993) and Wittwer, Carl T., Reed, Gudrun H., and Rire, Kirk M., "Rapid DNA Amplification," THE POLYMERASE CHAIN REACTION 174 (1994) which are both now incorporated herein by this reference.

From the information provided in FIG. 9A, it can be seen that the embodiments of the present invention subject the samples placed therein to rapid thermal cycling wherein the temperature of the sample is increased and decreased at a rate preferably at least as great as 0.5° C./second. In the case of the present invention carrying out the polymerase chain reaction, the temperature change is preferably carried out over an approximate range of between 30° C. to 50° C. It is preferred that the thermal cycles be carried out quickly enough to complete at least thirty thermal cycles in forty minutes and more preferably complete thirty thermal cycles in twenty minutes and most preferably complete thirty thermal cycles in ten minutes.

The apparatus 100 more preferably increases and decreases the temperature of the sample at a rate at least as great as 1.0° C./second and even more preferably at a rate at least as great as 4.0° C./second and most preferably at a rate at least as great as 10.0° C./second. Critically, the biological sample, not just the surrounding medium and/or the sample container, must undergo the specified thermal change. The previously available devices, while having the drawback of not being able to perform thermal changes as rapidly as the present invention, also did not recognize the problem of changing the temperature of the sample, not just the temperature of the surrounding medium and container, rapidly and uniformly.

Figure 9B:
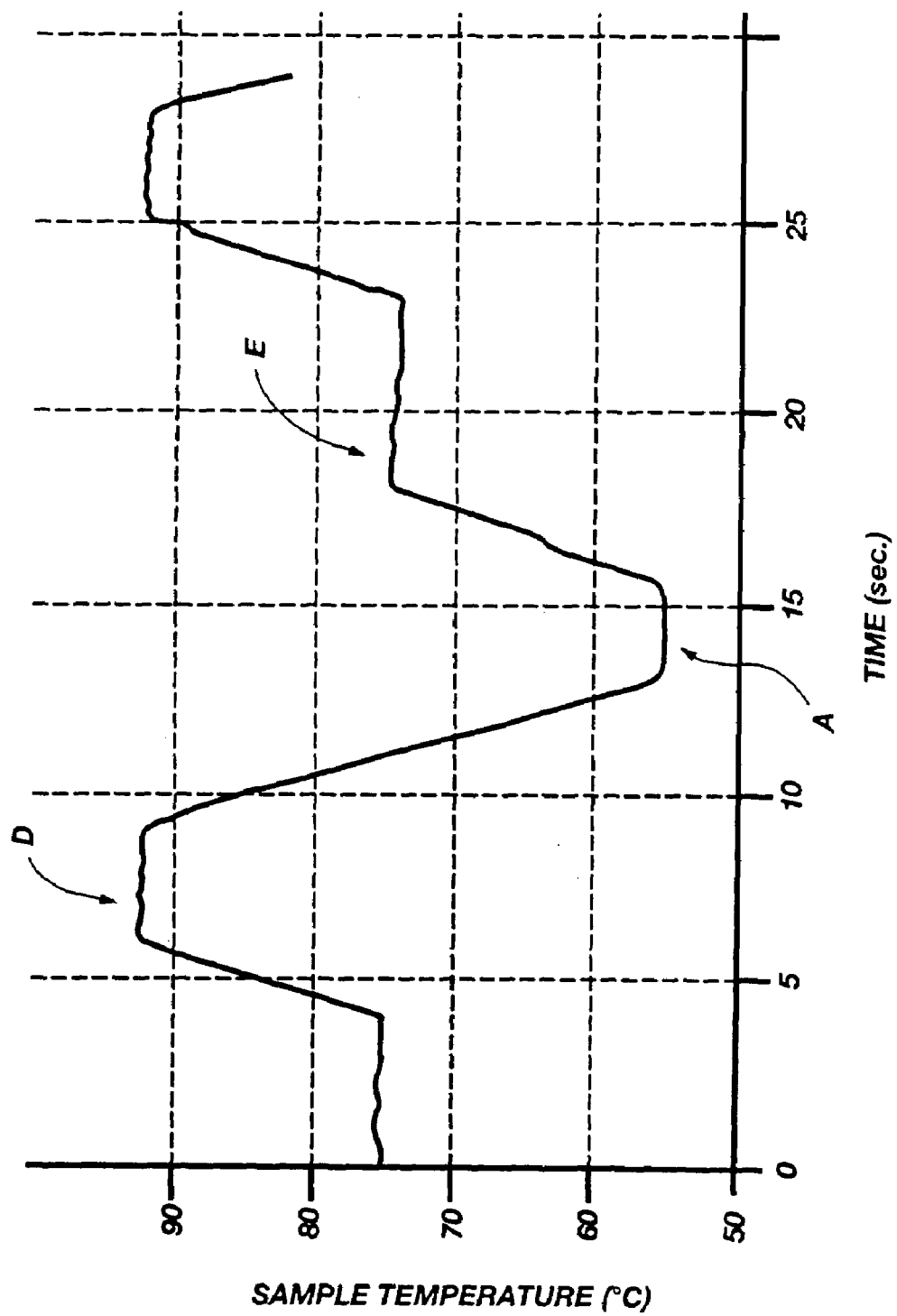
FIG. 9B shows a cycle of another preferred temperature/time profile used by the present invention.
Figure 9C:
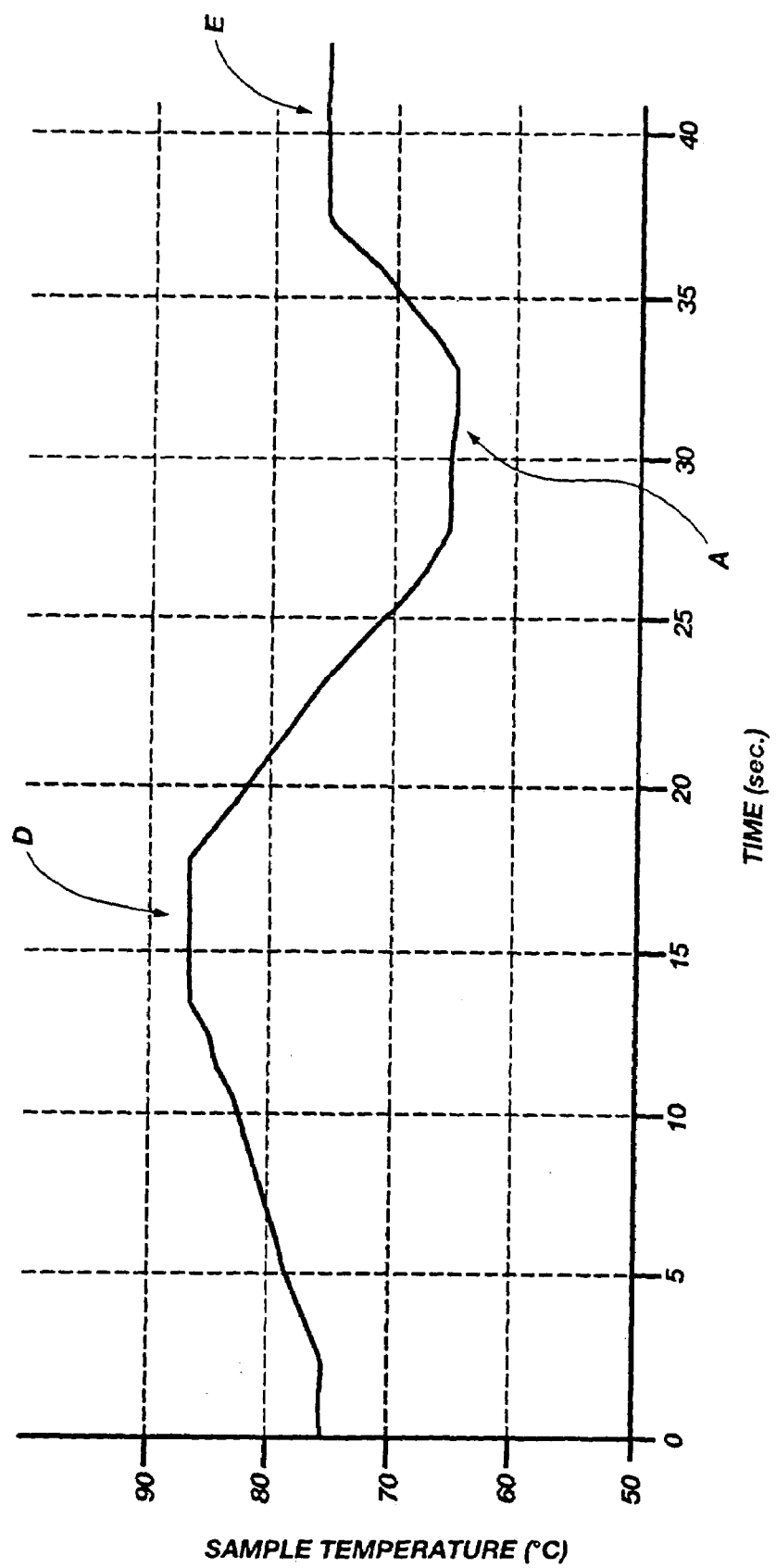
FIGS. 9C-G show exemplary cycles of other preferred temperature/time profiles used by the present invention.
Figure 9D:
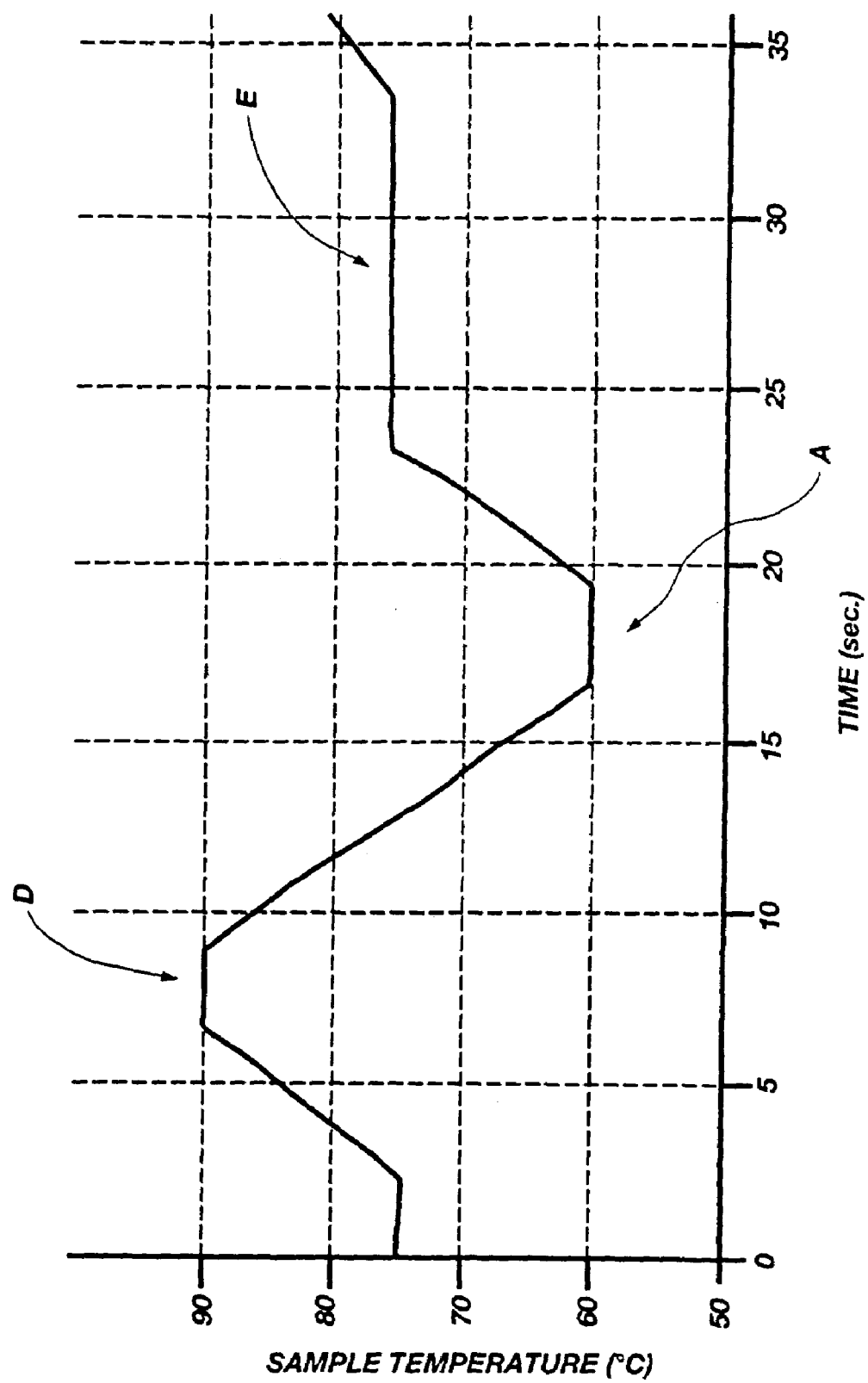
Figure 9E:
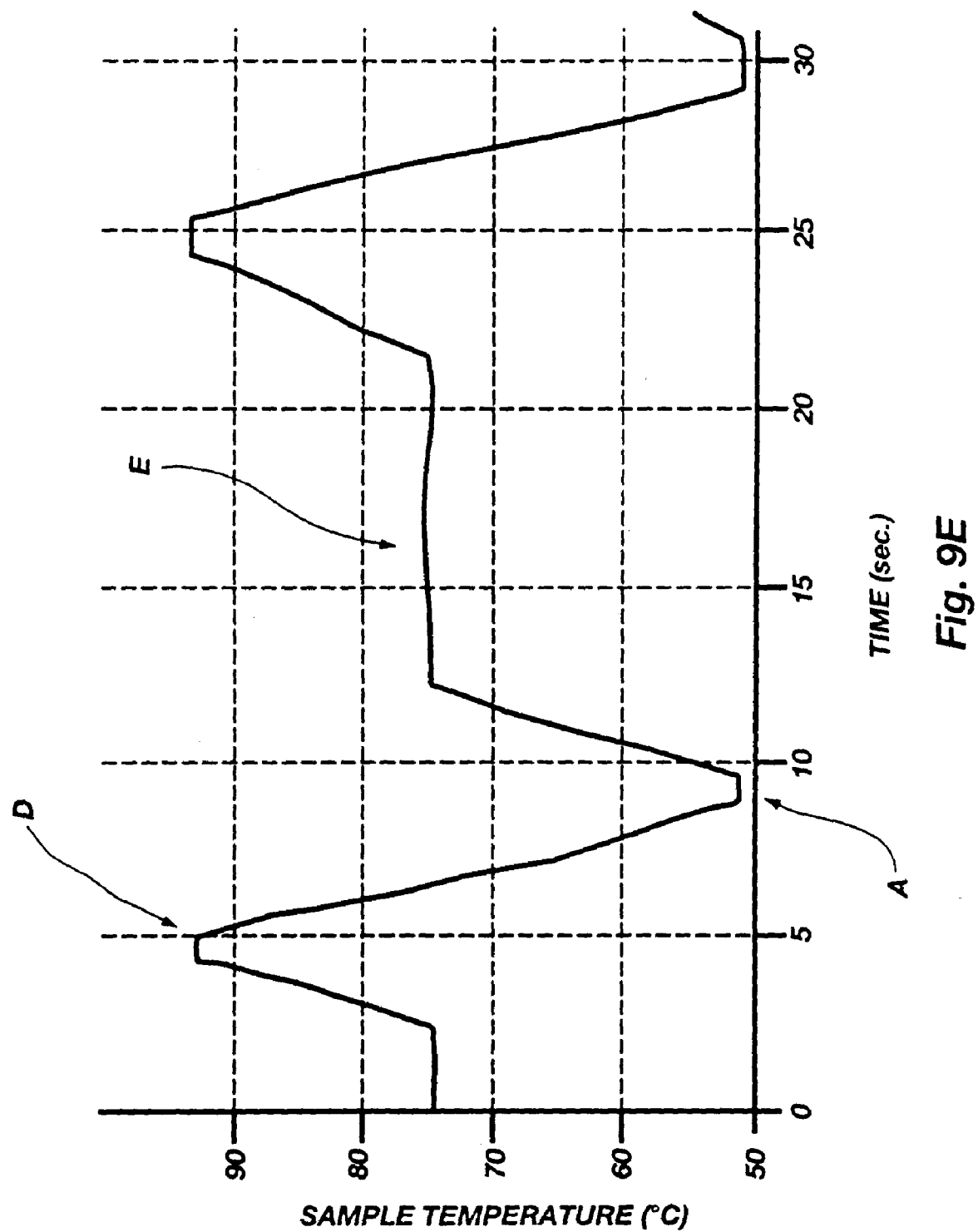
Figure 9F:
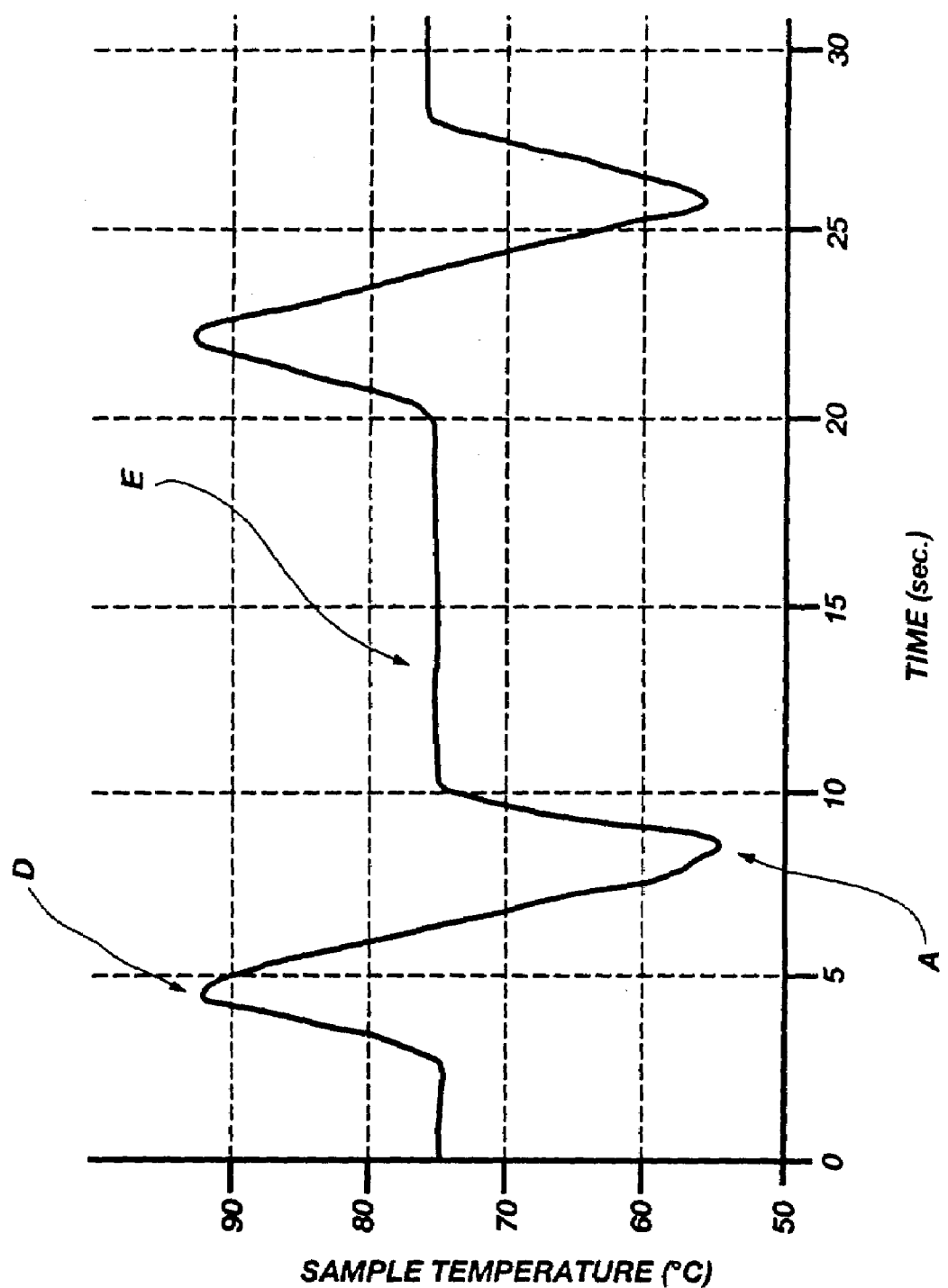
Figure 9G:
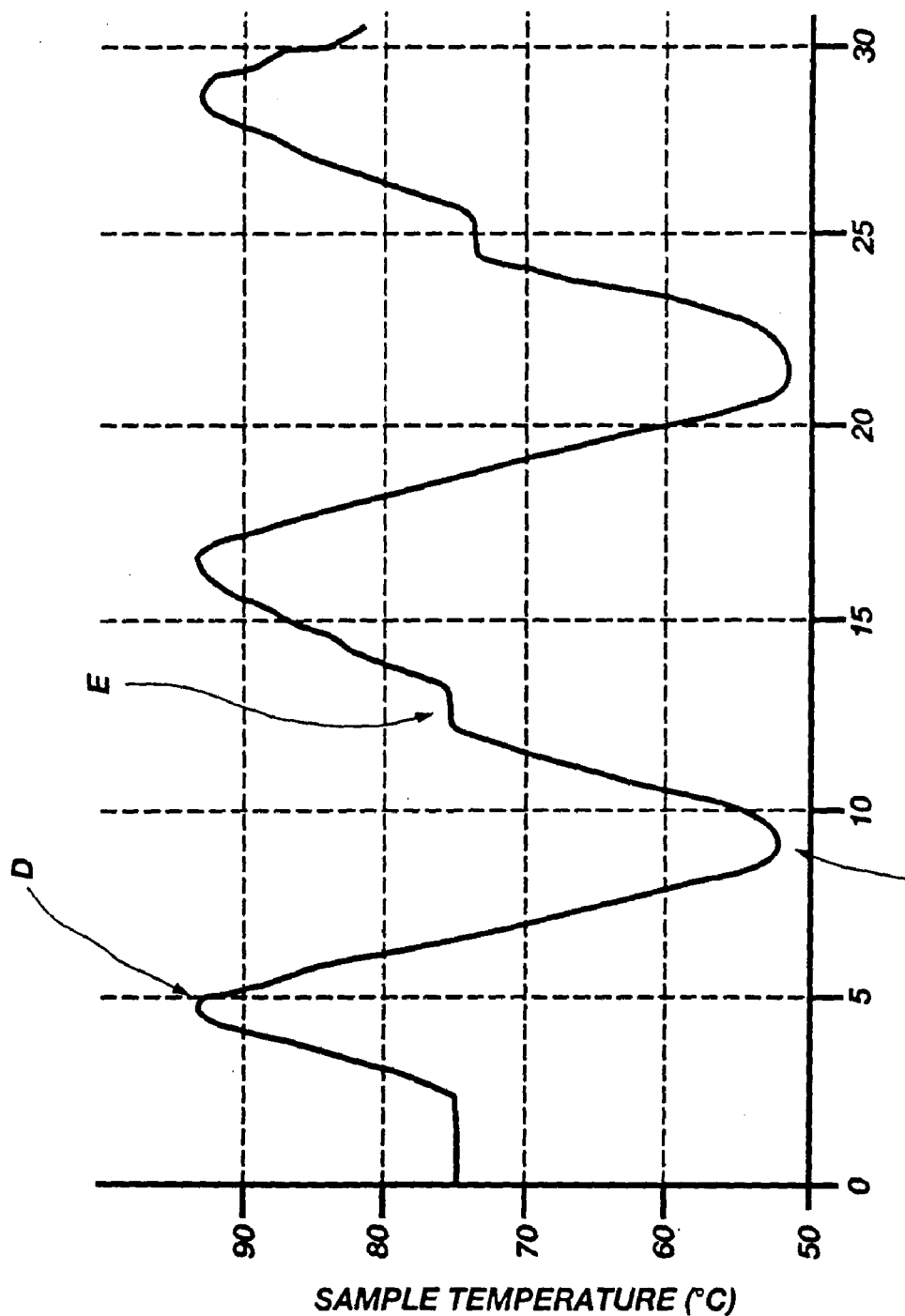

Referring now to the chart of FIG. 9B, the method of the present invention can desirably achieve thermal cycling preferably at a rate at least as great as 10° C./sec., and more preferably at a rate at least as great as 20° C./sec., over a temperature range of greater than about 20° C., more preferably over a temperature range of greater than about 30° C., and most preferably over a temperature range of about 40° C. FIG. 9B shows the temperature in ° C. of the biological sample, not just the surrounding air or container, as the biological sample undergoes thermal cycling. FIG. 9B shows a PCR sample beginning at about 74° C. and being heated to a denaturation temperature, indicated at D, of about 92° C. for 2 seconds. The sample is then cooled to an annealing temperature, indicated at A, of about 55° C. for two seconds. The transition between the denaturation temperature and the annealing temperature covers a range of 37° C. in just under 4 seconds providing a rate at least as great as 10° C./sec. The sample is then warmed to an extension temperature of 74° C. for five seconds as indicated at E in FIG. 9B. The cycling of the sample through the denaturation temperature, the annealing temperature, and the extension temperature is repeated thirty times or as many times as desired.

FIGS. 9C-G show exemplary cycles of other preferred temperature/time profiles which are achieved by the present invention. It will be understood that those skilled in the art can alter the represented temperature/time profiles to carry out specific processes in accordance with the present invention. Those skilled in the art will also appreciate that the previously available devices and methods, such as devices which conduct heat to and from the sample via a solid or liquid, cannot provide the resulting temperature/time profiles described herein. Moreover, the previously available devices and methods do not suggest or teach the temperature/time profiles described herein. Furthermore, it will be appreciated that the previously available devices and methods utilizing air as the transfer medium, for example previously available chromatographic ovens, cannot provide, and do not suggest or teach, the temperature/time profiles which are described herein and obtained by the practice of the present invention.

Figure 10:
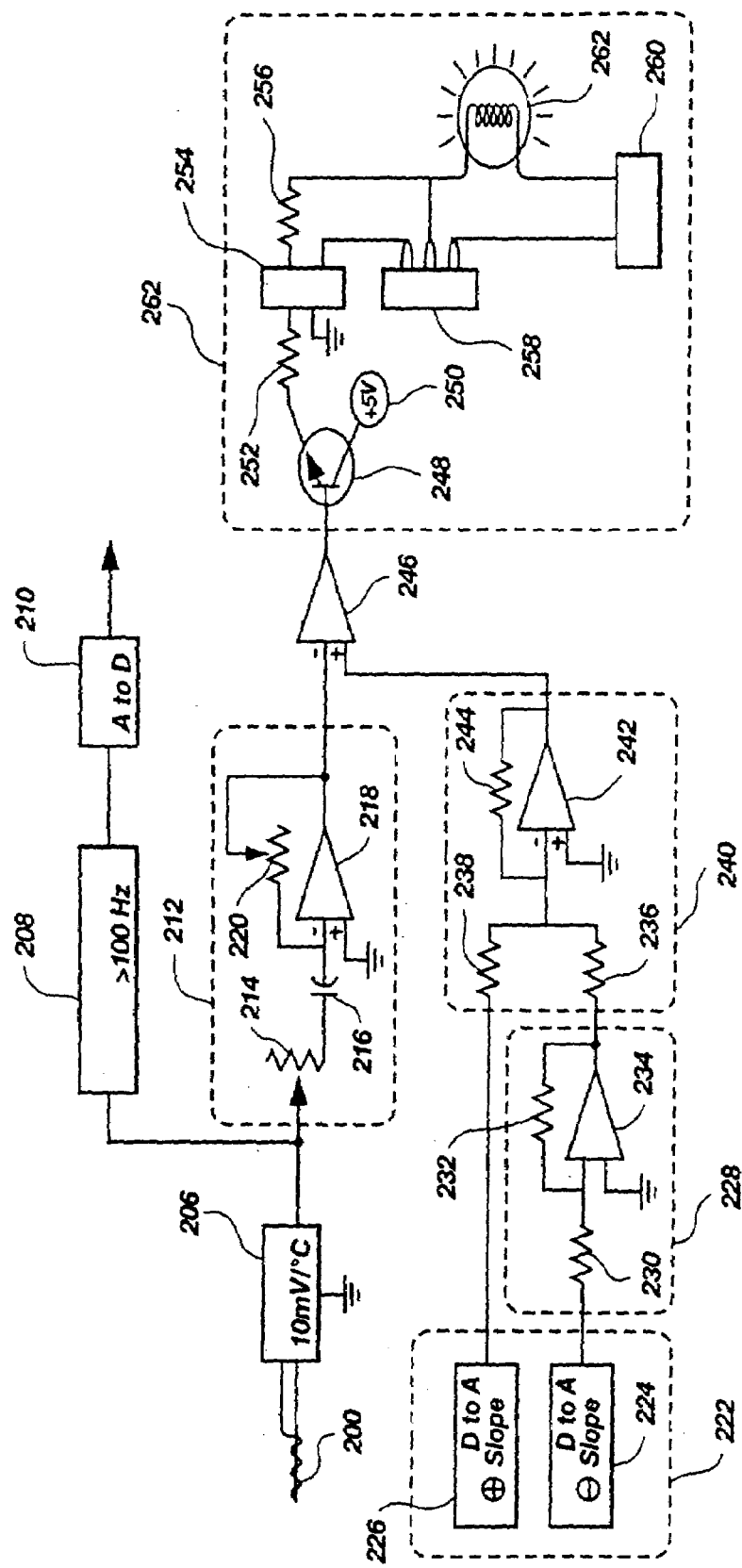
FIG. 10 provides a block diagram of a temperature slope control circuit in accordance with the present invention.

In order to provide the fastest thermal cycling time, it is preferred that the lamp (112 in FIGS. 8A and 8B) be rated at 2000 watts or a plurality of lamps be included which provide similar output. It is also preferred to include a temperature slope control circuit which is represented in FIG. 10 in conjunction with an A-bus controller/acquisition system using an 8052 micro controller board with a clock and high level program interpreter available from Alpha Products (model no. SP-127) of Darian, Conn. Exemplary programming code used in connection with the described micro controller is included in the Programming Code Appendix A attached hereto and incorporated herein. The programming code provided in Appendix A is a BASIC52 file for serial downloading into the micro controller and provides exemplary temperature slope control during thermal cycling. Use of the 2000 watt heat producing device and the described control structures allows thermal cycling rates of 20° C./sec. to be desirably obtained.

The preferred arrangement for the temperature slope control circuit represented in FIG. 10 will be explained with the understanding the additional necessary components not explicitly illustrated in FIG. 10 can readily be supplied by those skilled in the art.

The temperature slope control circuit of FIG. 10 includes a thermocouple 200 matched to the sample temperature response as explained earlier. The thermocouple 200 is connected to an integrated circuit 206, which preferably is one known in the art as an AD595, whose output is conveyed to a 4th order low pass filter 208 with a cutoff frequency of 100 Hz and to a 12 bit analog-to-digital convertor 210 whose output is used to provide a digital display of the temperature.

The output of the circuit 206 is also conveyed to a measured slope circuit 212. The measured slope circuit 212 preferably includes a 353 operational amplifier 218, a 100 KΩ potentiometer 214, a 1 MΩ potentiometer 230, and a 22 µF capacitor. The measured slope circuit 212 outputs a signal to the inverting input of a 353 operational amplifier 246.

A slope set circuit 222 includes a positive slope set digital-to-analog converter 226 and a negative slope set digital-to-analog converter 224. The digital-to-analog converters 224 and 226 are preferably 8-bit digital-to-analog converters referred to in the art as DA147. The slope set circuit can preferably receive instructions from another digital device (not illustrated in FIG. 10) such as a personal computer. The output of the slope set circuit 228 is communicated to a summing circuit 240.

The summing circuit 240 preferably includes 100 KΩ resistors 236, 238, and 244 and a 353 operational amplifier 242. The output of the summing circuit 240 is conveyed to the non-inverting input of the operational amplifier 246 and represents the desired slope of the temperature change. The output of the operational amplifier 246 is provided to a transistor 248 contained within a power switching circuit 262.

The power switching circuit 262 includes a 5 VDC supply 250 providing current to the transistor 248. The transistor 248 has its emitter connected to a 3010 circuit 254 by way of resistor 252 which is preferably a 330Ω resistor. The 3010 circuit 254 includes an output connected in series with a resistor 256 which preferably is a 180Ω resistor. A triac 258 is preferably used to control the current delivered to a lamp 262, or other heat producing device, from a source of AC current 260.

The temperature slope control circuit represented in FIG. 10, in cooperation with the other described system components, provides thermal cycling of biological samples as great as 20° C./sec over a temperature range of 30° C., and most preferably over a temperature range of 40° C., with homogeneity being maintained throughout the biological sample.

It will be appreciated that the systems described herein can readily be used for many different applications including: polymerase chain reaction processes; cycle sequencing; and, other amplification protocols such as the ligase chain reaction. The present invention also advantageously provides an apparatus for accurately controlling the temperature of samples located in the sample chamber and quickly and accurately varying the temperature of samples located in a chamber according to a predetermined temperature versus time profile.

As indicated earlier, and in contrast to the teachings of the prior art, the polymerase chain reaction can be performed rapidly. Using the methods and apparatus described herein, the necessary number of temperature cycles can routinely be completed in much less time than possible with the prior art devices, for example in less than 15 minutes. By minimizing denaturation and annealing times, the specificity and yield of rapidly cycled amplifications are also improved to an extent not otherwise previously possible. Moreover, in addition to facilitating rapid heat transfer, the use of optically clear sample containers, such as clear capillary tubes, allows for continuous fluorescence monitoring of DNA amplification in accordance with the present invention.

Figure 10A:
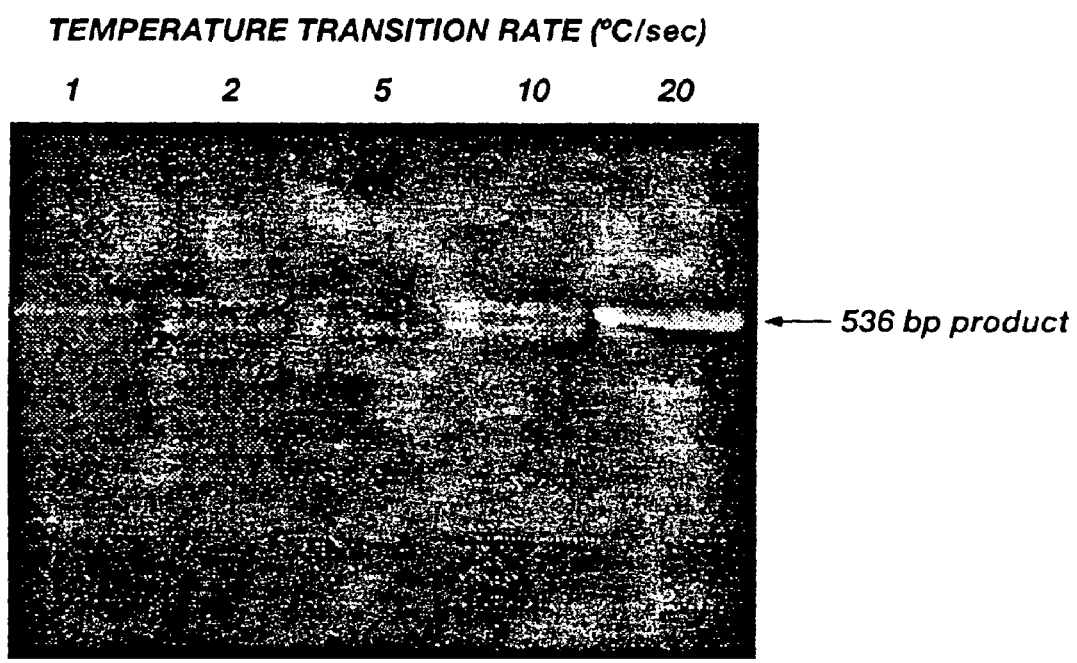
FIG. 10A is a graphical representation of the effect of the temperature transition rate from the product denaturation temperature to the primer annealing temperature on reaction product specificity.

FIG. 10A shows graphically the effect of temperature transition rates on PCR reaction specificity and yield using an apparatus of the present invention. The results of FIG. 10A were obtained using a 536 base pair fragment of the beta globin gene which was amplified from 50 ng of human genomic DNA with 50 mM Tris, pH 8.3, 2 mM $MgCl_2$, 50 μg/ml bovine serum albumin, 0.5 μM each primer, 0.2 mM each dNTP, and 0.4 U native Taq DNA polymerase in a 10 μl reaction. The human beta-globin primers RS42 and KM29 (536 base pairs) are described in C. T. Wittwer, G. C. Fillmore and D. R. Hillyard, "Automated Polymerase Chain Reaction in Capillary Tubes with Hot Air," *Nucl. Acids. Res.* 17:4353-4357. Temperature cycling parameters were 94° C. for 0 sec., 55° C. for 0 sec., and 72° C. for 10 sec. Thirty five cycles of amplification were performed with the indicated rates between all temperatures. The samples were electrophoresed on 1.5% agarose gels and stained with 0.5 μg/ml ethidium bromide. Specificity and yield both decrease as the temperature transition rate decreases.

Fluorescent probes can be used to detect and monitor DNA amplification. As known to those skilled in the art, useful probes include double-stranded-DNA-specific dyes and sequence-specific probes. With the intercalater ethidium bromide, UV-excited red fluorescence increases after amplification. While microfuge tubes have been used as a sample container for DNA amplification, the embodiments of the present invention described herein advantageously utilize sample containers with many of the characteristics of structures referred to herein as capillary tubes.

The use of the sample containers described herein allows detection of fluorescence while the sample is held within the container, as will be explained more fully hereinafter. Those skilled in the art will appreciate the number of different schemes of fluorescence detection of DNA amplification which are now available. For example, sequence-specific fluorescence detection is readily possible using the present invention and oligonucleotide hybridization probes. As another example, dual-labeled fluorescein/rhodamine probes can be cleaved during polymerase extension by 5'-exonuclease activity, separating the fluorophores and increasing the fluorescein/rhodamine fluorescence ratio.

Using the embodiments of the present invention described hereinafter, fluorescence can be measured after temperature cycling is complete, once per cycle as a monitor of product accumulation, two or more times during a temperature transition, or continuously within each cycle. In contrast to the present invention, previously available methods only cycle relatively slowly and do not teach acquisition and analysis of fluorescence during temperature changes.

The present invention allows cycle-by-cycle monitoring for quantification of initial template copy number. To carry out such cycle-by-cycle monitoring, fluorescence is acquired during the extension or combined annealing/extension phase of each cycle and related to product concentration. For example, a quantitative assay for hepatitis C RNA using the intercalater YO-PRO-1™ is known in the art and can be used in accordance with the present invention. For more information see Ishiguro, T., J. Saitch, H. Yawata, H. Yamagishi, S. Iwasaki, and Y. Mitoma, 1995, "Homogeneous quantitative assay of hepatitis C virus RNA by polymerase chain reaction in the presence of a fluorescent intercalater," *Anal. Biochem.* 229:207-213. Prior to the present invention, continuous fluorescence monitoring within each cycle during temperature transitions has not been attempted.

In accordance with one aspect of the present invention, one embodiment of the present invention disclosed herein is a rapid temperature cycler integrated with 2-color fluorescence optics to provide continuous fluorescence monitoring. As will be more fully discussed below, different preferred fluorescence techniques for monitoring DNA amplification are provided herein as specific examples of carrying out one aspect of the present invention. Those skilled in the art will be familiar with the use of ethidium bromide in fluorescence techniques which can be used in accordance with the present invention. In one presently preferred embodiment described below, it is preferred that SYBR® Green I, which is well known in the art and available from Molecular Probes of Eugene, Oreg., be used as a double-strand-specific dye.

In one presently preferred embodiment of the present invention, time, temperature, and fluorescence is acquired every 200 msec. during the amplification reaction. By acquiring data regularly during the reaction, the acquisition of such data reveals fine details of product denaturation, reannealing, and extension which is not available in the previously available apparatus and methods.

As will be appreciated by those skilled in the art, once-per-cycle monitoring of multiple samples undergoing DNA amplification is a powerful quantitative tool. Importantly, as will be appreciated by an understanding of this disclosure, continuous monitoring within a cycle can identify the nature of probe fluorescence, provide insight into DNA amplification mechanics not previously available in the art, and assess PCR product and probe melting curves to identify amplification products and mutations.

Figure 11:
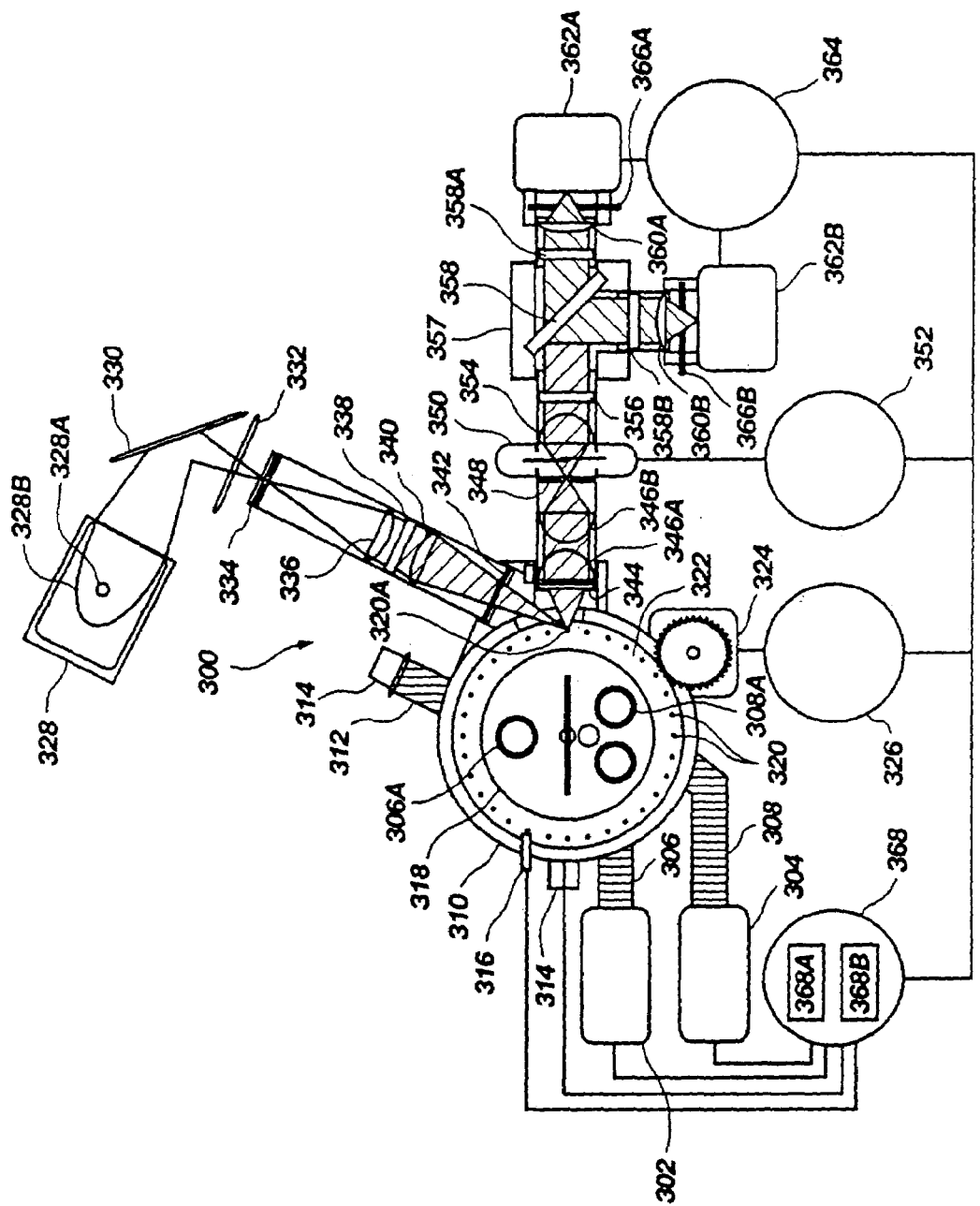
FIG. 11 is a schematic view of a preferred rapid temperature cycler with fluorescence detection in accordance with the present invention.

Referring now to FIG. 11, a schematic view of a preferred rapid temperature cycler with fluorescence detection is provided, generally designated at 300. A forced air hot air source 302 is preferably provided. The forced air hot air source 302 is preferably a commercially available device including a 1600 watt heating coil and fan. A cool forced air cool air source 304 is also preferably provided. The cool forced air source 304 is preferably a 2200 rpm shaded pole blower available in the art from Dayton of Niles, Ill., model no. 4C006B. It is preferred that the cool air source 304 provide ambient temperature air, but it is within the scope of the present invention to utilize a means for providing fluid that is at a temperature lower than ambient air temperature.

In the embodiment of FIG. 11, ducts 306 and 308 connect the forced hot air source 302 and the forced cool air source 304, respectively, to a sample chamber 310. The ducts 306 and 308 are preferably corrugated black nylon tubing having a 2.5 cm diameter. The duct 306 is connected to the sample chamber 310 via a port 306A and the duct 308 is connected to the sample chamber 310 via a port 308A. A vent 312 and an exhaust fan 314 function to move air out of the sample chamber 310. Moreover, a means for shielding the interior of the sample chamber 310 from ambient light is integral with the sample chamber 310.

The temperature of the samples within the sample chamber 310 is preferably monitored by a tubular, metal-sheathed thermocouple 316, available from Idaho Technology of Idaho Falls, Id., model no. 1844, which is matched in thermal response to the samples held in the preferred sample containers, for example capillary tubes. Importantly, temperature homogeneity within the sample chamber 310 is achieved by mixing the air within the sample chamber 310. It is preferred that such mixing of the air within the sample camber 310 be carried out by a central sample chamber fan 318. The sample chamber fan preferably includes a 1.7×11 cm fan blade available from Idaho Technology, model no. 1862, and a motor available from Idaho Technology, model no. 1861, which creates air velocities of at least 800 to 1000-meters per minute within the sample chamber 310. Such rapid air velocities may not be needed in all applications of the present invention but rapid air velocities promote extensive mixing and temperature homogeneity within the sample chamber 310.

Within the sample chamber 310, a plurality of samples are held in capillary tubes, some of which are indicted at 320, and are placed in a vertical orientation on a rotatable carousel 322. The carousel 322 is preferably fourteen centimeters in diameter and rotated by a 400 step per revolution stepper motor 324 controlled by a micro stepping drive module 326. The stepper motor 324 is preferably one available from New England Affiliated Technologies of Lawrence, Mass., model no. 2198364, and the micro stepping drive module 326 is preferably one also available from New England Affiliated Technologies, model no. MDM7 micro stepping drive module, which provides 12,800 steps per rotation of the carousel 322.

Still referring to FIG. 11, a fluorescence excitation source 328 is provided. One preferred arrangement for the excitation path in accordance with the present invention will now be described with one preferred arrangement for the collection path in accordance with the present invention will subsequently be described. The fluorescence excitation source 328 preferably includes a 75 watt xenon arc source 328A focused with an elliptical reflector 328B. The xenon arc source 328A is preferably available from Photon Technology International of South Brunswick, N.J., model no. A1010, with f/2.5 elliptical reflector 328B. The power supply and other components needed to operate the fluorescence excitation source 328 are well known to those skilled in the art. Alternatively, a light emitting diode can be used as a fluorescence excitation source. Those skilled in the art will appreciate that many different excitation sources can be used within the scope of the present invention.

The radiation emitted by the fluorescence excitation source 328 is focused to about 2 mm using an adjustable iris 334 such as one available in the industry from Rolyn (Covina, Calif.), model no. 75.0125. The light emitted from the fluorescence excitation source 328 impinges upon a cold mirror 330, which is preferably available from Rolyn, model no. 60.4400, and passes through heat absorbing glass 332, which is preferably one available from Rolyn, model no. 65.3130. After collimation through a planoconvex lens 336, preferably one available from Rolyn, model no. 10.0260, a 450-490 nm bandpass interference filter 338, preferably one available from Omega Optical of Brattleboro, Vt., model no. 470RDF40, a focusing planoconvex lens 340, preferably available from Rolyn, model no. 10.0260, and a 1 mm silica window 342, preferably available from Omega, to prevent condensation on the just described optical components during temperature cycling. Using the described excitation path, a 5-7 mm section of one capillary sample tube 320A is illuminated.

Still referring to FIG. 11, the collection path for collecting the fluorescence emitted from the sample 320A will be described next. The optics of the collection path include a 1 mm silica window 344 which is placed in the optical path to prevent condensation on the other optical components. Two opposed aspheric lenses 346A&B, preferably available from Rolyn, model no. 17.1175, function to focus emitted fluorescence onto a 2×10 mm slit 348. The slit 348 can preferably be fabricated from cutting exposed X-ray film and the slit 348 functions as a spatial filter. After the slit 348 (acting as a spatial filter), the emitted fluorescence is imposed upon a 35 mm electronic shutter 350 operated via an electronic shutter control 352. The 35 mm electronic shutter 350 is preferably a Uniblitz shutter model no. VS35 and the electronic shutter control 352 is preferably driver model no. D122, both available from Vincent Associates of Rochester, N.Y. A collimating aspheric lens 354, preferably one available from Rolyn model no. 17.1175, is also provided.

A filter 356 is also included when detection of SYBR® Green I emissions is desired. The filter 356 is preferably a 520-580 nm band pass filter, available from Omega as model no. 550RDF60, which is preferably used for single wavelength acquisition. For detection of other emissions, for example, a combination of a dichroic filter 358 and wavelength filters 358A and 358B can be used. For example, for separation of fluorescein and rhodamine emissions, the dichroic filter 358 preferably consists of a 560 nm dichroic filter, preferably available from Omega, model no. 560 DRLP, and a 520-550 nm band pass filter (358A), preferably available from Omega, model no. 535DF30, for detection of fluorescein, and a 580-620 nm band pass filter (358B), preferably available from Omega, model no. 600DF40, for detection of rhodamine. For separation of fluorescein and Cy5 emissions, the dichroic filter 358 preferably is a 590 nm dichroic filter, available from Omega, model no. 590 DRLP, and filters 358A&B preferably consist of a 520-550 nm band pass filter (358A), available from Omega, model no. 535DF30, for detection of fluorescein, and a 660-680 nm band pass filter (358B), available from Omega, model no. 670DF20, for Cy5 detection. Those skilled in the art will readily appreciate that the use of other components can be readily implemented using the information set forth herein in order to accommodate other fluorescent wavelengths.

Still referring to FIG. 11, after being subjected to the respective filter 358A or 358B, the emitted fluorescence is focused through two planoconvex lenses 360A & 360B, each preferably available from Edmund of Barrington, N.J., model no. 32970, and onto photomultiplier tubes 362A and 362B, respectively. The photomultiplier tubes ("PMT") 362A and 362B are preferably available from Hamamatsu of Middlesex, N.J., model no. R928, and are each enclosed in a suitable housing including appropriate circuitry, preferably one available from Photon Technology International, model no. 714, with analog acquisition capabilities. A PMT and data acquisition control module 364 is also preferably provided. Manual PMT shutters 366A and 366B, as known in the art, are also provided.

The forgoing described optical components are preferably five centimeters in diameter and mounted in five centimeter universal lens mounts, such as those available from Rolyn, model no. 90.0190. As can be carried out by those skilled in the art, many of the necessary structural components were machined from black Delrin™ using techniques known in the industry.

Those skilled in the art will appreciate that the rapid temperature cycler with fluorescence detection 300 can advantageously be constructed using light emitting diodes (LEDs) and photodiodes in place of similarly functioning components represented in FIG. 11. Thus, the function of the fluorescence excitation source 328 can be carried out by light emitting diodes. The photomultiplier tubes 362A&B can also be replaced with photodiodes. Additional information regarding suitable light emitting diodes and photodiodes will be provided later herein. It will be appreciated that technique sensitivity is limited by background fluorescence, most of which comes from the probes, not the detection system. Significantly, stability is generally more important than absolute sensitivity.

Those versed in the art will appreciate that the rapid temperature cycler with fluorescence detection 300 represented in FIG. 11 includes the beneficial characteristics of a fluorimetry device with rapid temperature control, a combination nowhere suggested or taught in the art. PCR can be performed and analyzed during ten to twenty minutes of temperature cycling. The present invention's combination of 1) fluorescence monitoring within each temperature cycle and 2) analysis of the temperature and time dependence of hybridization provides advantages not otherwise obtainable.

The present invention also makes possible single-color fluorescence methods to monitor product purity and quantify template during PCR. Dyes that monitor DNA strand status are added to PCR reactions for observation during temperature cycling using embodiments of the present invention.

In order to explain some of the benefits which accrue with the present invention, specific examples using the apparatus represented in FIG. 11 will now be provided. DNA amplification was performed in 50 mM Tris, pH 8.3 (25° C.), 3 mM $MgCl_2$, 500 μg/ml bovine serum albumin, 0.5 μM of each primer, 0.2 mM of each deoxynucleoside triphosphate and 0.2 U of Taq polymerase per 5 μl sample unless otherwise stated in the following examples. Also in the following examples, human genomic DNA (denatured for 1 min by boiling) or purified amplification product was used as DNA template. Purified amplification product was obtained by phenol/chloroform extraction and ethanol precipitation (see D. M. Wallace 1987, Large- and small-scale phenol extractions and precipitation of nucleic acids (as described at p. 33-48, in S. L. Berger and A. R. Kimmel (Eds.), Guide to Molecular Cloning Techniques (Methods in Enzymology, Vol. 152) Academic Press, Orlando), followed by removal of primers by repeated washing through a Centricon 30 micro concentrator (available from Amicon of Danvers, Mass.). Template concentrations were determined by absorbence at 260 nm. $A_{260}/A_{280}$ ratios of templates were greater than 1.7.

In these examples, primers were synthesized by standard phosphoramidite chemistry, as known in the art, namely, using Pharmacia Biotech Gene Assembler Plus (Piscataway, N.J.). The 180 base pair fragment of the hepatitis B surface antigen gene was amplified using primers 5'-CGTGGTG-GACTTCTCTCAAT-3' (SEQ ID NO:1), and 5'-AGAA-GATGAGGCATAGCAGC-3' (SEQ ID NO:2)(Genbank sequence HVHEPB). SYBR® Green I dye was obtained from Molecular Probes (Eugene, Oreg.). The β-actin primers and fluorescein/rhodamine dual probe were obtained from Perkin Elmer (Foster City, Calif.) (no. N808-0230,). The human β-globin primers RS42/KM29 (536 base pairs) and PC03/PC04 (110 base pairs) are described in C. T. Wittwer, G. C. Fillmore and D. R. Hillyard, "Automated Polymerase Chain Reaction in Capillary Tubes with Hot Air," *Nucl. Acids. Res.* 17:4353-4357 which is now incorporated herein by reference. The single labeled probes:

5'-CAAACAGACACCATGGTGCACCTGACTC-CTGAGGA-fluorescein-3' (SEQ ID NO:3) and

5'-Cy5-AAGTCTGCCGTTACTGCCCT-GTGGGGCAAG-phosphate-3' (SEQ ID NO:4)

were synthesized using a fluorescein phosphoramidite (available from Glen Research of Sterling, Va., no. 10-1963) a Cy5™ phosphoramidite (available from Pharmacia no. 27-1801-02), and a chemical phosphorylation reagent (available from Glen Research no. 10-1900). These adjacent probes hybridize internal to the PC03/PC04 β-globin primer pair on the same DNA strand and are separated by one base pair. Probes were purified by reverse phase C-18 high pressure liquid chromatography and homogeneity checked by polyacrylamide electrophoresis and absorbance ($A_{260}$ and the absorbance maximum of the fluorophore). Hybridization probes (β-actin and β-globin) were used at 0.2 μM each.

In the pertinent examples described herein, amplification samples of 5 μl were loaded into capillary sample tubes, some of which are represented in FIG. 11 at 320. The preferred capillary sample tubes are those available from Idaho Technology, model no. 1705, having dimensions of 1.02 mm O.D. and 0.56 mm I.D. Once loaded, the capillary sample tubes were sealed with a butane flame. The surface of the capillary sample tube was cleaned with optical grade methanol before it was loaded into the carousel 322 of the rapid temperature cycler with fluorescence detection 300.

Control of the components represented in FIG. 11 was achieved by use of a graphical programming language known as LabView (available from National Instruments, Austin, Tex.) and a 12-bit multifunction input/output card 368A (available from National Instruments under the designation AT-MIO-E2) in a PC compatible computer 368 utilizing an Intel® 80486 microprocessor running at a clock speed of 120 MHZ. Analog output channels on the input/output card 368A were used to control the sensitivity, i.e. the PMT voltage, of each of the photomultiplier tubes 362A&B. Analog input channels on the input/output card 368A receive the signals from each of the photomultiplier tubes 362A&B. The PC compatible computer 368, through the input/output card 368A, controls the position, rate and direction of movement of the carousel 322. For example, when multiple capillary sample tubes are loaded, the carousel 322 rapidly positions each capillary sample tube 320 sequentially at a monitoring location (the location represented by capillary sample tube 320A) for a 10-100 msec acquisition period. For continuous monitoring of a single capillary sample tube, the capillary sample tube is held in the monitoring position while data is preferably acquired every 200 msec. and is averaged in accordance with well-known techniques. Time, temperature, and preferably two channels of fluorescence are continuously displayed via a monitor 368B associated with the computer 368 as fluorescence vs. cycle number and fluorescence vs. temperature plots.

The carousel 322 should be positioned where maximal fluorescence and signals are acquired. When a single capillary sample tube, such as the capillary sample tube 320A, is monitored the signals are acquired every 200 msec with an integrating time constant set on the photomultiplier tube 362A or 362B, or both, at 50 msec. For multiple sample tubes, the time constant is set at 0.5 msec and the carousel is rotated once to locate the precise position where each capillary sample tube 320 provides the maximum fluorescence in each of the two channels. After positioning the capillary sample tube 320A at a location where maximum fluorescence is obtained, the sensitivity of each PMT 362A&B is adjusted and the carousel rotated again to count and locate the position of all the capillary sample tubes 320 in the carousel 322. When only a signal fluorescence acquisition is desired once each amplification cycle during extension, each capillary sample tube 320 is sequentially positioned on the carousel 322 at the monitoring position for 100 msec. Continous acquisition for multiple tubes can also be obtained by continuously rotating the carousel 322. Temperature control programming was based upon, and modified from, a commercial rapid temperature cycler available from Idaho Technology under the trademark Rapidcycler™ using an 8051 cross compiler available from Systronics, Salt Lake City, Utah, designated BCI51 and Dallas development system (also available from Systronics under the designation DPB2).

Figure 11A:
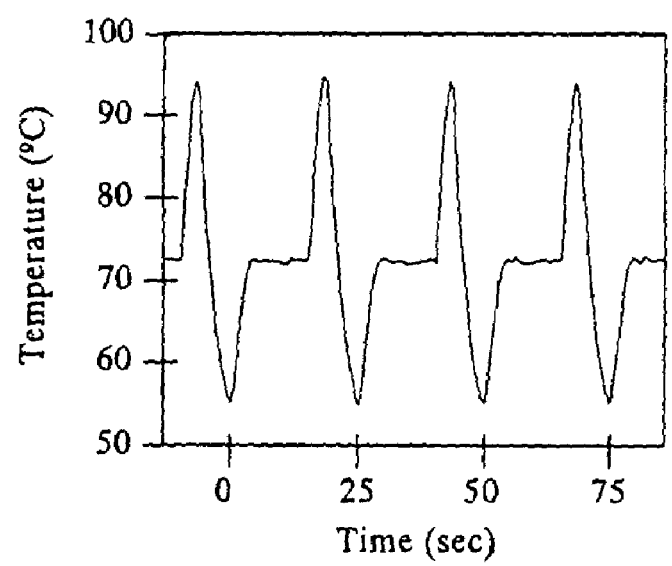
FIG. 11A is a temperature v. time chart of showing one preferred operation of the apparatus of FIG. 11.

In practice, the temperature response of the rapid temperature cycler with fluorescence detection 300 is similar to the response obtained with the embodiment of the present invention disclosed in FIGS. 8A&B allowing 20-30 second cycles (30 cycles in 10-15 min) as represented in the temperature vs. time chart of FIG. 11A (which shows a few cycles of one preferred temperature profile). When a double strand-specific fluorescent dye is present during amplification, fluorescence generally increases as more double stranded product is made. See R. Higuchi, G. Dollinger, P. S. Walsh, and R. Griffith, 1992, "Simultaneous Amplification and Detection of Specific DNA Sequences," *Bio/Technology* 10:413-417.

Moreover, it will also be appreciated that double strand specific dyes such as ethidium bromide or SYBR® Green I can be used as generic indicators of amplification. SYBR® Green I dye is preferred over ethidium bromide in many applications because it has an excitation maximum near fluorescein and often provides a stronger signal with DNA than visible excitation of ethidium bromide.

Fluorescence also depends on temperature, a confounding effect during temperature cycling that is usually eliminated by considering fluorescence once per cycle at a constant extension temperature. However, if temperature, time, and fluorescence are acquired every 200 msec during rapid cycle amplification, a three dimensional spiral is shown on the monitor 368B as represented in FIG. 12. The three dimensional plot represented in FIG. 12 is also projected in FIG. 12A as a two dimensional plot of temperature vs. time, projected in FIG. 12B as a two dimensional plot of fluorescence vs. time, and projected in FIG. 12C as fluorescence vs. temperature. The temperature vs. time projection of FIG. 12A repeats each cycle and provides essentially the same information as set forth in FIG. 11A. Because fluorescence varies inversely with temperature, the fluorescence vs. time projection shown in FIG. 12B at early cycles is a scaled mirror image of the temperature vs. time plot. As product accumulates, the fluorescence increases at all temperatures where double stranded product is present. However at denaturation temperatures, fluorescence returns to baseline since only single stranded DNA is present.

Figure 12C:
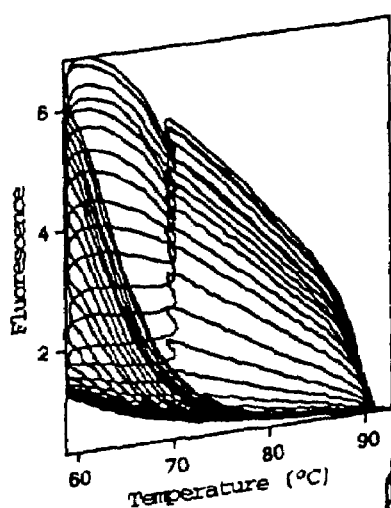
FIGS. 12A-C are representations of two dimensional plots of temperature vs. time, fluorescence vs. time, and fluorescence vs. temperature which are together shown as a three dimensional plot in FIG. 12.
Figure 12:
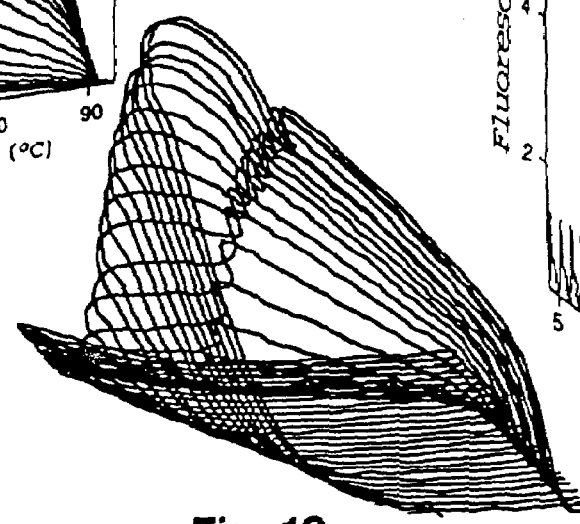
FIG. 12 is a representation of three dimensional plots of temperature, time, and fluorescence during amplification of a hepatitis B DNA fragment in the presence of SYBR Green I.
Figure 12B:
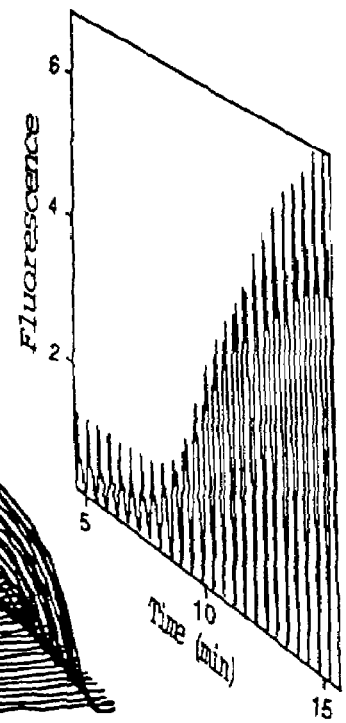
Figure 12A:
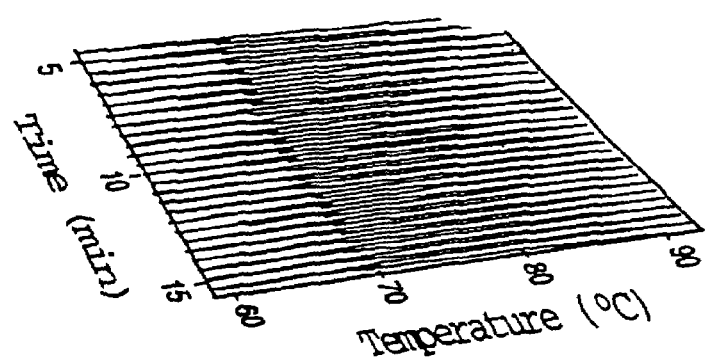

The fluorescence vs. temperature projection of double stranded dyes shown in FIG. 12C eliminates the time axis and shows the temperature dependence of strand status during DNA amplification. The fluorescence vs. temperature projection shown in FIG. 12C is for a 180 base pair fragment of hepatitis B virus DNA.

Figure 13:
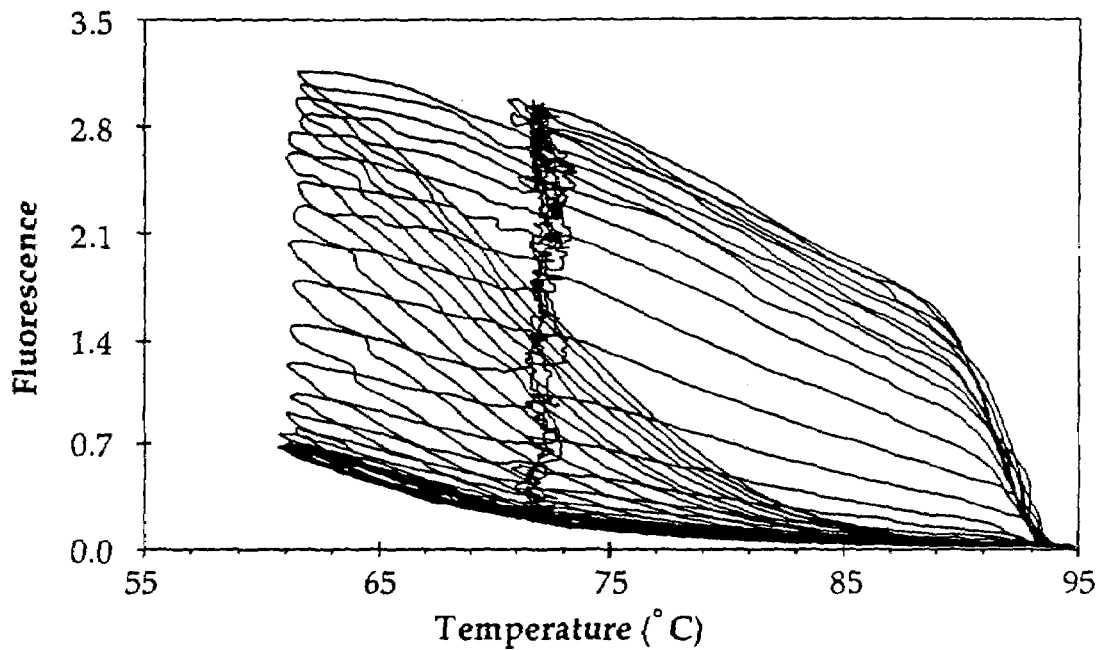
FIG. 13 is a fluorescence vs. temperature projection during the amplification of a 536 base pair fragment of the human β-globin gene in the presence of SYBR Green I.

Another fluorescence vs. temperature projection is shown in FIG. 13. The projection represented in FIG. 13 is for a 536 base pair fragment of human β-globin DNA. Early cycles represented in FIG. 13 appear identical, with a nonlinear increase in fluorescence at lower temperatures. As amplification proceeds, later cycles appear as rising loops between annealing and denaturation temperatures that show significant hysteresis. That is, the observed fluorescence during heating is greater than that during cooling. As the sample is heated, fluorescence is high until denaturation occurs (apparent as a sharp drop in fluorescence). As can be seen in FIG. 13, as the sample cools from denaturation to annealing temperatures, double strand signal increases rapidly. Also as can be seen in FIG. 13, the fluorescence continues to increase during extension while the temperature is held constant.

Figure 26:
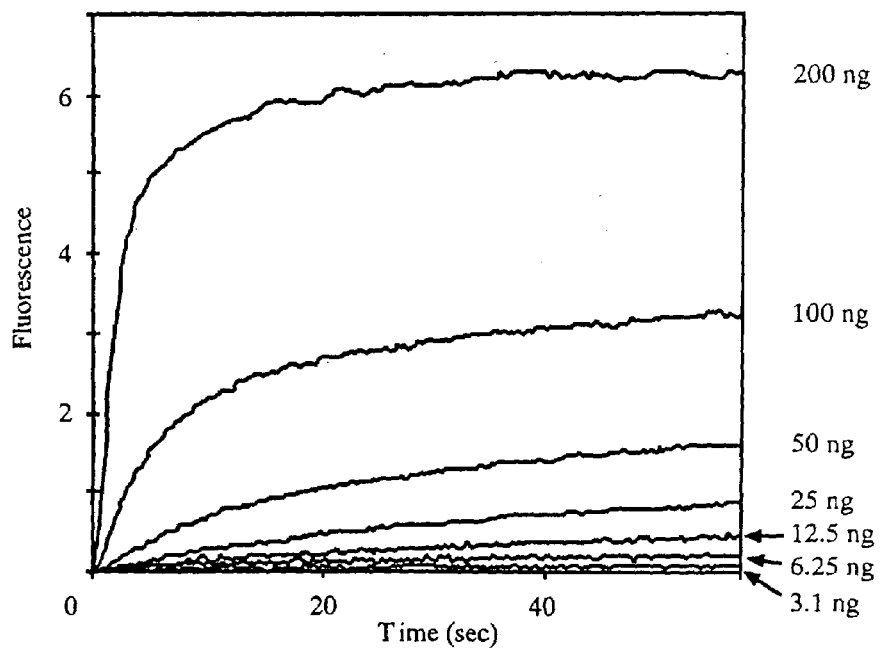
FIG. 26 is a plot of fluorescence vs. time showing product annealing for different concentrations of PCR product in the presence of SYBR Green 1.

Double strand specific dyes can also be used in accordance with various aspects of the present invention. The strand status of PCR products can be followed with dyes that fluoresce in the presence of dsDNA. When SYBR® Green I is present during amplification, fluorescence increases as more dsDNA is made. However, temperature cycling introduces a confounding effect because fluorescence is inversely proportional to temperature as shown in FIGS. 26A and 26B. As product accumulates, the fluorescence increases except at denaturation temperatures, where the fluorescence returns to baseline as shown in FIG. 12C.

Figure 14:
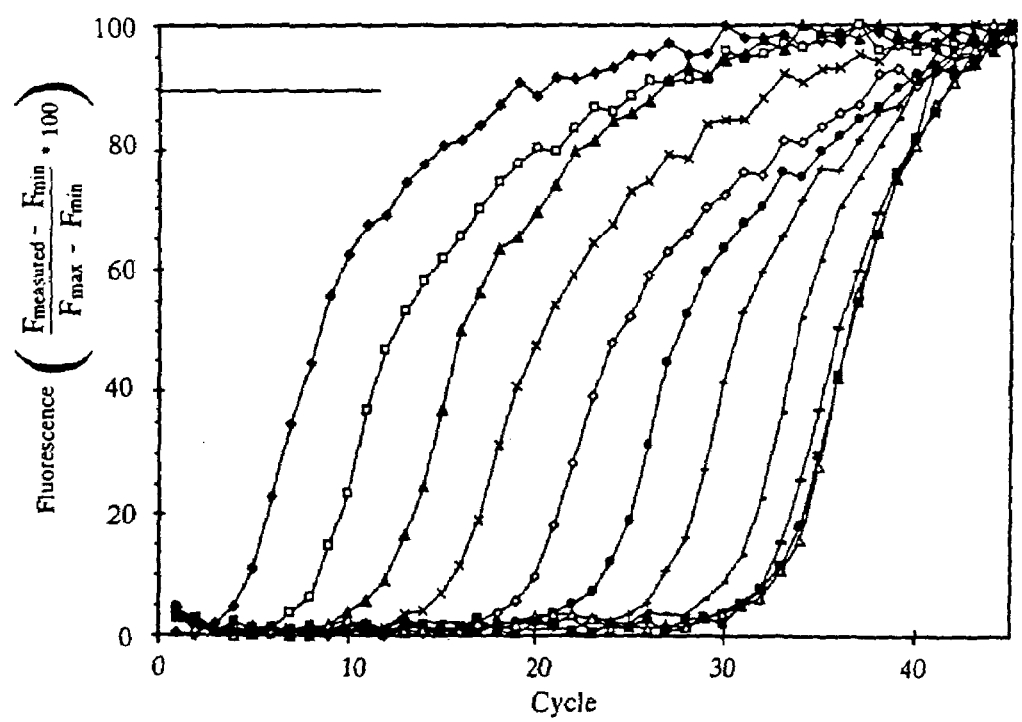
FIG. 14 is a cycle number vs. fluorescence plot obtained in accordance with an aspect of the present invention.
Figures 14A, 15:
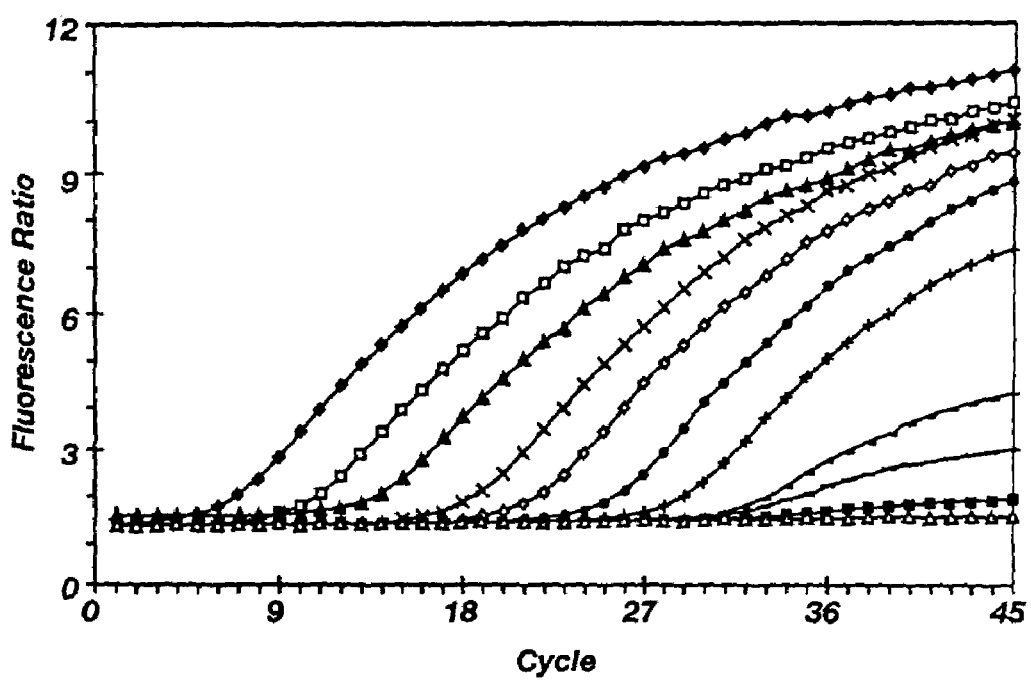
FIG. 14A provides a legend for FIG. 14, and subsequent figures, indicating different initial template copy numbers.
FIG. 15 is a cycle number vs. fluorescence ratio plot obtained in accordance with an aspect of the present invention.

When multiple samples are monitored, using the rapid temperature cycler with fluorescence detection 300, once each cycle with SYBR® Green I, a $10^7$-$10^8$ range of initial template concentration can be discerned as represented in FIG. 14. FIG. 14A provides a legend for the indicia provided on the different plots in FIG. 14, and subsequent figures, for different initial template copy number. When the data are normalized as the percent maximal fluorescence of each capillary sample tube 320, one hundred initial copies are clearly separated from ten copies. However, the difference between one and ten copies is marginal, and no difference is observed between zero and one average copies per capillary sample tube 320.

Double strand dyes depend on the specificity inherent in the amplification primers. As will be appreciated by those skilled in the art, nonspecific amplification at high cycle numbers can limit detection sensitivity to about one hundred initial template copies (see FIG. 14). With rapid cycling taught by the present invention, further improvements in amplification specificity are obtained further improving the overall DNA amplification performance.

Quantification with sequence-specific probes has a similar dynamic range as double stranded DNA dyes but, as shown in the plots of FIGS. 15A and 15B, appear to discriminate even a single initial template copy from negative controls.

When low copy number detection and quantification are needed, additional specificity is provided by fluorescent probes that require hybridization for signal generation. Cleavage of a dual-labeled exonuclease probe is one technique which is capable of distinguishing a single template copy from a negative control as shown by FIG. 15. FIG. 15 show plots of fluorescence ratio vs. cycle number for different initial template copy number, according to the legend provided in FIG. 14A.

Signal generation with 5'-exonuclease probes is dependent not only on DNA synthesis, but requires hybridization and hydrolysis between the fluorophores of the dual-labeled probe. This hydrolysis reduces quenching and the fluorescence ratio of fluorescein to rhodamine emission increases. For more information on this technique, see L. G. Lee, C. R. Connell and W. Bloch, 1993, "Allelic Discrimination by Nick-translation PCR with Fluorogenic Probes," *Nucl. Acids Res.* 21:3761-3766 & Livak, K. J., S. J. A. Flood, J. Marmaro, W. Giusti and K. Deetz, 1995, "Oligonucleotides with Fluorescent Dyes at Opposite Ends Provide a Quenched Probe System Useful for Detecting PCR Product and Nucleic Acid Hybridization," *PCR Meth. Appl.* 4:357-362).

Figure 25:
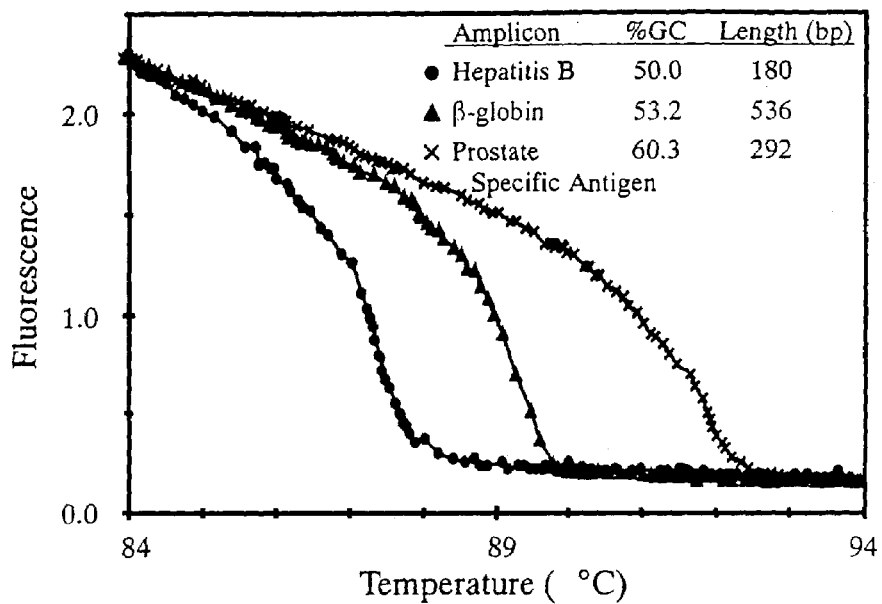
FIG. 25 is a plot of fluorescence vs. temperature for three different PCR products in the presence of SYBR Green 1 acquired during a 0.2 degree per second temperature transition through the product melting temperatures.

FIG. 25 shows fluorescence PCR results from a probe with five intervening bases between fluorescein and rhodamine labels. The forty-five cycle amplification was completed in 20 minutes using the rapid temperature cycler with fluorescence detection 300 of FIG. 11. By monitoring the fluorescence ratio once per cycle, a $10^9$ fold range of initial template concentration could be distinguished. The amplification curves are shifted approximately 3-4 cycles for each 10-fold change in initial template concentration.

Although the final fluorescence signal is decreased when low copy numbers are amplified (presumably because of decreased amplification efficiency), quantification between zero and one hundred copies is readily possible. The signal generated by exonuclease probes is cumulative and only indirectly related to product concentration. Hence, the fluorescence signal continues to increase even after the amount of product has reached a plateau. Using the information contained herein, those skilled in the art can formulate appropriate standards to control for efficiency of amplification and cleavage in order to carry out absolute quantification.

Figure 16:
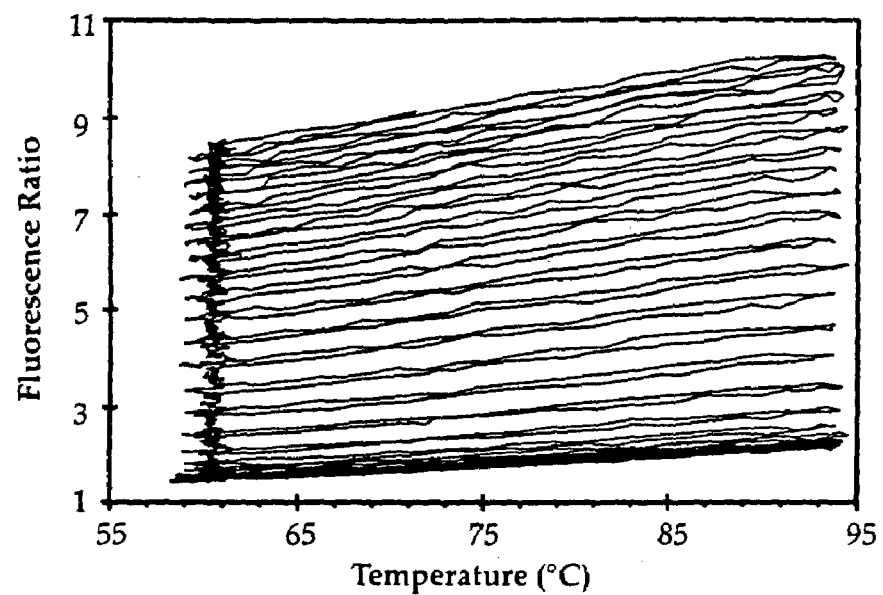
FIG. 16 is a fluorescence ratio vs. temperature plot obtained in accordance with one aspect of the present invention.

Fluorescence vs. temperature plots of 5'-exonuclease probes confirm that probe hydrolysis is the mechanism of signal generation. In FIG. 16, a fluorescence vs. temperature plot of two-temperature cycling is shown with the β-actin exonuclease probe. In each cycle the fluorescence ratio varies linearly with temperature and there is little, if any, hysteresis. The signal increases each cycle during the annealing/extension phase when probe hydrolysis occurs. Although the fluorescence of both fluorescein and rhodamine decreases with increasing temperature (data not shown in the figures), the rate of change is greater for rhodamine, resulting in an increasing ratio with increasing temperature. No temperature-dependent hybridization effects are apparent with the 5'-exonuclease probe.

Figure 17:
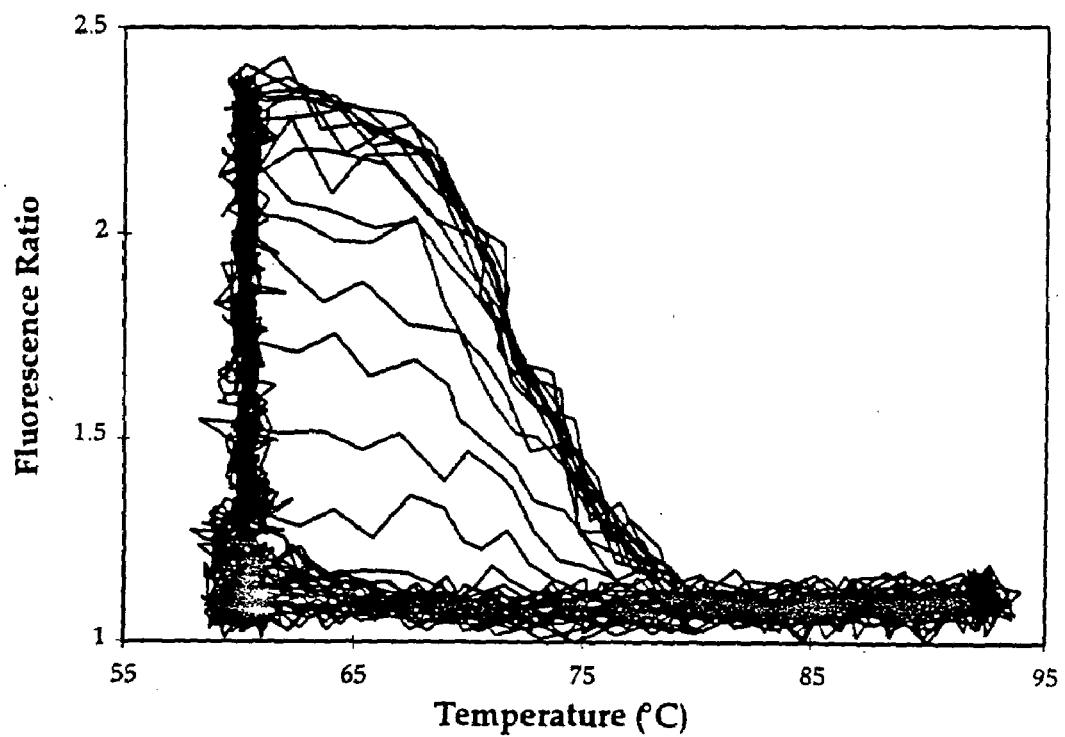
FIG. 17 is a fluorescence ratio vs. temperature plot obtained in accordance with one aspect of the present invention.

In contrast, when the fluorescence signal is dependent only on hybridization, fluorescence ratio vs. temperature plots show a different pattern with hysteresis during two-temperature cycling, as plotted in FIG. 17. The plots in FIG. 17 represent the results obtained using two adjacent hybridization probes which are present, an upstream probe labeled 3' with fluorescein and a downstream probe labeled 5' with Cy5™. The probes are separated by a 1 base pair gap. During the annealing/extension phase of the reaction, the probes hybridize resulting in accumulating product and the Cy5™ to fluorescein fluorescence ratio increasing. During heating to product denaturation temperatures, the probes dissociate between 65° C. and 75° C., returning the fluorescence ratio to background levels. The change in fluorescence ratio during hybridization is largely due to an increase in Cy5™ fluorescence from resonance energy transfer. The temperature dependence of hybridization can be used to detect mutations by a shift in the melting curve. Adjacent hybridization probes are also very useful for quantification, as shown in FIG. 15B.

From the foregoing discussion, it will be appreciated that fluorescence monitoring during DNA amplification is an extraordinarily powerful analytical technique. Using the rapid temperature cycler with fluorescence detection 300, productive and cost efficient real time monitoring, sequence-specific detection, and quantification can be achieved in five to twenty minutes, depending on the number of initial template copies present.

Furthermore, the system and results represented in FIGS. 11-17 is particularly suited for continuous monitoring of a biological reaction using fluorescent dyes. For example, with precise temperature control and double-strand-specific dyes, product purity can be estimated by melting curves. With rapid temperature control provided by the present invention, absolute product concentration can be determined by reannealing kinetics. The present invention advantageously provides rapid temperature changes and strict intra-sample temperature homogeneity which is not available in the prior art. In contrast to the prior art, the present invention utilizes sample containers with a high surface area to volume ratio, (for example by using the preferred capillary sample tubes 320 in FIG. 11) and uses air as the thermal transfer medium providing rapid control of sample temperature not otherwise obtainable. For example, sample temperature vs. time plots obtained when processing samples in the sample containers of the present invention show sharp spikes at denaturation and annealing temperatures (showing rapid temperature response) in contrast to the prior art conical plastic tubes which require several seconds for all of the sample to reach thermal equilibrium. Moreover, the sample containers of the present invention provide improved results over using etched silicon or glass chips as sample containers since the thermal cycle times and thermal homogeneity of the present invention are superior than the thermal cycle times and thermal homogeneity possible using such other structures.

Using the present invention, many aspects of DNA amplification which have heretofore been little understood are discernable. For example, product denaturation occurs in less than one second, yet the prior art calls for ten seconds to one minute of denaturation. Observing product melting by real time fluorescence monitoring with double strand dyes in accordance with the present invention (see FIGS. 12 and 13) shows that use of shorter denaturation times is very effective. As another example, many causes of the known "plateau effect" have been proposed, but few data are available to distinguish between alternatives. As shown in FIG. 13, product reannealing is very rapid. In fact, during later cycles of amplification, a majority of product is reannealed each cycle during cooling before the primer annealing temperature is reached. This occurs with cooling rates of 5-10° C./second carried out by the present invention. Product reannealing with slower, prior art temperature cyclers will even be greater because more time is required to transition between denaturation and annealing temperature. This undesirable effect limits product yield, and is a major cause of the "plateau effect" known in the art.

Furthermore, the present invention provides an inexpensive instrument that can be used in commercial applications and that continuously monitors fluorescence during rapid cycle amplification. The thermal cycler of the present invention is capable of carrying out DNA amplification in no more than 10-20 minutes and the optical and detection components of the present invention discern one, two, three, or more fluorophores. The preferred embodiments of the present invention monitor a number of individual samples, for example, 24 samples (capillary sample tubes 320 in FIG. 11) from once every few seconds, preferably once a second, and more preferably ten times each second.

It is within the scope of the present invention to prepare samples for processing using the known ninety-six well apparatus and the capillary sample tubes 320 which are then placed in one of the preferred embodiments of the present invention, for example, the rapid temperature cycler with fluorescence detection (300 in FIG. 11), for thermal cycling and analysis.

Advantageously, preferred embodiments of the present invention utilize fluorescence feedback for real time control and optimization of the biological process, for example DNA amplification, as the process is ongoing. Thus, with the preferred embodiments disclosed herein, the fluorescence which is detected is used to control temperature cycling. Using embodiments of the present invention disclosed herein, and using the preferred continuous monitoring techniques with dsDNA-specific dyes, extension will be terminated each thermal cycle after the detected fluorescence stops increasing. Further, in accordance with the present invention, denaturation conditions are also controlled by increasing the temperature only until the product is completely melted. Still further, in accordance with the present invention, primer annealing is monitored with resonance energy transfer between fluorescein and Cy5-labeled oligonucleotides. Moreover, using the present invention, temperature cycling of the sample is automatically terminated after a predetermined amount of product has been made.

In accordance with the present invention and as is possible using the apparatus of the present invention, rapid temperature cycling with minimal annealing and denaturation times improves quantitative PCR and increases the discrimination of allele specific amplification. Rapid cycling for cycle sequencing reduces sequencing ambiguities and minimizes "shadow banding" in dinucleotide repeat amplifications. In accordance with the present invention, for long PCR up to 35 kb, yield is improved when the sample is exposed as little as possible to high denaturation temperatures.

Figure 18A:
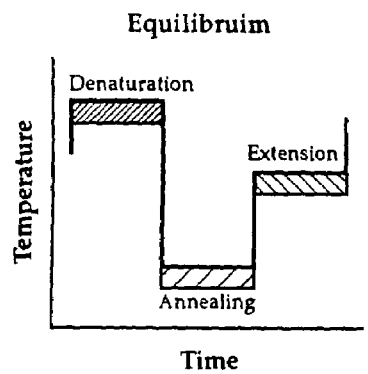
FIG. 18A is a graph representing an equilibrium PCR paradigm.
Figure 18B:
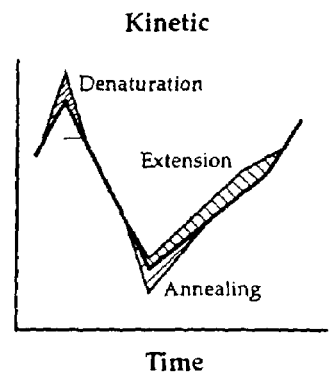
FIG. 18B is a graph representing a kinetic PCR paradigm.
Figure 18C:
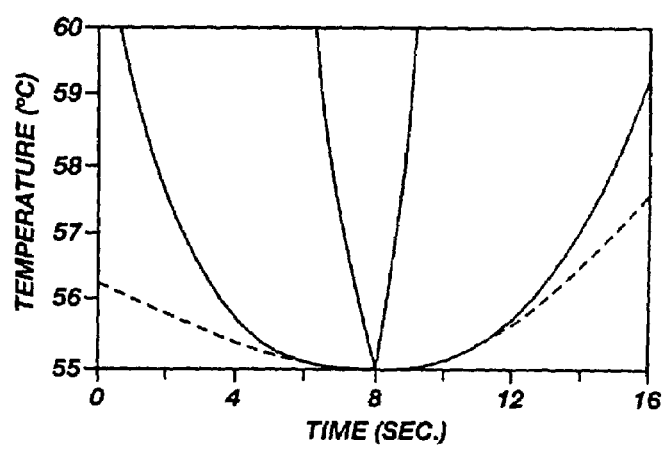
FIG. 18C is a graph representing different time/temperature profiles near an annealing temperature.

In contrast to the previous approach to PCR which treat PCR as three reactions, denaturation, annealing, extension, each of which occur at three different temperatures (as represented in FIG. 18A), one aspect of the present invention provides that a kinetic paradigm for PCR renders important improvements. Using a kinetic paradigm for PCR (as represented in FIG. 18B), the temperature vs. time curve consists of continuous transitions between overlapping reactions. The method and apparatus of the present invention is particularly efficient at carrying out PCR under the kinetic paradigm. FIG. 18C is a graph representing different time/temperature profiles near an annealing temperature of 55° C. In FIG. 18C, the solid trace shows a centrally positioned "spike" representing the temperature of response of a 10 μl sample. In contrast, the traces shown as short and long line segments in FIG. 18C represent the temperature responses of samples obtained using heat block instruments. As can be seen from FIG. 18C, the embodiments of the present invention produce annealing segment "spikes," with the advantages discussed herein, in contrast to the temperatures "plateaus" according to the conventional wisdom in the art.

The previously available instrumentation used for detection presented many drawbacks. Rapid, precise temperature cycling is provided by the system of the present invention described herein, in contrast to previously available instrumentation that is five to ten times slower. With the continuous fluorescence monitoring also provided by the system of the present invention, the temperature dependence of hybridization can be followed. By following hybridization during temperature cycling, the number of probes and/or spectral colors required can be minimized. That is, different products and mutations can be detected by their dynamic melting characteristics, rather than going to the trouble of synthesizing different fluorophore-labeled probes for each DNA species that is to be detected.

In order to provide an embodiment of the present invention that is most cost effective, a high intensity light emitting diode is used instead of a xenon arc source or a laser for sample illumination, and photodiodes are used for detection. Samples are loaded into glass capillary sample tubes, or alternatively into composite glass/plastic sample containers (see FIG. 21A-D) in a 96-well format that does not require heat sealing. The present invention thus provides real time fluorescence analysis in a cost effective manner. Real time fluorescence control of temperature cycling improves amplification quality. For example, if the temperature of samples is increased only until denaturation occurs, product exposure to high temperatures is minimized. This increases yield by limiting product and enzyme degradation and increases specificity by limiting amplification of products with a high melting temperature.

Reference will next be made to FIG. 19, which provides a diagrammatic representation of another preferred embodiment of the present invention configured for continuous monitoring of a single sample. It will be understood, however, that the structures represented in FIGS. 19 and 20 can also be incorporated into a system which automatically processes multiple samples, such as the apparatus represented in FIG. 11 and as will be explained shortly herein. In the embodiment of FIG. 19, a single sample holder 402 is placed in a holding bracket 404 positioned at the intersection of a temperature-controlled air stream and a linear optical path. The sample holder 402 includes a tube 402A which has many of the desirable characteristics of a capillary tube. In accordance with the present invention, different configurations of capillary tubes can be used and the tube 402A preferably has a rectangular cross section. The biological sample preferably is held at a bottom end of the tube 402A as indicated at 402B. A cap 402C is also preferably provided on the sample holder 402.

Reference will next be made to FIGS. 19A-19E which compare the effect of different configurations of sample containers on the temperature response of the sample itself. The temperature-time tracings shown in FIG. 19E correspond to the response obtained using the sample container configurations represented in FIGS. 19A-C, respectively. FIG. 19D represents a sample container which is less preferred for use in the present invention and is included for comparison. Using the information set forth herein, those skilled in the art can arrive at optimum sample container configurations for particular applications of the present invention. Further information regarding each of the sample container configurations represented in FIGS. 19A-D are set forth below.

| Figure | Surface Area (mm²/10 μl) | Fluid Column Length (mm) | Sample Volume | Source |
|---|---|---|---|---|
| 19A | 77 | 47 | 10 μl | Kimble KIMAX #46485-1 |
| 19B | 42 | 13.8 | 34 μl | Kimble KIMAX #46485-15 |
| 19C | 32 | 8 | 59 μl | Kimble KIMAX #34500-99 |
| 19D | 18 | N/A | 10 μl | MICRO-AMP ™ tube of Perkin-Elmer Cetus GeneAmp PCR System 9600 |

In the apparatus of FIG. 19, an excitation radiation source 418, preferably an LED and most preferably a blue LED, is provided to illuminate the sample holder 402. The radiation emitted by the excitation radiation source 418 passes through aspheric focusing lenses 420 and an excitation bandpass filter 422 and the radiation is focused onto the sample holder 402.

The optical components illustrated in FIG. 19 are preferably held in an optical housing 412. A housing 406 is also provided. A fan 408 is provided to move air through an air duct 414 and over the sample holder 402 held in the sample bracket 404. A temperature unit 410 is placed in the air flow path to provide heating or heating and cooling for the air passing over the sample holder 404. A nozzle 416 effectively directs the air over the sample holder 404.

The emissions which are given off by the sample pass through two more aspheric lenses 420 and an emission bandpass filter 424 and are received by a photo detector 426, which preferably is a photo diode. Those skilled in the art can readily provide the control components needed to advantageously operate the apparatus represented in FIG. 19 using the information set forth herein.

Figure 19F:
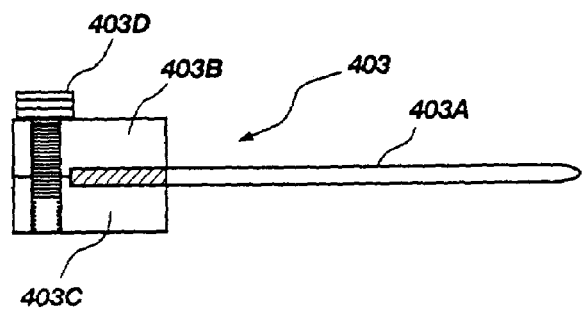
FIGS. 19F and 19G are side and end views, respectively, of one preferred sample container in accordance with the present invention.
Figure 19G:
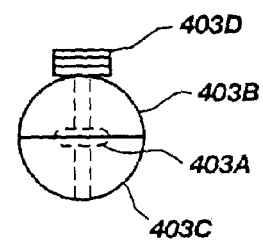

FIGS. 19F and 19G are side and end views, respectively, of one preferred sample container 403 which utilizes a rectangular capillary tube 403A. The capillary tube 403A is preferably one available from Vitro Dynamics Inc. having dimensions of 1 mm×3 mm×50 mm. A first cap member 403B and a second cap member 403C are held together by a screw 403D, the screw 403D also functioning as a holder for the capillary tube 403A.

Figure 19H:
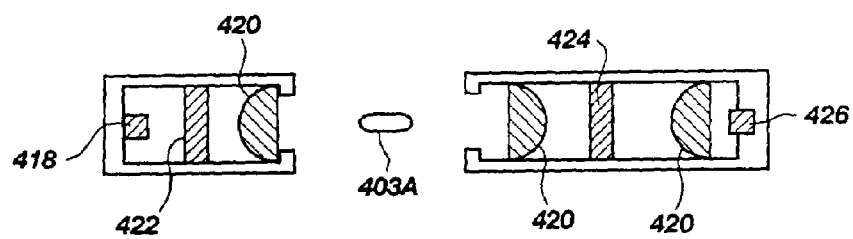
FIGS. 19H and 19I, respectively, show two possible orientations of a rectangular capillary tube when detecting fluorescence of the sample.
Figure 19I:
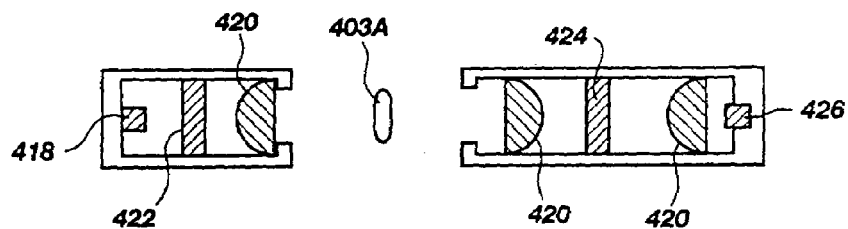

FIGS. 19H and 19I, respectively, show two possible orientations of a rectangular capillary tube 403A when detecting fluorescence of the sample contained therein. FIG. 19H shows the rectangular capillary tube 403A oriented so that its edges are in line with the optical axis of the excitation and detection optics ("edge excitation and detection"). FIG. 19I shows the rectangular capillary tube 403A oriented so that its faces are in line with the optical axis of the excitation and detection optics ("face excitation and detection"). Surprisingly, the fluorescence signal obtained from the edge detection orientation shown in FIG. 19H is about three-fold to about five-fold higher than obtained with the face detection orientation shown in FIG. 19I. The desirable characteristics of using the edge detection orientation shown in FIG. 19H is at least partially due to total internal reflection which takes place in the capillary tube 403A which concentrates the fluorescence signal to the extremities of the capillary tube 403A.

Figure 20:
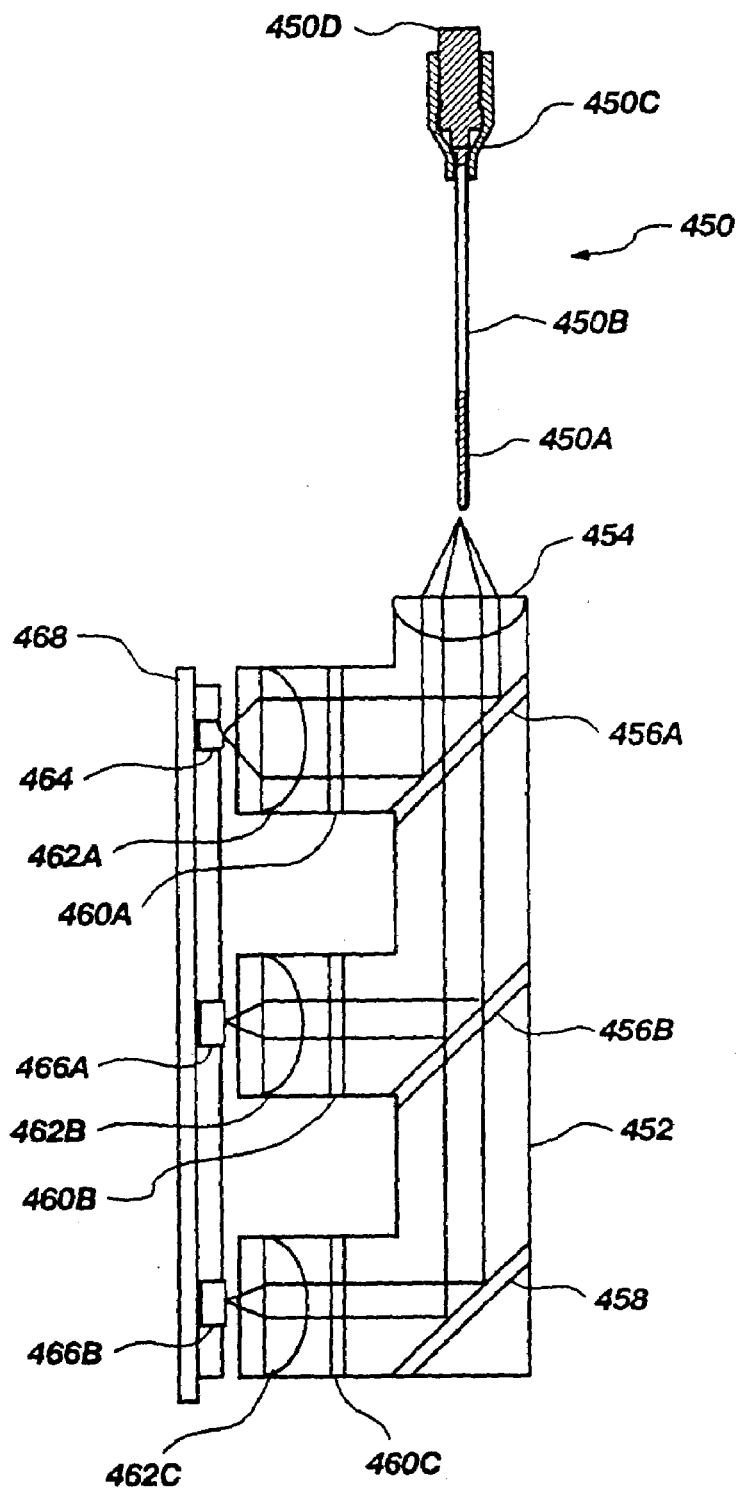
FIG. 20 shows the optical layout of another preferred embodiment in accordance with the present invention to provide continuous monitoring of a sample undergoing DNA amplification.

FIG. 20 shows the optical components of another preferred embodiment in accordance with another aspect of the present invention. The optical components represented in FIG. 20 are preferably incorporated into the thermal cycling and sample handling structures represented in FIG. 21, which will be more fully described shortly, but which can also be used with many different arrangements to provide monitoring (most preferably continuous monitoring) of a sample undergoing the polymerase chain reaction.

Figure 21:
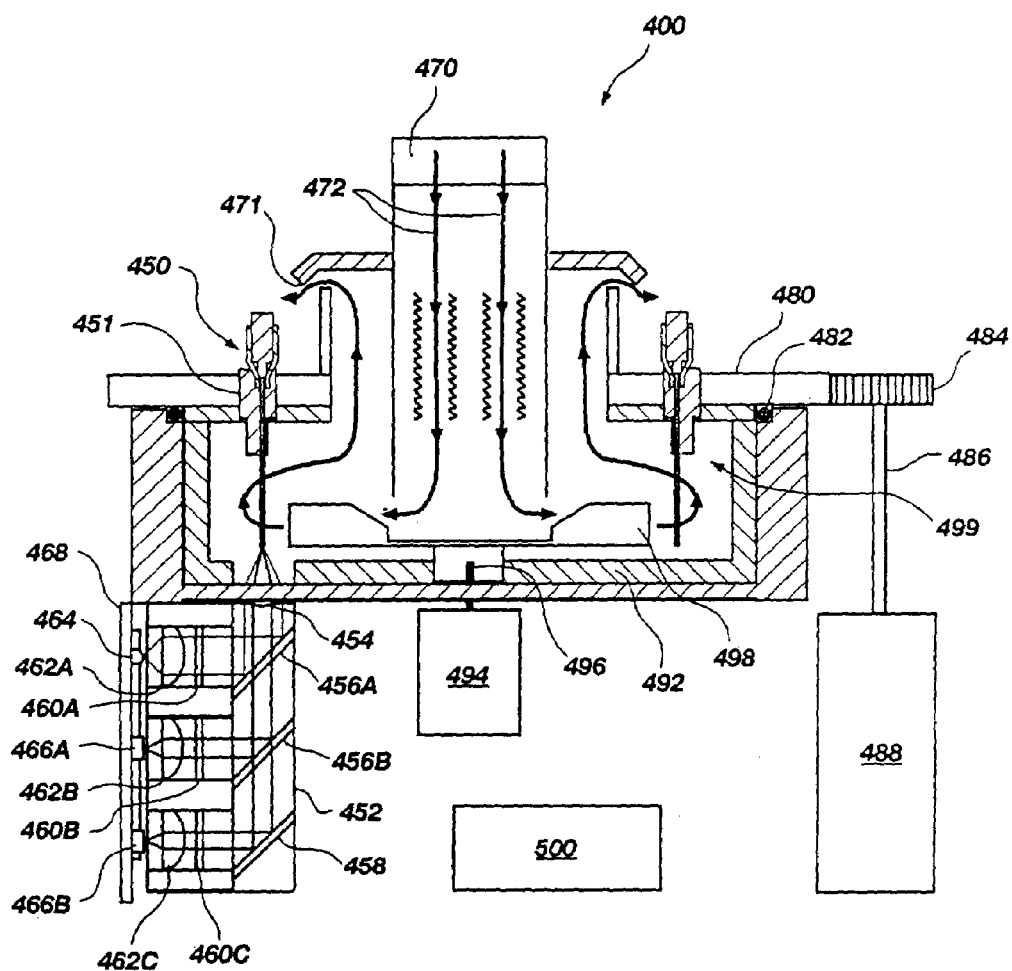
FIG. 21 is a schematic representation of another embodiment of the present invention which is a rapid temperature cycler with fluorescence detection at the tip of the sample containers.

In contrast to the arrangements previously disclosed herein, the optical excitation and detection paths are combined in the embodiment of FIGS. 20 and 21, referred to herein as an epifluorescent path, rather than a linear path. In the embodiment of FIGS. 20 and 21, the excitation and emission radiation follow the same optical path between the capillary tube and the dichroic element used in the excitation path. A capillary tube is particularly adapted for use in the embodiment of FIGS. 20 and 21 due to the total internal reflection (also referred to as "light piping") along the length of the capillary sample tube which is exploited to increase both excitation and emission intensities.

In the embodiment of FIGS. 20 and 21, to accommodate maximal light piping, the optical axis is parallel to the length of the capillary tube (paraxial) with the tip of the capillary tube positioned at the focal point. Assuming a refractive index of about 1.33 for the sample being detected, about 12.3% of emitted light is guided to the tip. It is understood that centrifuge action can be used to move the sample to the tip of the capillary tube.

Figure 22:
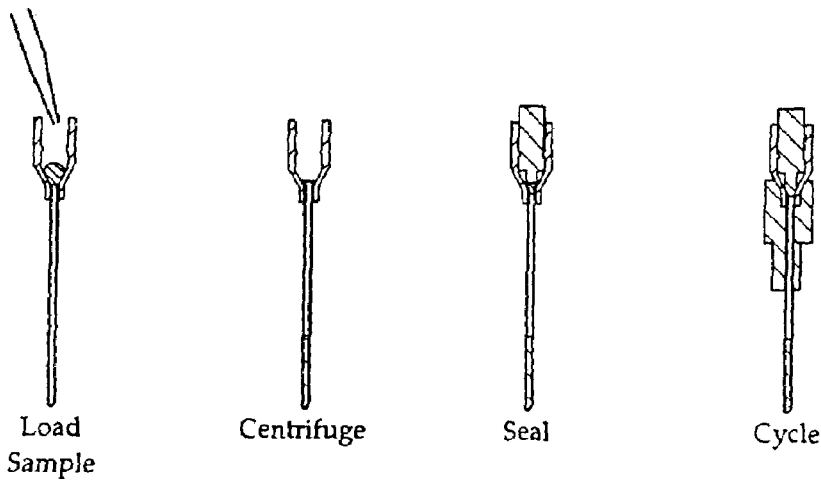
FIG. 22 illustrates useful temperature vs. time segments for fluorescence hybridization monitoring.
Figure 22:
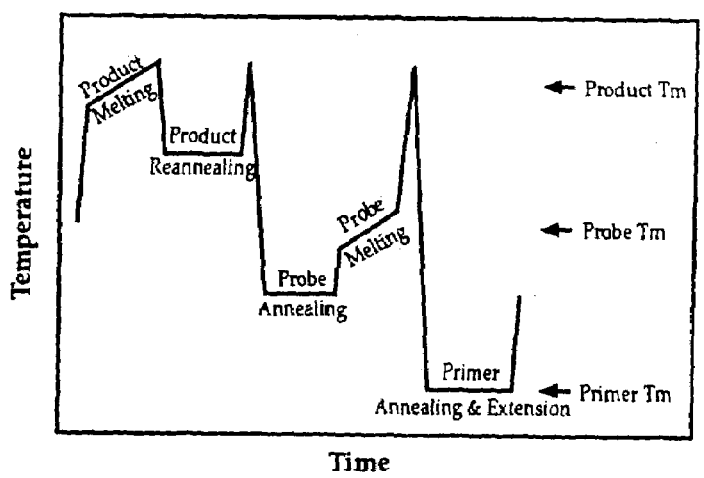
Figure 22A:
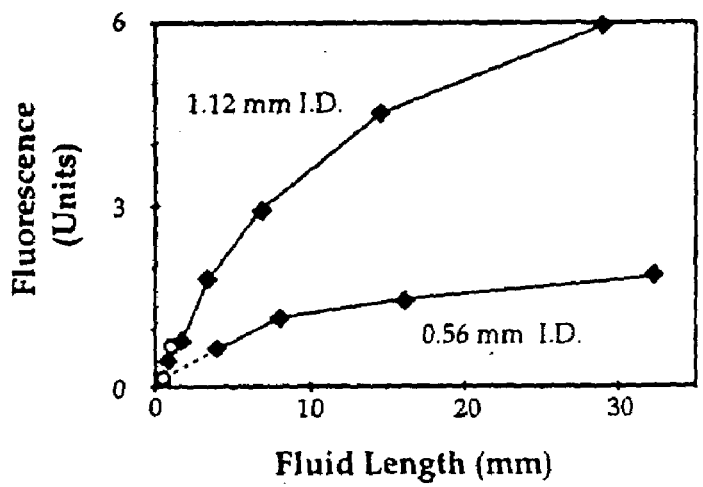
FIG. 22A charts the effectiveness of light piping by viewing the tip rather than the side of capillary sample container.
Figure 22B:
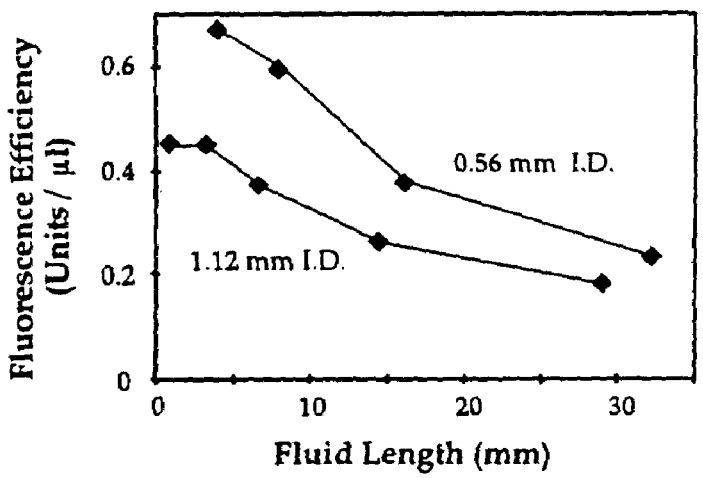
FIG. 22B charts the efficiency of light piping by two different sizes of capillary sample tubes.

FIG. 22A charts the effectiveness of light piping when detecting fluorescence at the tip of the capillary tube and shows a 10-fold increase in signal intensity by viewing the tip (closed diamonds) rather than the side (open circles) of the capillary sample container. Also, as indicated in FIG. 22B, the results obtained using capillary sample tubes of two different sizes and which were filled to different lengths with dsDNA stained with SYBR® Green I are plotted. As can be surmised from FIGS. 22A and 22B, the observed epifluorescence increases as more sample is added to the tube, although the fluorescence efficiency decreases.

The optical properties of the emission from a capillary were investigated by stimulating fluorescence in a capillary filled with a fluorescein solution at 470 nm. The emission from a blunt end of the capillary was seen to be homogenous across the face of the capillary as opposed to concentrated in the glass as would be expected if the emission were the result of evanescent wave fluorescence.

The optical components represented in FIG. 20 carry out paraxial epifluorescent illumination of the capillary tip, which provides advantageous results not otherwise obtainable. In FIG. 20, an excitation radiation source 468 is preferably a blue LED, such as one known in the industry as a super bright LED and available from LEDtronics. The emitted fluorescence signals are acquired by photo detectors 466A and 466B. The excitation radiation source 468 and the photo detectors 466A and 466B are supported on a mounting board 468 which also includes necessary circuitry and which integrates filters with the photo detectors 466A and 466B. A preferred mounting board is available from Ealing Electrooptics which includes 0.5 inch interference filters with high performance silicon photodiodes in TO5 packages. The excitation and detection components are supported directly on the mounting board 468 with associated electronics. It is preferred that the optical components are preferably ≦1.0 inches in diameter. A collimating lens 454, two dichroic filters 456A and 456B, a mirror 458, interference filters 460A-C, and aspheric focusing lenses 462A-C direct the radiation to and from the sample.

While the embodiment of the present invention represented in FIG. 20 utilizes only two colors/wavelengths when performing an analysis, those skilled in the art can readily adapt the embodiment to provide three, or more, color analysis. To provide three or more color analysis, the apparatus represented in FIG. 20 can accommodate additional dichroic filters and photo detectors. Moreover, it is within the scope of the present invention to allow simultaneous separation of wavelengths onto a linear photo detector array, as is available in the industry, for multicolor acquisition. When a linear photo detector array is used in accordance with the present invention, it is preferred that a prism or diffraction grating be utilized in cooperation with a lens and a photo detector array or CCD for detection of multiple wavelengths. One preferred linear photo detector array available in the industry collects 15-30 wavelength bins of 10-20 nm each between 500 and 800 nm. Various configurations of optical components, for example the Littrow autocollimating configuration for gratings used in most monochrometers, can be arrived at using the information set forth herein to arrive at the best accommodation between collection efficiency, spectral resolution and spatial requirements. The apparatus of FIG. 20 will now be further described incorporated into an automated thermal cycling apparatus represented in FIG. 21.

FIG. 21 provides a schematic representation of another presently preferred embodiment 400 of the present invention which includes rapid temperature cycling components, sample handling components, and the optical components represented in FIG. 20, all working together to provide fluorescence detection at the tip of the sample containers (epifluorescence). The rapid temperature cycler with epifluorescence detection 400 represented in FIG. 21 provides particular advantages. It is to be understood that this described embodiment is merely exemplary of the present invention and that those skilled in the art can arrive at many different arrangements for carrying out the invention claimed herein.

In the embodiment represented in FIG. 21, air is taken in through an aperture 470 and generally follows the flow path indicated by the lines 472. The temperature of the air, and thus the temperature of the plastic/glass sample container 450, is preferably adjusted using a 400 watt heating cartridge 474 which is preferably one available from Reheat, Inc. The heating cartridge 474 is positioned within a central duct 476. A fan 498 is provided to move the air in the indicated path 472. The fan is driven via a shaft 496 and a motor 494. The motor 494 is preferably a DC rare earth brush motor which is preferably available from Escap AG. and having a maximum rpm of 15,000. When heating the plastic/glass sample tubes 450, the heating cartridge is proportionally controlled and the fan is run at a relatively low speed (12 volts, 0.5 amp) to provide temperature homogeneity for all of the plastic/glass sample containers 450. When cooling the plastic/glass sample containers 450, the heating cartridge 474 is disabled and the motor 494 is run at a fast speed (for example with the above-mentioned preferred motor maximum speed is obtained by applying 27 volts, 1.4 amps). The fan 498 forces air into the aperture 470 and out via exhaust ports 471.

In the preferred rapid temperature cycler with epifluorescence detection 400, it is preferred that twenty-four plastic/glass sample containers 450 (two of which are represented in FIG. 21) be symmetrically arranged around the heating cartridge 474 and the central duct 476. The plastic/glass sample containers 450 are received by sleeves 451 which (due to their offset structure) allow for precise adjusting of the position of the individual plastic/glass sample containers 450 in a circular carousel 480. The sleeves 451 are preferably fabricated from brass. The off-axis structure of the sleeve 451 allows each sleeve 451 to be aligned so that the tip of the glass/plastic sample container 450 can be precisely adjusted to be at the optical focal point represented in FIG. 21, both laterally and longitudinally, at the time that the rapid temperature cycler with epifluorescence detection 400 is fabricated.

The carousel 480 is supported on a bearing 482 above a housing 490. The carousel 480 is positioned by a stepper motor 488 provided with a drive gear 484 connected to the motor 488 via a shaft 486. The stepper motor 488 is microstepped (using a controller (not explicitly represented in FIG. 21) from New England Affiliated Technologies) to provide over 10,000 steps per revolution of the carousel 480, providing precise positioning of each the plastic/glass sample containers 450. The interior of the housing 490 is provided with an insulative material 492, preferably in accordance with the previously described insulative material. Baffles 476 function to form the exhaust port 471 and to block ambient light.

FIGS. 21A-D provide additional detailed views of the plastic/glass sample containers 450 and will be referred to for an explanation of the preferred method of using the same. The plastic/glass sample container 450 includes a capillary tube portion 450B which is closed at one end. The capillary tube portion 450B can take many different configurations and is not limited to only a capillary tube type structure. It is, however, preferred that the volume of fluid held by the plastic/glass sample containers 450 be not more than 1 milliliter in order to promote sample temperature homogeneity and rapid thermal cycling. For example, it is preferred that the material from which the capillary tube portion 450B is fabricated have a thermal conductively in the range from about 20 to about 35 in accordance with the formula.

$$\left(\frac{cal\ cm}{cm^2 s\ degree\ C.}\right) \times 1$$

Further information regarding the thermal conductivity of different glasses can be obtained from R. C. Weast & M. J. Astle, HANDBOOK OF CHEMISTRY AND PHYSICS, page E-6 (1982) (CRC Press) which is now incorporated herein by reference. The plastic/glass sample containers 450 are also provided with a reservoir portion 450C which is preferably fabricated from an appropriate plastic and joined to the open end of the capillary tube portion 450B. While many different materials can be used for the reservoir portion 450C, it is preferred that a plastic material be formed in a funnel-like shape and attached to the capillary tube portion 450B.

A sample S is loaded into the composite plastic/glass sample container 450 using a pipette P, or some other appropriate instrument, either manually or using an automated process. It is preferred that the volume of the sample be in the range from about 0.01 µl to about 10,000 µl, more preferably in the range from about 0.01 µl to about 100 µl, and most preferably in the range from about 0.01 µl to about 10 µl, with about 5 µl being the most preferred volume. Once a sample has been added to each plastic/glass sample container 450, the plastic/glass sample containers 450 are centrifuged at low speed to place the samples at the tips of the closed end of the capillary portion 450B, so that the sample forms a 0.2-2.0 cm column of fluid 450A as represented best in FIG. 21B. A stopper 450D (which is preferably configured as a plastic plug) is then placed in the reservoir portion 450C to seal the plastic/glass sample container 450 as shown best in FIG. 21C and the plastic/glass sample container 450 is placed in the sleeve 451 in the rapid temperature cycler with epifluorescence detection 400. It is also within the scope of the present invention to provide different structures to seal the capillary tube portion 450B.

The capillary tube portion 450B of the glass/plastic sample container 450 is preferably a glass capillary tube available in the industry having 0.8 mm inner diameter and a 1.0 mm outer diameter, and which is closed/sealed on one end and flared at the other end for receiving the plastic reservoir 450C. The glass/plastic sample containers 450 can be readily and economically fabricated. The shape of the tip 450E of the capillary tube portion 450B is optimized for optical efficiency. Flat tips as well as tips with various outside curvatures and inside curvature are all contemplated within the scope of the present invention. Those skilled in the art can select the most efficient configuration for the tip.

As can be discerned from FIGS. 21A-D, the addition of plastic loading and sealing structures to a capillary tube provides great advantages and allows efficient use of glass capillary tubes while retaining their desirable thermal characteristics. It will be appreciated that it is within the scope of the present invention to add the samples to the plastic/glass sample containers 450, and to subject the samples to centrifuging, in a 96-well format. Moreover, it is within the scope of the present invention to load the plastic/glass sample containers individually into the rapid temperature cycler with epifluorescence detection 400 and it is also within the scope of the present invention to provide an embodiment of the present invention to load the plastic/glass sample containers 450 in a 96-well format or some other format.

Advantageously, the composite plastic/glass sample containers 450 provide a convenient, inexpensive sample holder. With the embodiment of FIG. 21, it is preferred that fluorescence is acquired from single samples one to ten times each second. When acquiring fluorescence from multiple samples at the preferred rate, the samples need to be moved into position by rotation of the carousel 480 relatively rapidly. With the preferred stepper motor 488 and appropriate control devices (which can be selected using the information contained herein) each of the twenty-four samples can be rapidly and accurately moved to the monitoring position represented in FIG. 21.

When the fluorescent signal from each sample is acquired for 100 msec., the signal variation (with repositioning) is <1%. It will be appreciated that it is within the scope of the present invention to decrease the signal acquisition time, increase the transit speeds, and also observe the coefficient of variation from repeated sampling. When twenty-four samples are processed, and the carousel is rotated without stopping at a rate between one and ten revolutions per second, each sample has 0.37-3.7 msec of excitation and detection.

Using the information set forth herein, one skilled the art can select whether the fluorescent signal is integrated via software or hardware. In one preferred embodiment, a graphical programming language is used in connection with the rapid temperature cycler with epifluorescence detection 400, such as one known in the industry as LabView (available from National Instruments), which has subprograms for peak detection and integration. In another preferred embodiment, integration is done in hardware with variable integration time (user adjustable sensitivity control) so that the signals reach a level optimal for analog-to-digital conversion.

Using the rapid temperature cycler with epifluorescence detection 400 represented in FIG. 21, continuous monitoring of the sample as the reaction is ongoing allows determination of temperature cycling requirements during amplification, based on continuous observation of annealing, extension, and denaturation. This is in contrast to the prior art where all cycling parameters are determined and programmed before amplification begins. In accordance with the prior art, using complementary oligonucleotides equivalent to the lowest melting primer, the annealing efficiency is controlled even during early cycles. In many cases, extension and denaturation can only be monitored with dsDNA dyes during later cycles when enough product has been made. Significantly, such a requirement is not usually a problem because denaturation and extension conditions are made permissive enough to amplify most products, and data from the first amplification can be used to optimize subsequent runs.

Still referring to FIG. 21, a user interface and instrument control 500 can be fabricated using the information set forth herein in connection with the embodiment of FIG. 11. As one preferred example of a user interface and instrument control 500, a PENTIUM™ microcomputer running the LabView programming language with a 12-bit multifunction input/output card (available from National Instruments) provides data acquisition and control. It is preferred that the analog output signals be used to adjust the amplifiers associated with the photo detectors 466A and 466B. Analog input channels also measure the temperature of the samples via a thermocouple 499 as well as the fluorescent detected from the sample by the photodiodes. The user interface and instrument control 500 represented in FIG. 21 also provides digital I/O control of the excitation radiation source 468, the direction of the stepper motor 488, the heating cartridge 474, and the fan 498.

When continuous fluorescence monitoring of PCR samples containing the dsDNA dye SYBR Green I or fluorescently labeled oligonucleotide probes can be used to monitor hybridization and melting during individual amplification cycles. This information can be used by preferred arrangements for the user interface and instrument control 500 to provide improved and customized thermal cycling conditions. The benefits of using hybridization information for temperature cycling include:

(A) Ensuring that complete denaturation of the PCR product occurs with each cycle while:

Minimizing exposure to excessively high denaturation temperatures, thus, avoiding heat induced damage to the amplification products and polymerase.

Increasing reaction specificity by minimizing the denaturation temperature which selects against products with a $T_m$ higher than the intended amplification product.

(B) Maximizing the amplification efficiency by ensuring adequate time for product extension with each cycle while:

Minimizing the amount of time required for amplification by allowing no longer than needed to complete product extension.

Enhancing reaction specificity by selecting against products longer than the intended amplification product.

(C) Maximizing the amplification efficiency by ensuring adequate time for product extension each cycle while:

Minimizing the amount of time required for amplification by allowing no longer than needed to complete product extension.

Enhancing reaction specificity by selecting against products longer than the intended amplification product. These would require longer than the allotted time to complete product extension.

(D) Initiating thermal cycling changes dependent on the level of fluorescence obtained or the current efficiency of amplification. For example, over-amplification and nonspecific reaction products can be minimized by terminating thermal cycling when the efficiency drops to a certain level. As another example, temperature cycling can be modified to initiate slower temperature ramps for melting curve acquisition when the fluorescence becomes detectable. This saves time because the slower ramps need not be used on earlier cycles. Other desirable changes may become evident on continued practice of the invention.

(E) Minimizing over-amplification damage to PCR product and/or initiation of melting curve acquisition before over-amplification has increased the background of nonspecific reaction products.

In accordance with the present invention, the user interface and instrument control 500 can follow preprogrammed time/temperature set points and/or, advantageously, can acquire detected fluorescence values and then use the acquired detected fluorescence values to alter or adjust one or more reaction parameters in real time to optimize the results obtained. As used herein, the term "reaction parameter" includes, but is not limited to, any parameter which is used as a basis for controlling a reaction. Such reaction parameters include, but are not limited to, denaturation temperature and time, primer annealing temperature and time, probe annealing temperature and time, enzyme extension temperature and time, and number of cycles. In general, control of the reaction is initially based on an estimate of reaction parameters from the fluorescence data. The original fluorescence data is either acquired as a change in fluorescence over time (temperature specific rates of denaturation, annealing, and extension), a change in fluorescence over temperature (product or probe $T_m$), or a change in extent of amplification (amplification yield and efficiency). These rates, $_{Tm}$'s and their first and second derivatives are used to determine optimal reaction parameters such as denaturation temperature and time, primer annealing temperature and time, probe annealing temperature and time, enzyme extension temperature and time, and number of cycles.

Figure 22C:
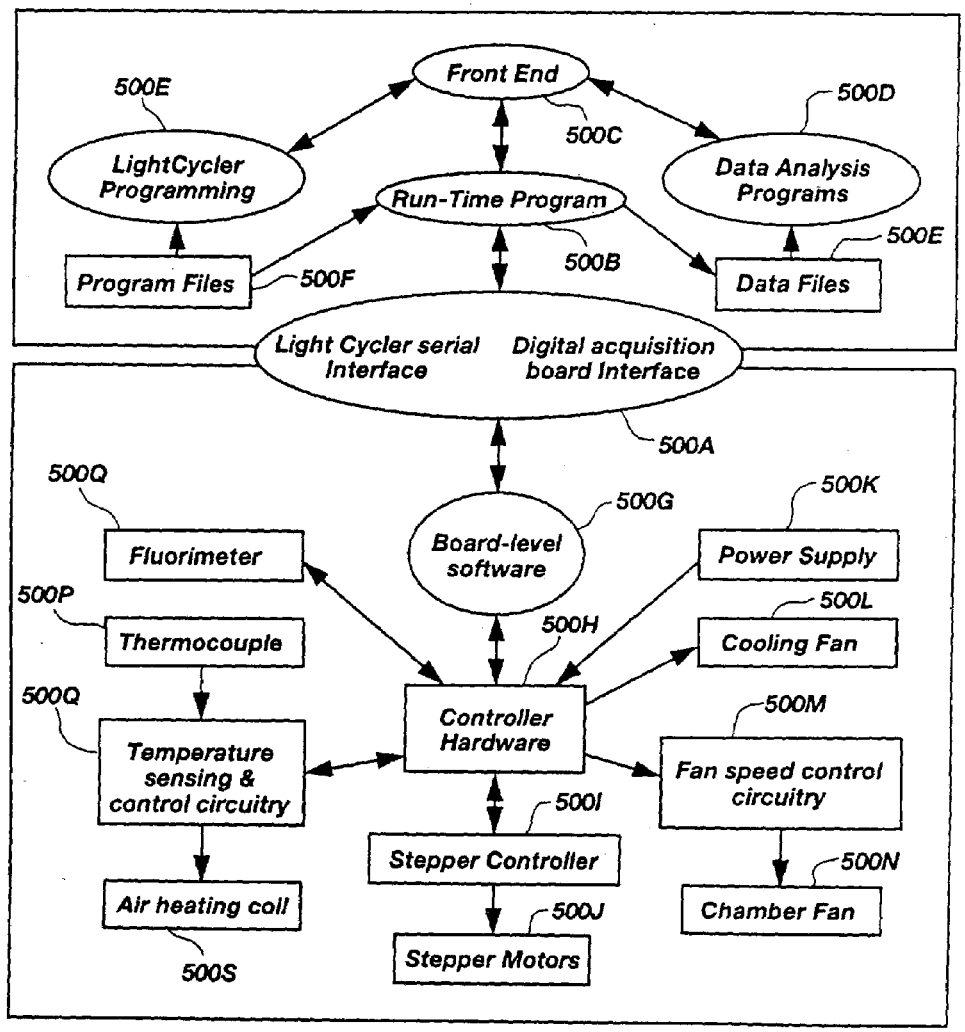
FIG. 22C is a high level block diagram showing the tasks which are performed by one preferred embodiment of the present invention which includes a rapid temperature cycler with epifluorescence detection.

As depicted in the high level block of FIG. 22C, tasks are divided between those carried out by a portion of the user interface and instrument control 500 (which preferably can be an IBM compatible computer using programming based upon the teachings set forth herein)(Blocks 500A-500E in FIG. 22C) and those carried out by the remaining components (Blocks 500A, and 500G-500S in FIG. 22C) of the rapid temperature cycler with epifluorescence detection 400. It is to be understood that the block diagram of FIG. 22C is merely exemplary and many different arrangements can be used to carry out the present invention.

Figure 22D:
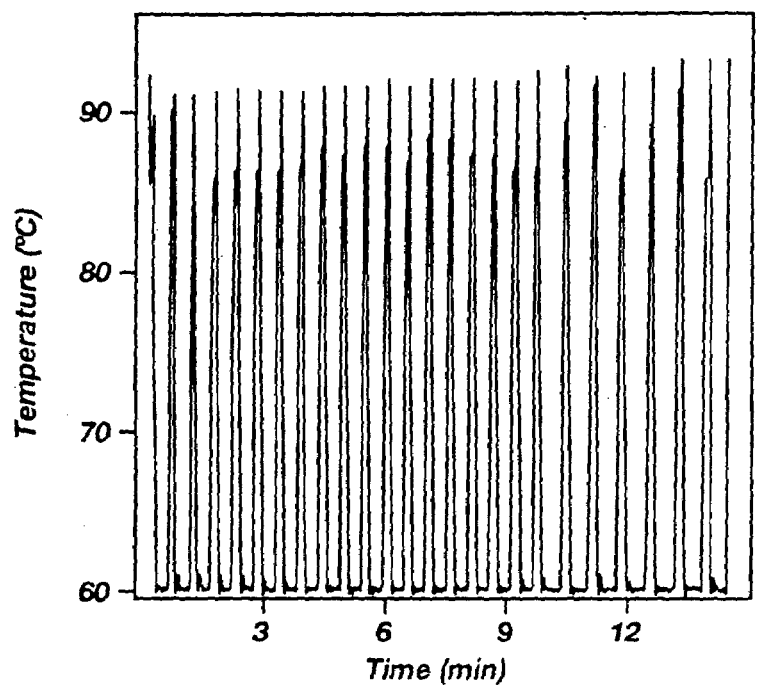
FIG. 22D is a plot of temperature vs. time for a PCR reaction in which fluorescence feedback was used to control reaction parameters.

As an example of the advantages of the arrangement shown in FIG. 22C, product melting control will be discussed. A melting peak fluorescence value is acquired for the intended PCR product and a baseline fluorescence is acquired or the sample containing the reaction mixture at the temperature at which the product is seen to have completely melted. Each cycle of the reaction uses this fluorescence value as a target. The approach being described in this example uses two stages in to provide a time lag to accommodate the requirement of sending the fluorescence values to a separate PC computer. With each product melting step, the temperature is increased until the fluorescence reaches an intermediate value, then the power applied to the heating device is reduced so that a temperature ramp of approximately 3° C. per second is imposed so that the PC computer has adequate time to analyze the fluorescence and convey to other components that product denaturation has occurred. The resulting time/temperature plot is shown in FIG. 22D. FIG. 22D shows a characteristic increase in the melting temperature after twenty cycles as the concentration of amplification product grows. This is due to the fact that product $T_m$ is a function of product concentration.

As an example of the further advantages of the arrangement shown in FIG. 22C, product annealing/extension will be discussed. During an extended hold at a combined annealing/extension temperature, the fluorescence of the sample is monitored and this information is used to ensure that adequate, but not excessive, time had been allowed for product extension. Fluorescence is monitored at ten second intervals, and if the fluoresce increased more than a preset ratio (typically 1.00 to 1.05), then the annealing/extension step is continued. Otherwise, the next product melting step is initiated. The interval of ten seconds is chosen to give a minimum of twenty seconds at the combined annealing/extension temperature.

Figure 22E:
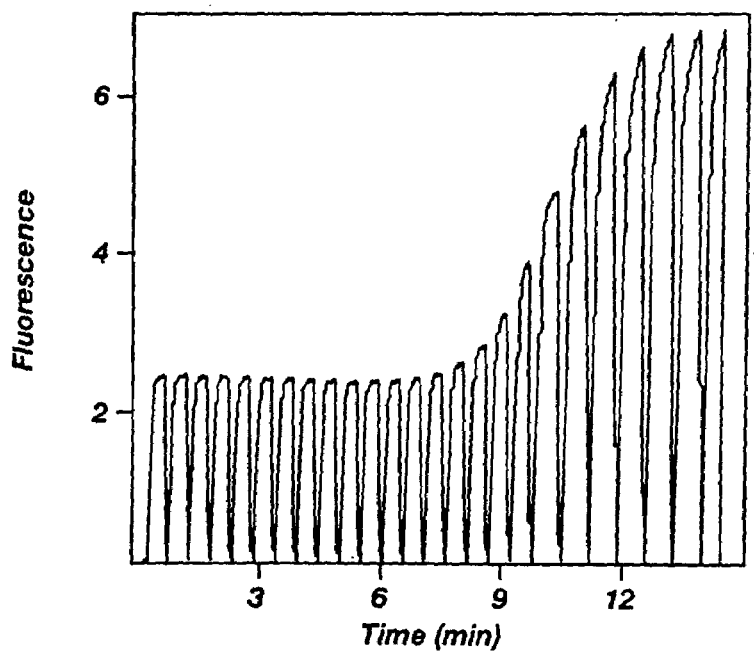
FIG. 22E is a plot of fluorescence vs. time for a PCR reaction in which fluorescence feedback was used to control reaction parameters.
Figure 23:
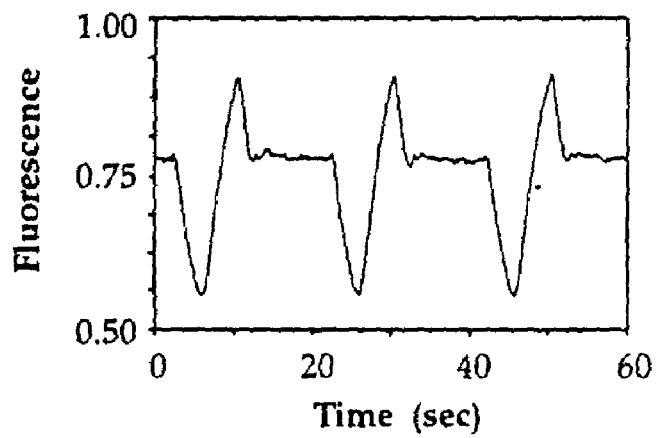
FIG. 23 is a plot of fluorescence vs. time showing the inverse relationship between temperature and fluorescence.
Figure 24:
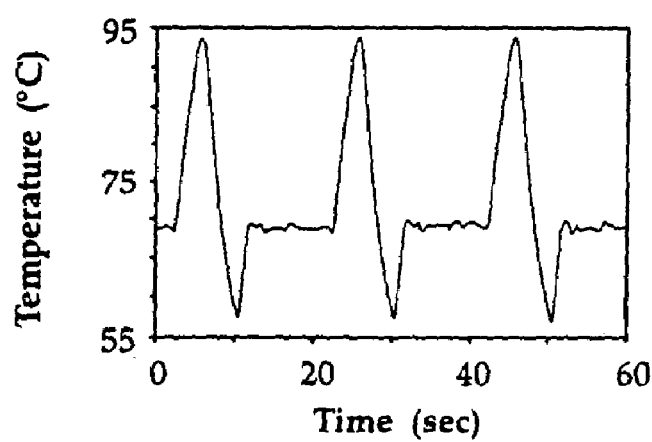
FIG. 24 is a plot of temperature vs. time showing the inverse relationship between temperature and fluorescence.

FIG. 22E shows a fluorescence/time plot which exhibits a characteristic increase in the dwell time at the combined annealing/extension temperature as the concentration of amplification product grows. This is due to the fact that as the primer concentration and polymerase become limiting more time is needed to complete product extension with each cycle.

As a yet another example of the advantages of the arrangement shown in FIG. 22C, amplification plateau will be discussed. At the end of each annealing/extension step, the fluorescence value is acquired and stored. When this value increases to 1.2 times the lowest end-cycle fluorescence value and had subsequently stopped increasing below a user settable ratio (typically 1.00-1.02) the thermal cycle is terminated. Alternatively, a melting curve accusation step is initiated by entering a slow 0.1° C. to 0.2° C./second temperature ramp through the product $T_m$ and monitoring the fluorescence of the sample continuously. The resulting fluorescence/time plot shown in FIG. 22D shows that after twenty-five cycles of amplification the ratio of cycle-by-cycle fluorescence growth fell below 1.00 and the reaction terminated. It will be appreciated that this approach can be used to acquire a high resolution melting curve for each sample. As a sample reaches its amplification plateau, a melting curve can be acquired for that sample, then regular temperature cycling can resume until another reaction reaches its amplification plateau.

FIG. 22E illustrates useful temperature vs. time segments for fluorescence hybridization monitoring. Product melting curves are obtained during a slow temperature increase to denaturation. By quickly lowering the temperature after denaturation to a constant temperature, product, probe, or primer annealing can be detected. Probe melting curves are obtained by slowly heating through temperatures around the probe $T_m$. Those skilled in the art can readily utilize the system represented in FIG. 21 to provide the necessary analysis, in real time if desired, during temperature cycling to provide heretofore unavailable information on the characteristics of the product, probe, and primer using the hardware and software described herein.

Absolute quantification of product is also advantageously carried out in accordance with the present invention. Continuous monitoring of double stranded DNA formation allows direct, absolute DNA quantification by reannealing kinetics. The sample temperature is quickly dropped from the denaturation temperature and held constant at a lower temperature that is still high enough to prevent primer annealing. The rate of product reannealing then follows second order kinetics. When different concentrations of DNA are tested, the shape of the reannealing curve is characteristic of the DNA concentration (see FIG. 26). For any given PCR product and temperature, a second order rate constant can be measured. Once the rate constant is known, any unknown DNA concentration can be determined from experimental reannealing data. The curves can be fit by non-linear least squares regression during temperature cycling in real time using the LabView programming environment (explained previously). Cooling is not instantaneous, and some reannealing occurs before a constant temperature is reached, but regression analysis allow for this in accordance with the present invention. (see FIG. 27). The technique requires pure PCR product, but this can be verified by melting curves also obtained during temperature cycling. Quantification by reannealing kinetics is independent of signal level and not affected by sample volume differences.

Figure 27B:
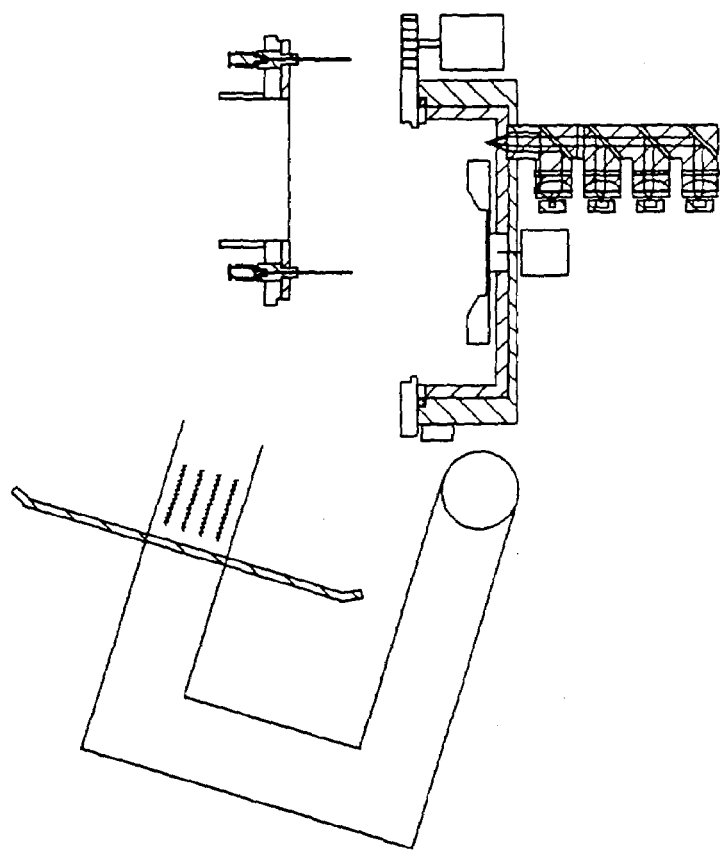
FIGS. 27A and 27B are cross sectional schematic views of the embodiment represented in FIG. 28 in a run mode and a load mode respectively.
Figure 27A:
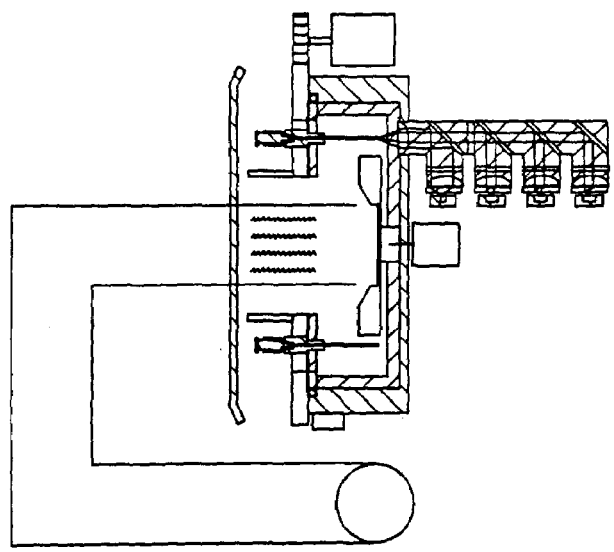
Figure 28:
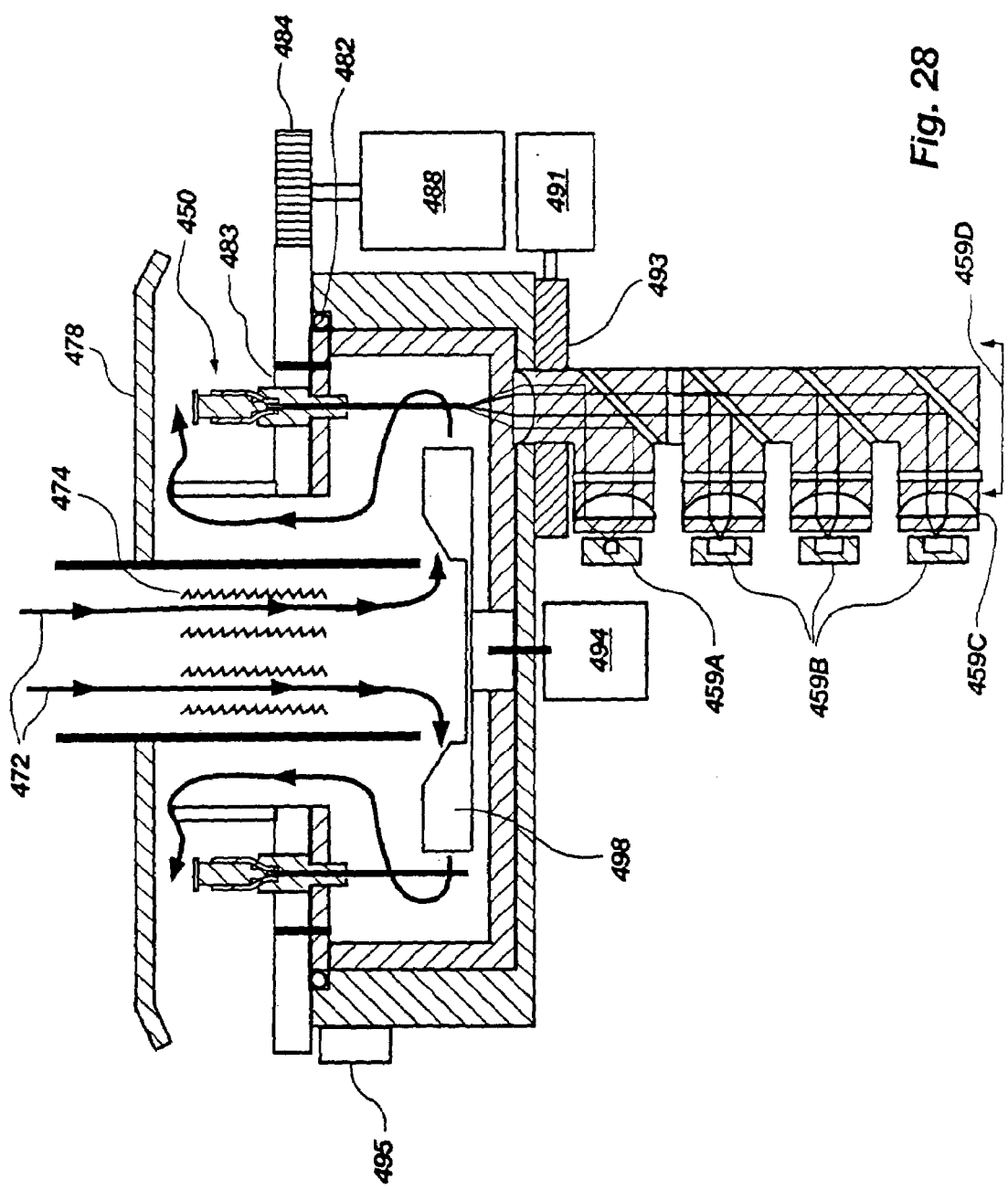
FIG. 28 is a schematic representation of another embodiment of the present invention which is a rapid temperature cycler with fluorescence detection at the tip of the sample containers and which includes positioning for fluorescence detection in two dimensions to optimize detection.

FIG. 28 is a schematic representation of another embodiment of the present invention which includes many of the structures included in the embodiment of FIG. 21. In order to provide a succinct description of the embodiment of FIG. 28, only those significant differences between those components represented in FIG. 21 and those components represented in FIG. 28 will be explained with the understanding that one skilled in the art can readily use the information contained herein to fabricate embodiments of the present invention. FIGS. 27A and 27B are cross sectional schematic views of the embodiment represented in FIG. 28 in a run mode and a load mode, respectively.

Figure 29:
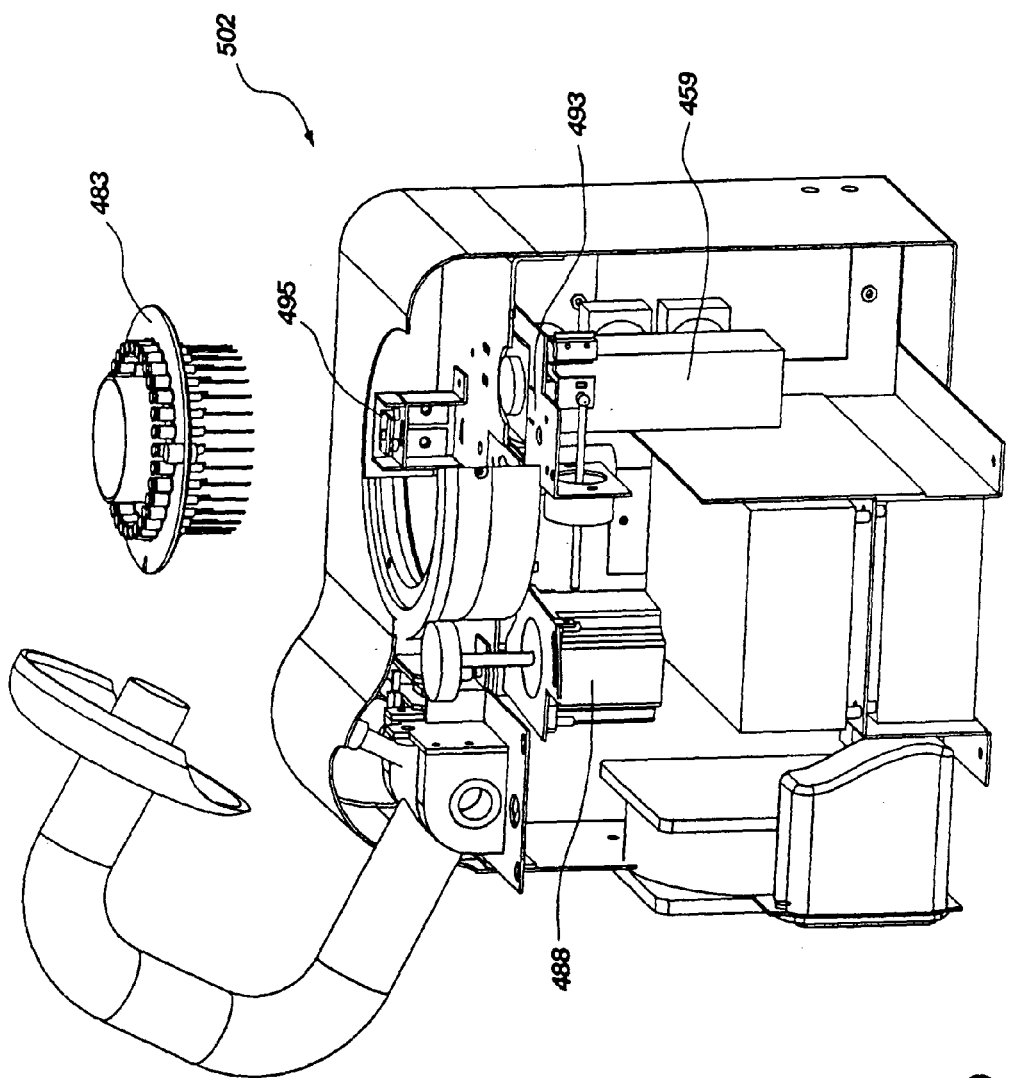
FIG. 29 is a perspective view of the exterior of the embodiment of the present invention including the components illustrated in the schematic representation of FIG. 28.

The embodiment of FIG. 28 is a rapid temperature cycler, generally designed at 502, with fluorescence detection at the tip of the sample containers with automatic positioning of the sample containers in two dimensions which improves the fluoresce signal which is obtained from the sample. FIG. 29 is a perspective view of the exterior of the embodiment of the present invention including the components illustrated in the schematic representation of FIG. 28.

As seen in both FIGS. 28 and 29, a removable circular sample tray 483 holds thirty-two samples. The removable circular sample tray 483 is placed into the rapid temperature cycler 502 so that it engages a carousel 481 which is driven by a motor 488. As the carousel 481 rotates, a hall effect position locator is used to precisely position the carousel 481 so that the each sample is precisely positioned over a flourimeter assembly 459. The flourimeter assembly 459 preferably includes a LED source 459A, three photodiodes 459B, focusing lenses 459C, and a filter assembly 459D. The flourimeter assembly 459 is similar in structure and function to that represented in FIG. 20.

Most advantageously, the fluorimeter is mounted on a slicer bearing 493 which is moved by a lateral stepper motor 491. As the carousel 481 rotates, the composite plastic/glass sample containers 450 are precisely positioned over the fluorimeter assembly 459 in the direction of the carousel and the position is noted by the apparatus via the hall effect position locator 495 while the lateral stepper motor 491 adjusts the position of the fluorimeter assembly 459 is adjusted in a second dimension, and the position noted. Thus, the rapid temperature cycler 502 provides for improved placement of a plurality of samples into the apparatus using a removable sample tray 483 and provides for improved detection of a fluorescence signal from a sample.

Figure 30A:
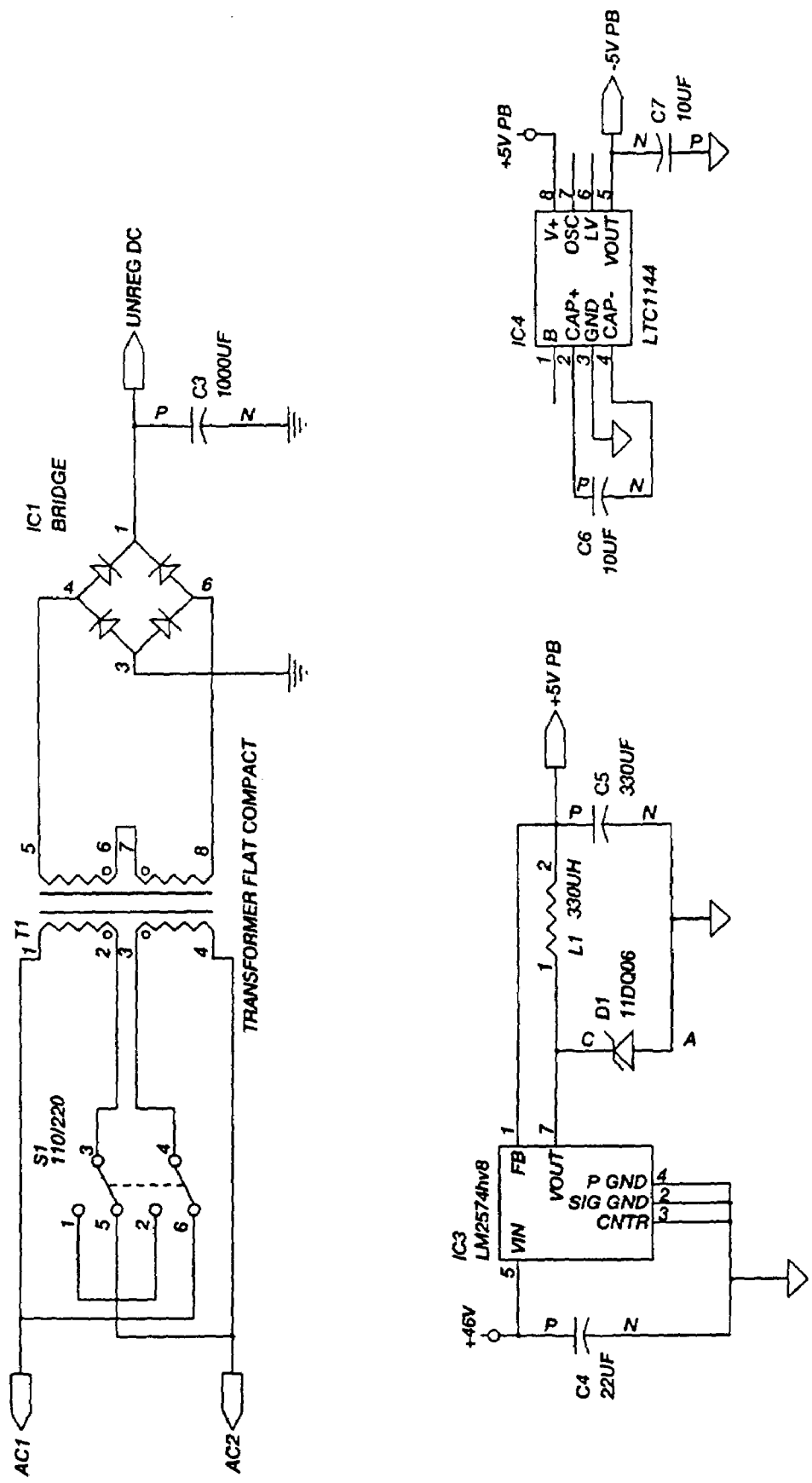
FIGS. 30A-30V are detailed schematic diagrams of the electrical components of one preferred embodiment of the present invention.
Figure 30B:
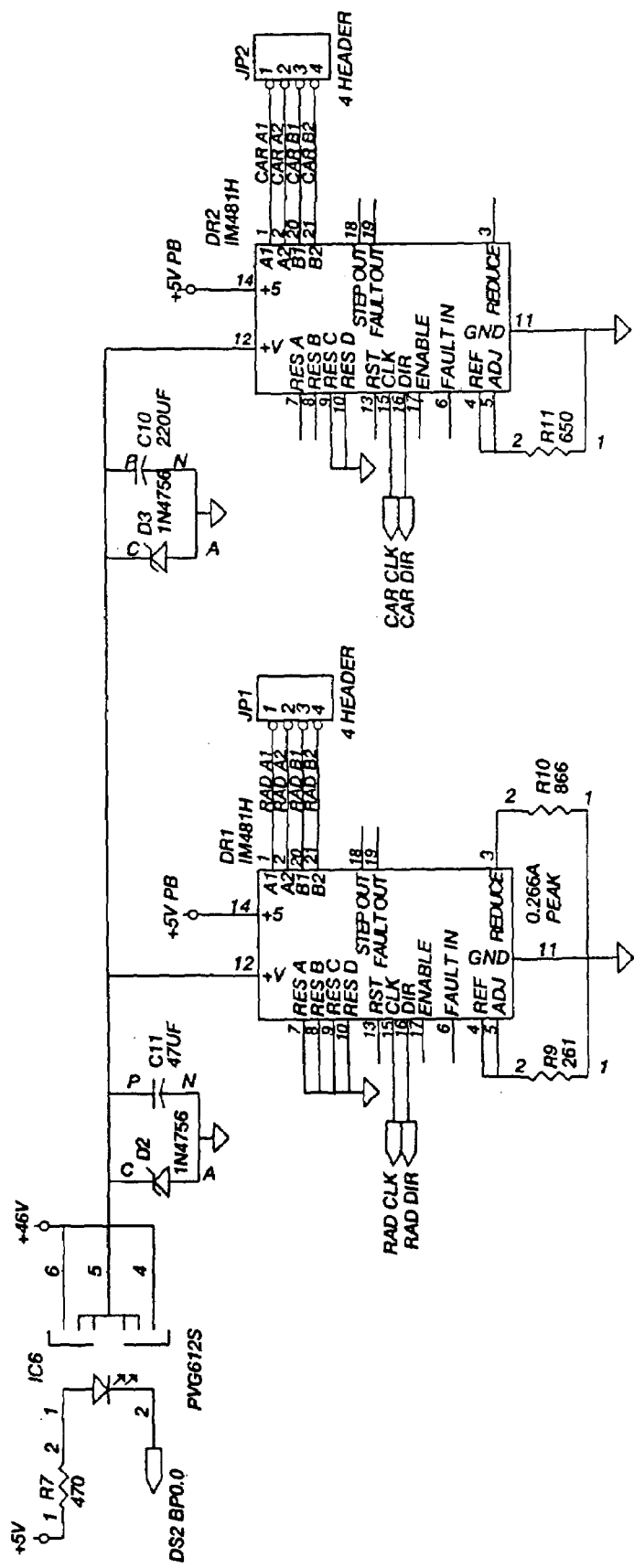
Figure 30C:
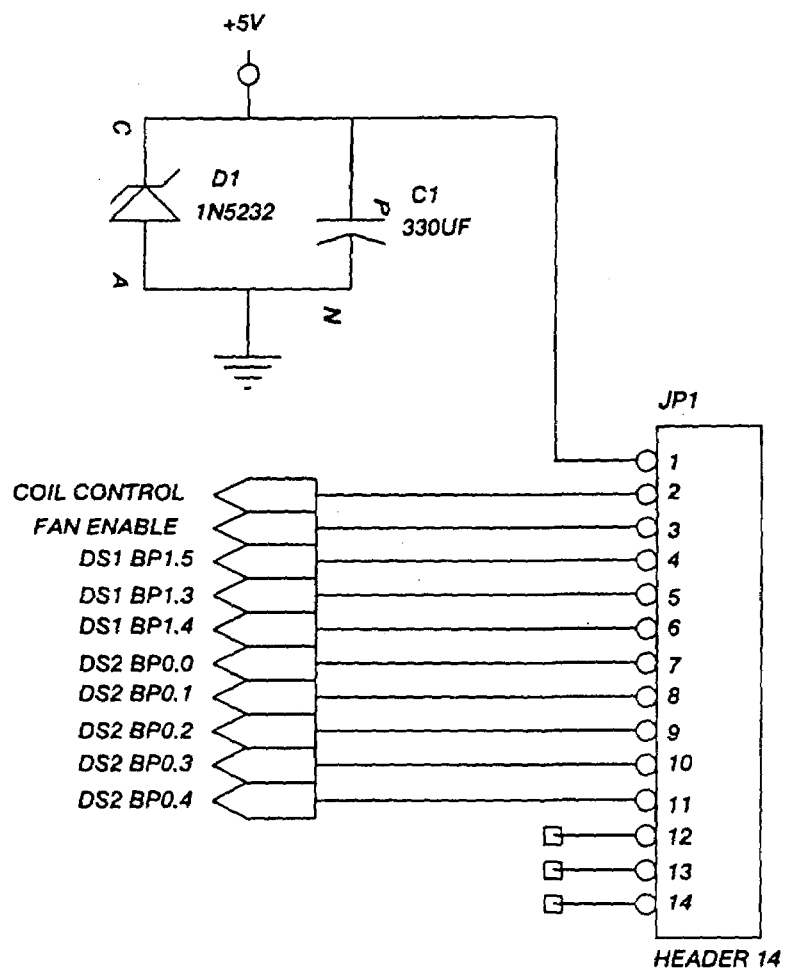
Figure 30C:
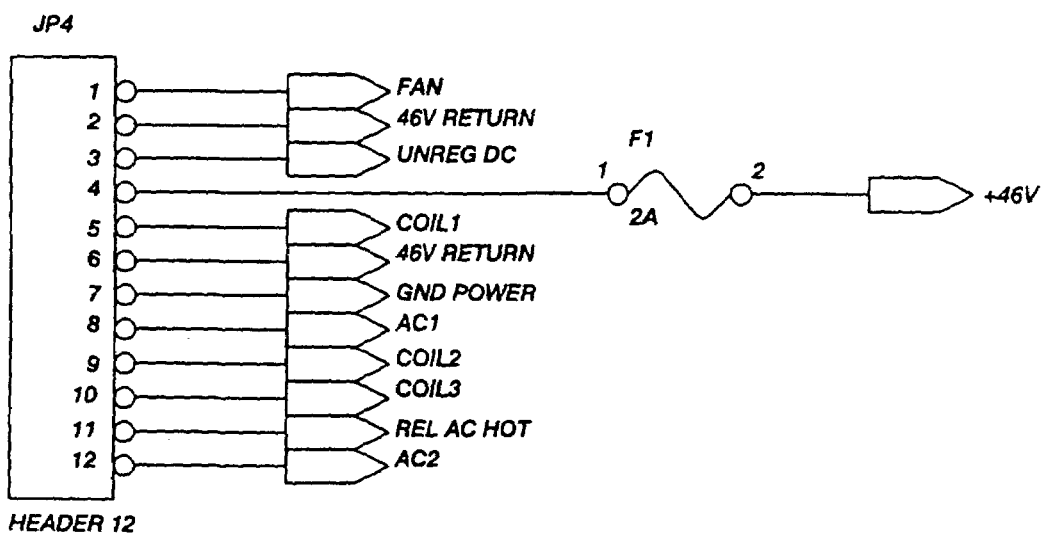
Figure 30D:
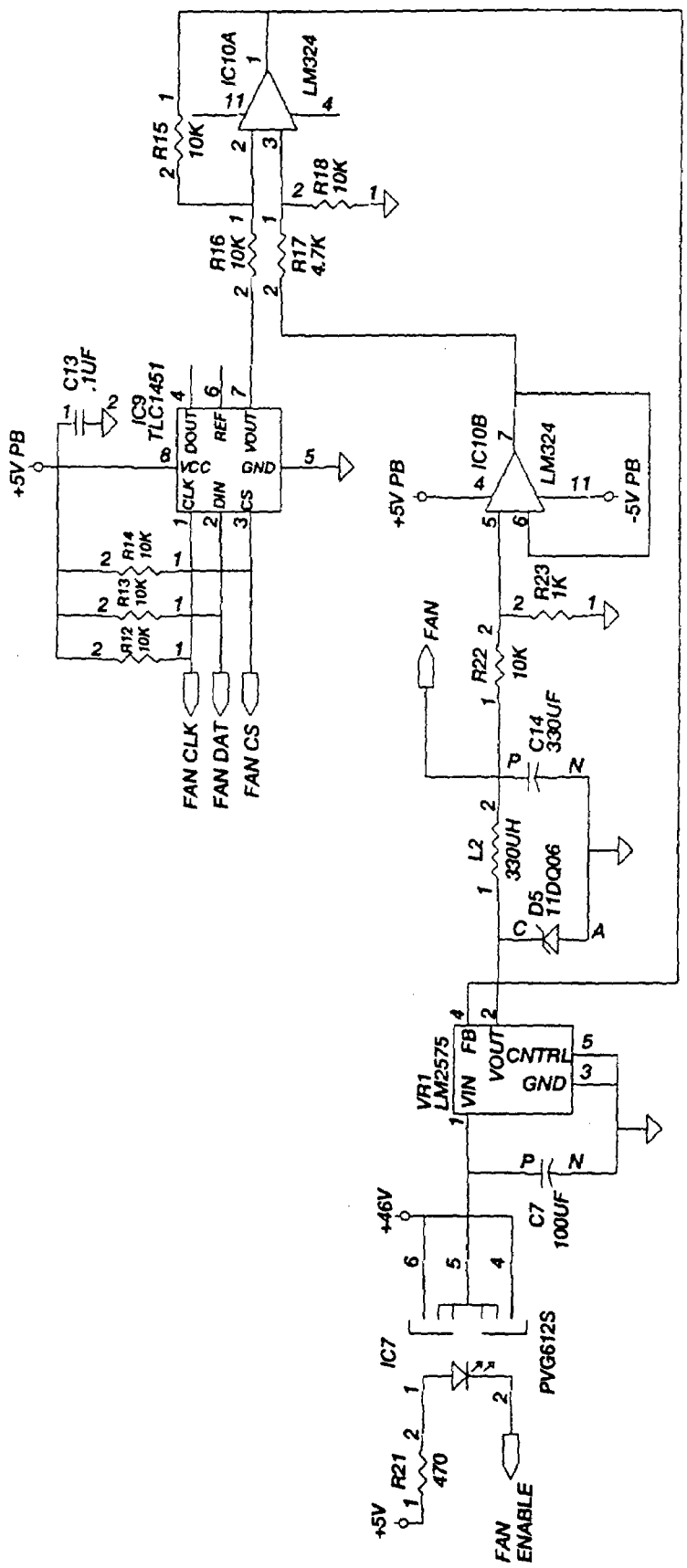
Figure 30E:
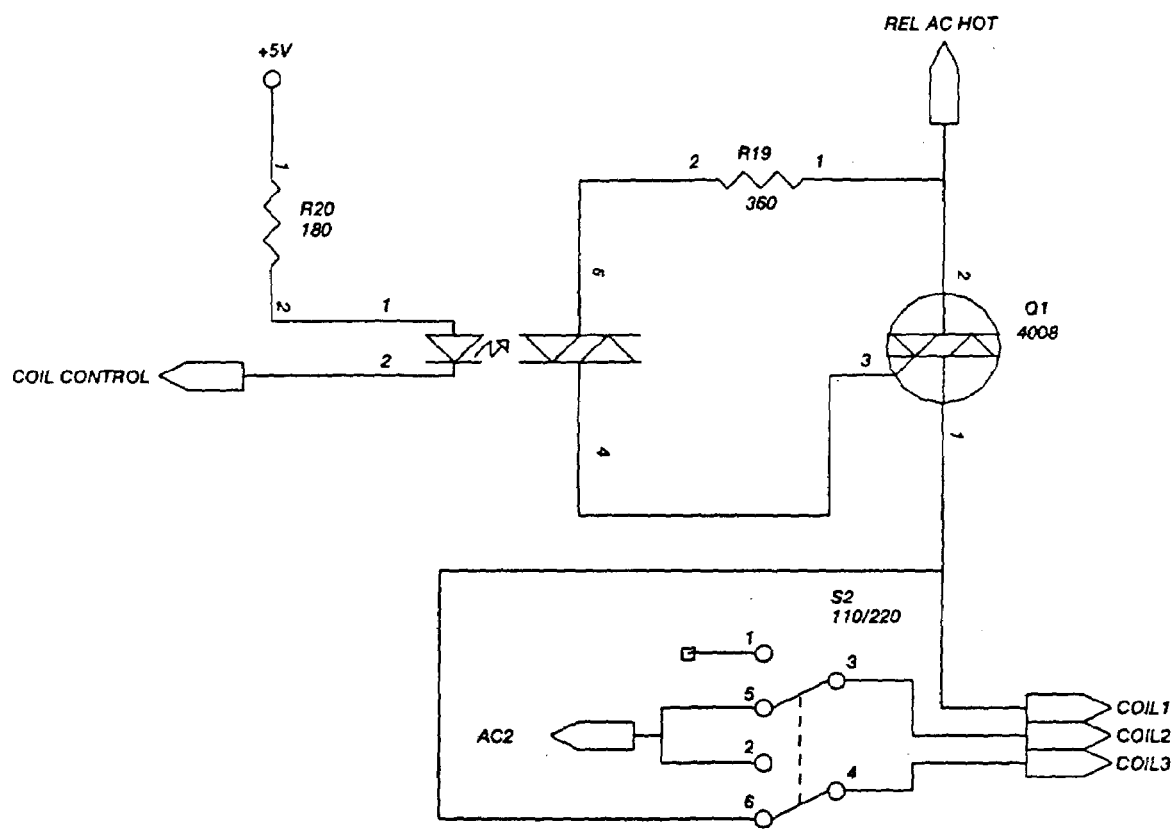
Figure 30F:
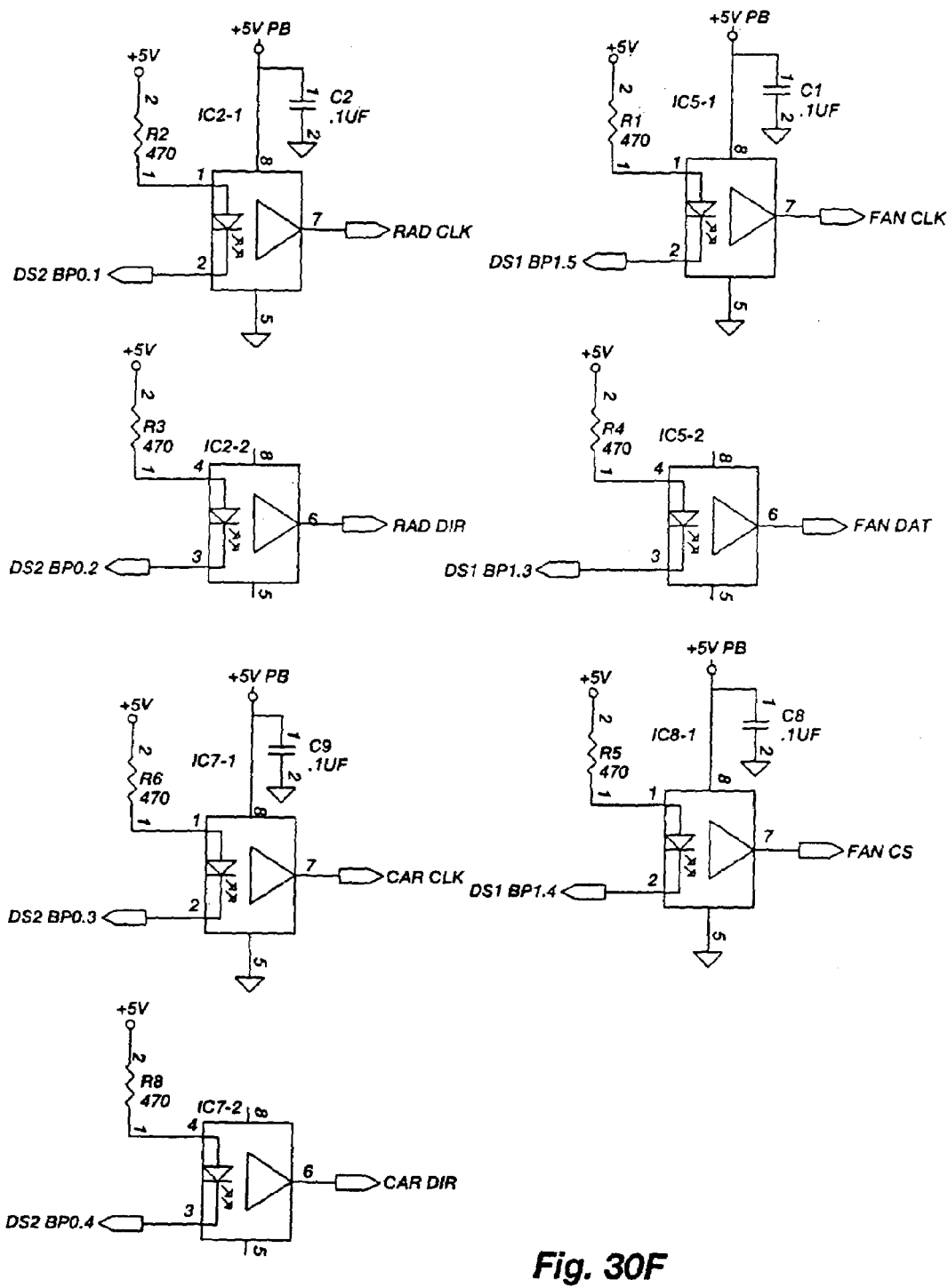
Figure 30G:
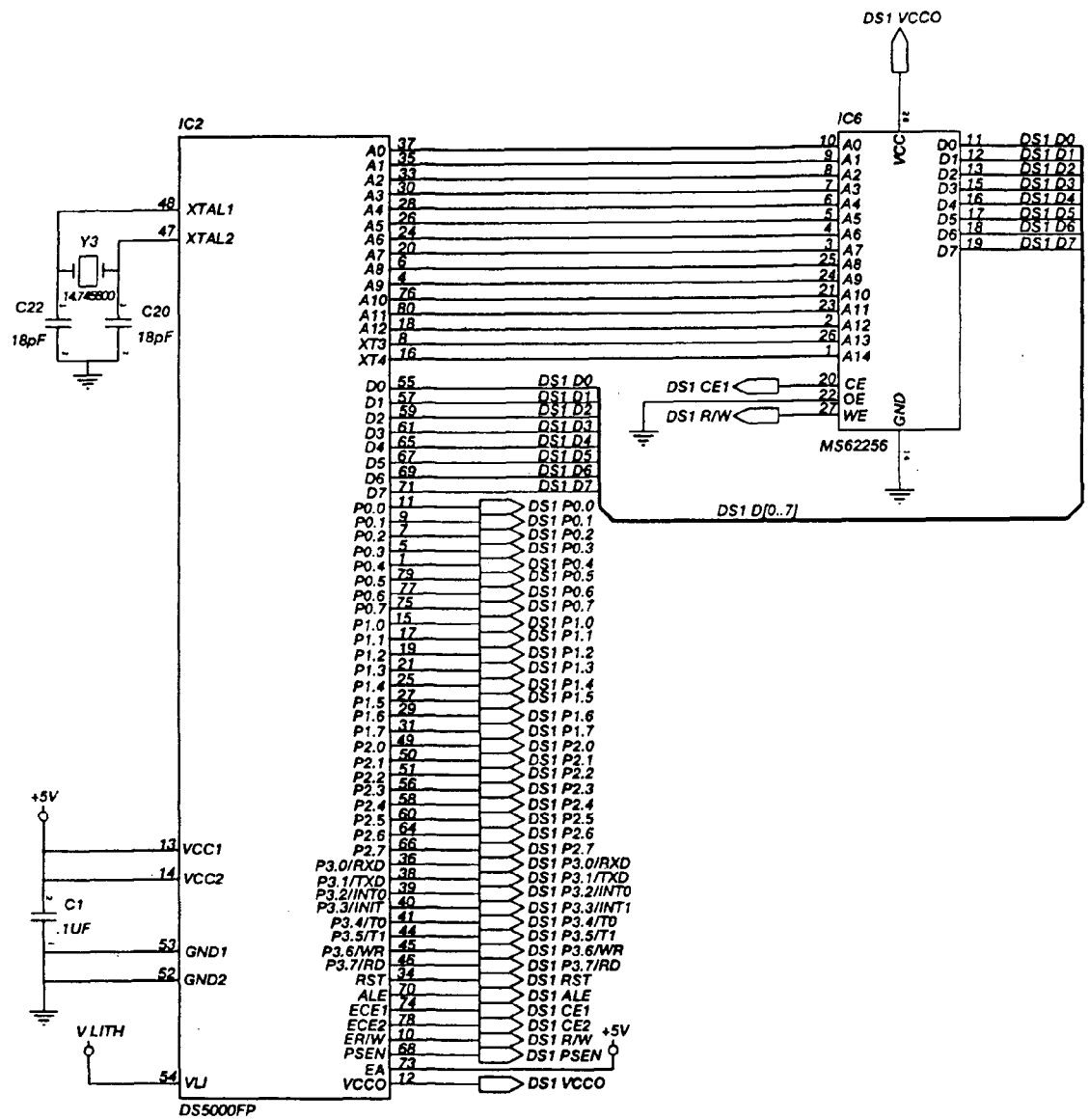
Figure 30H:
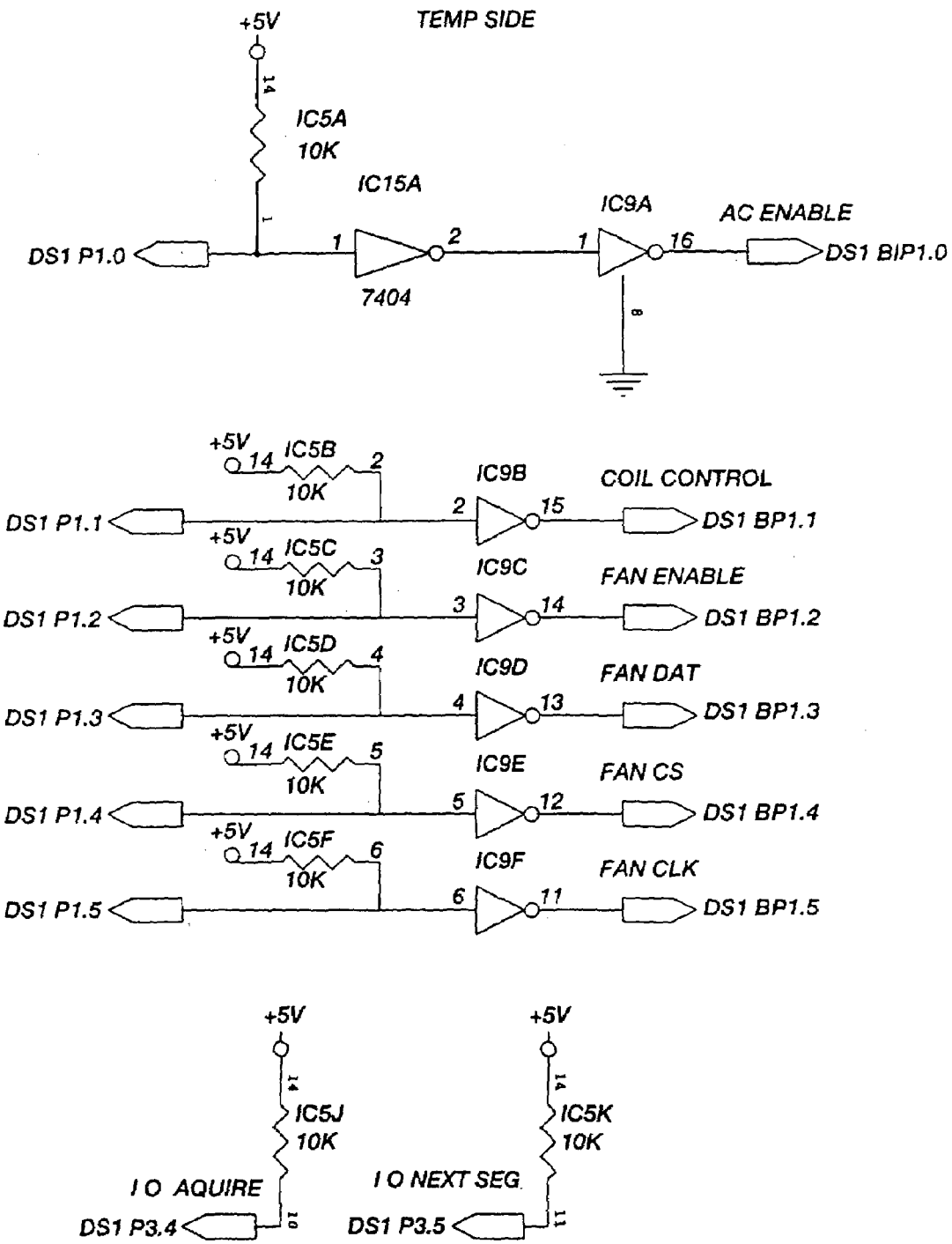
Figure 30I:
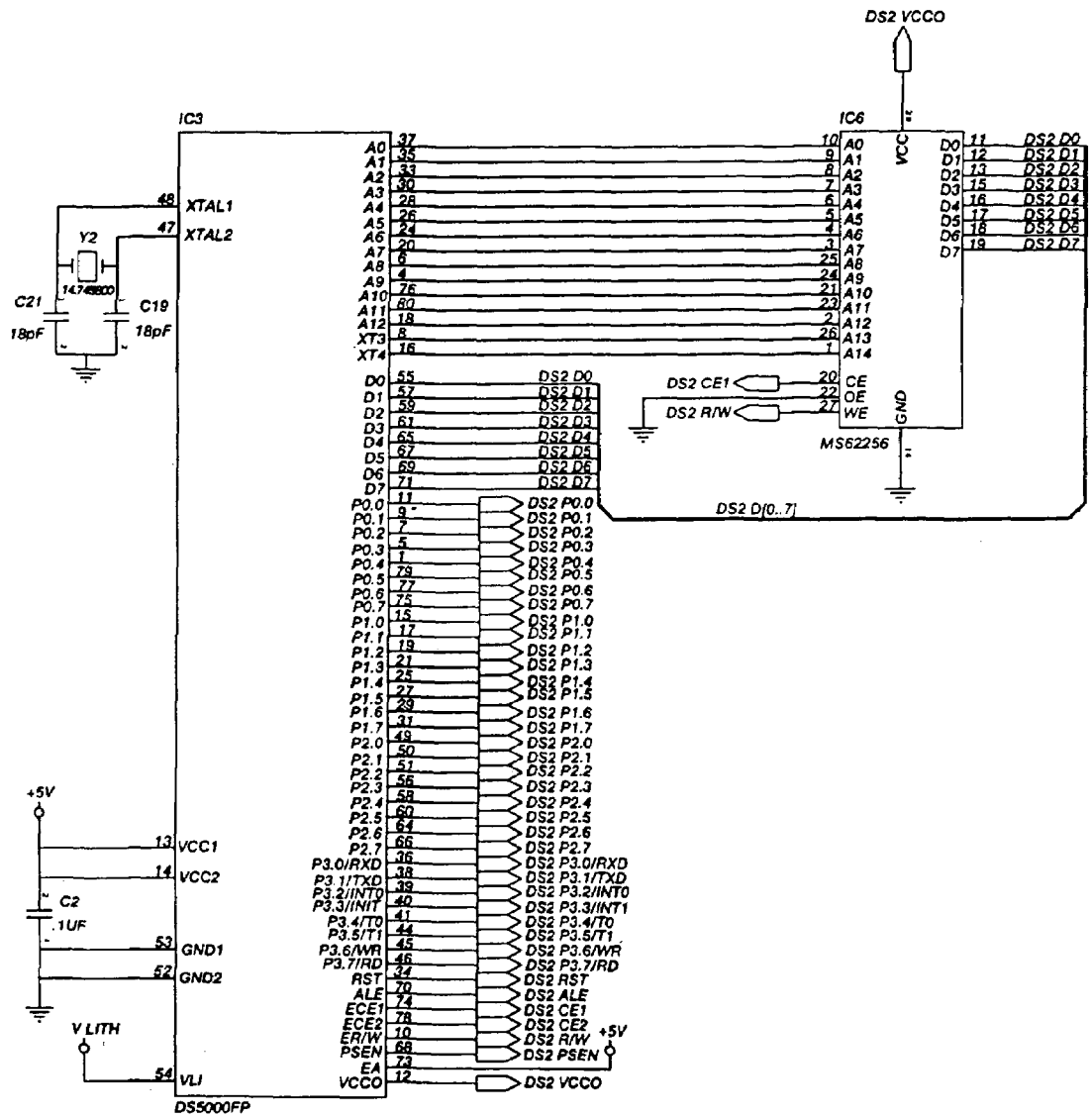
Figure 30J:
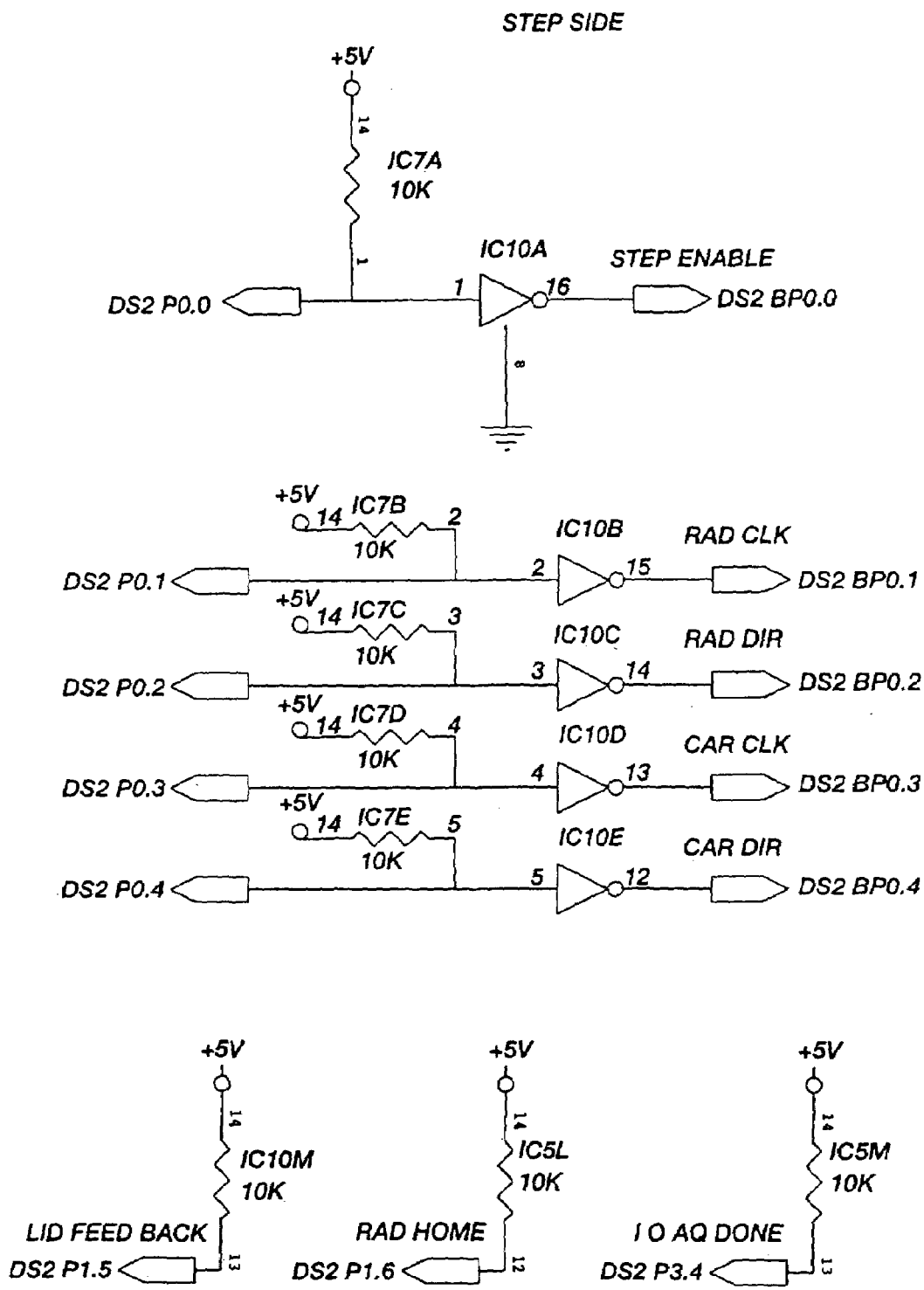
Figure 30K:
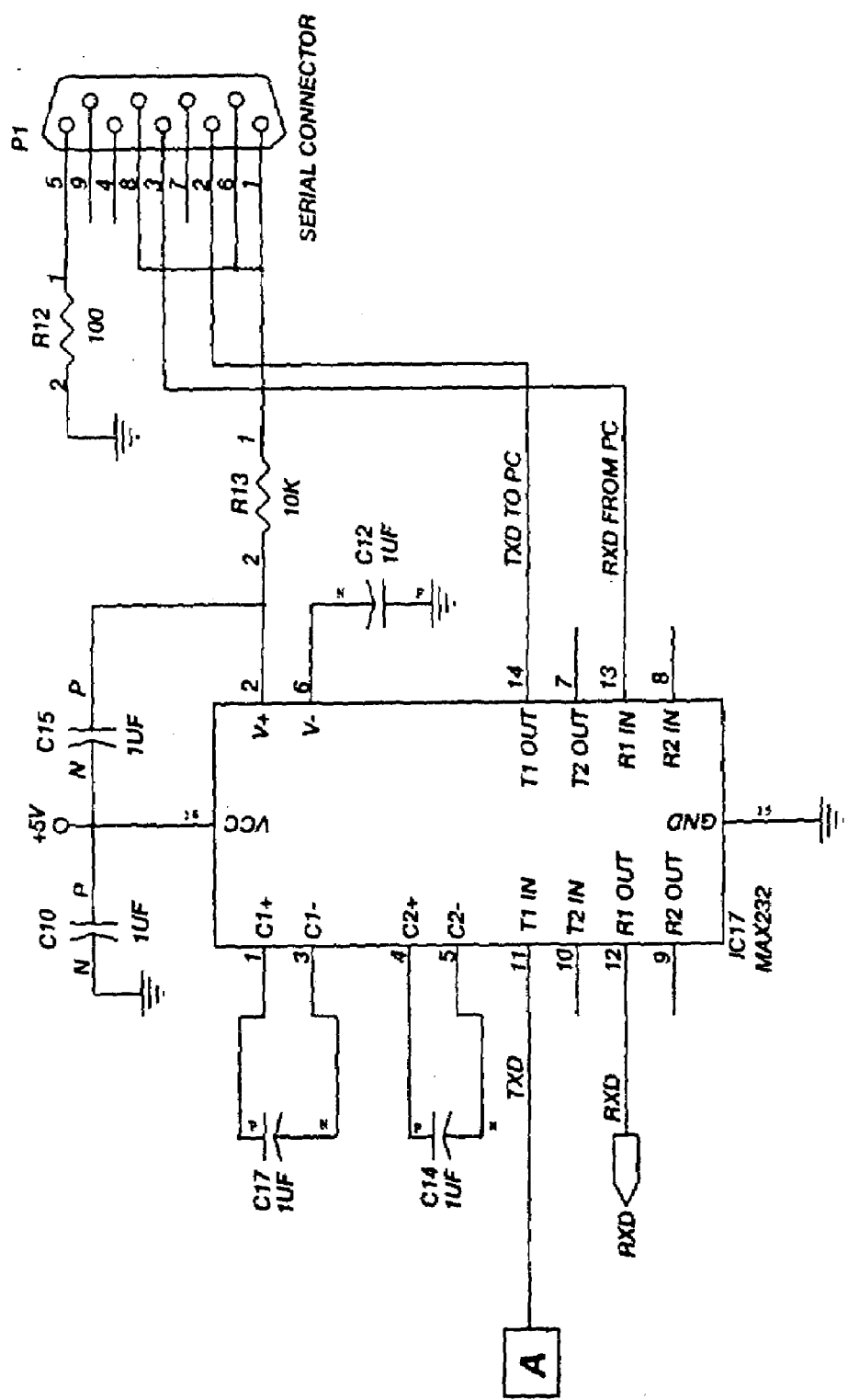
Figure 30L:
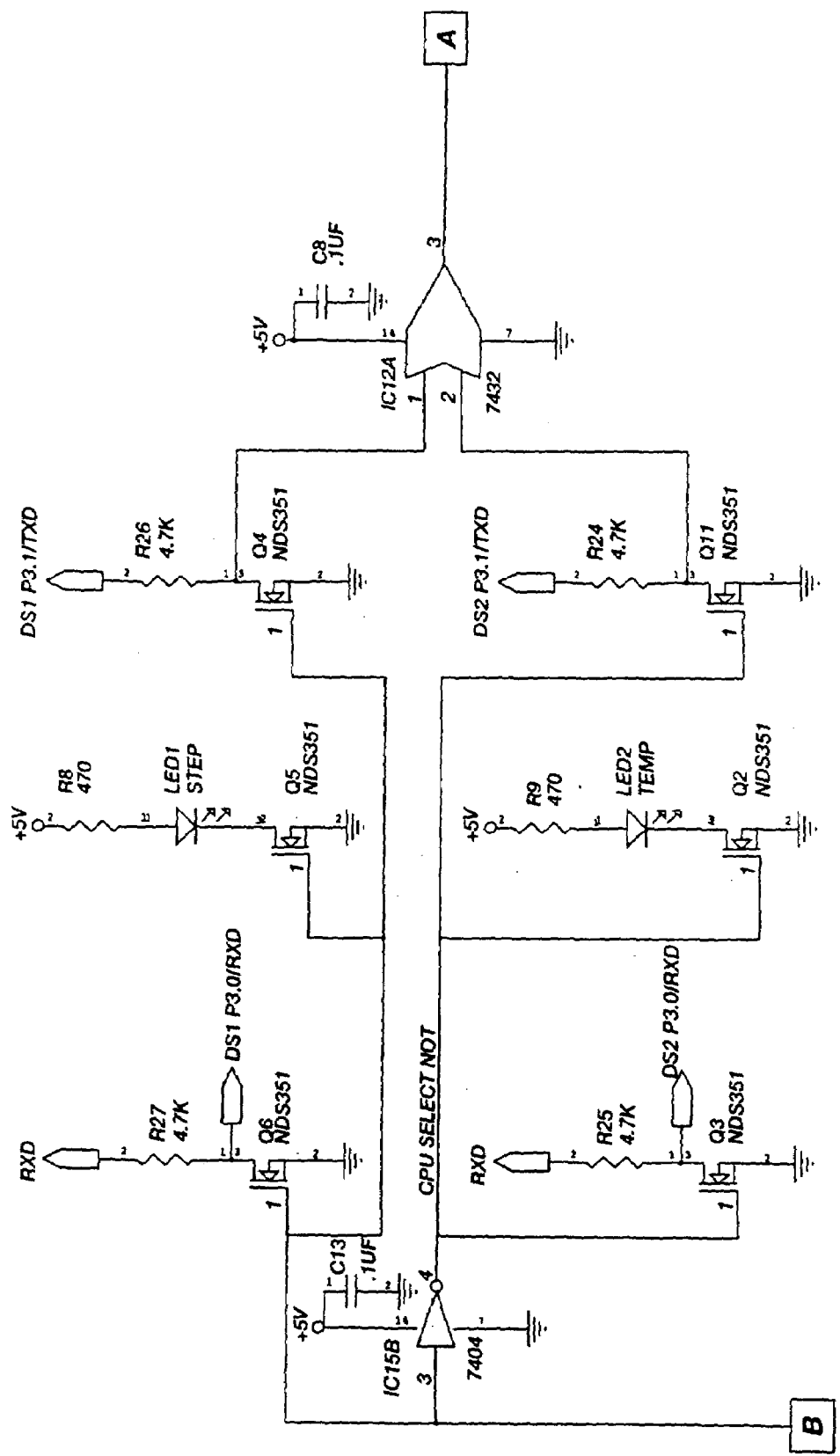
Figure 30M:
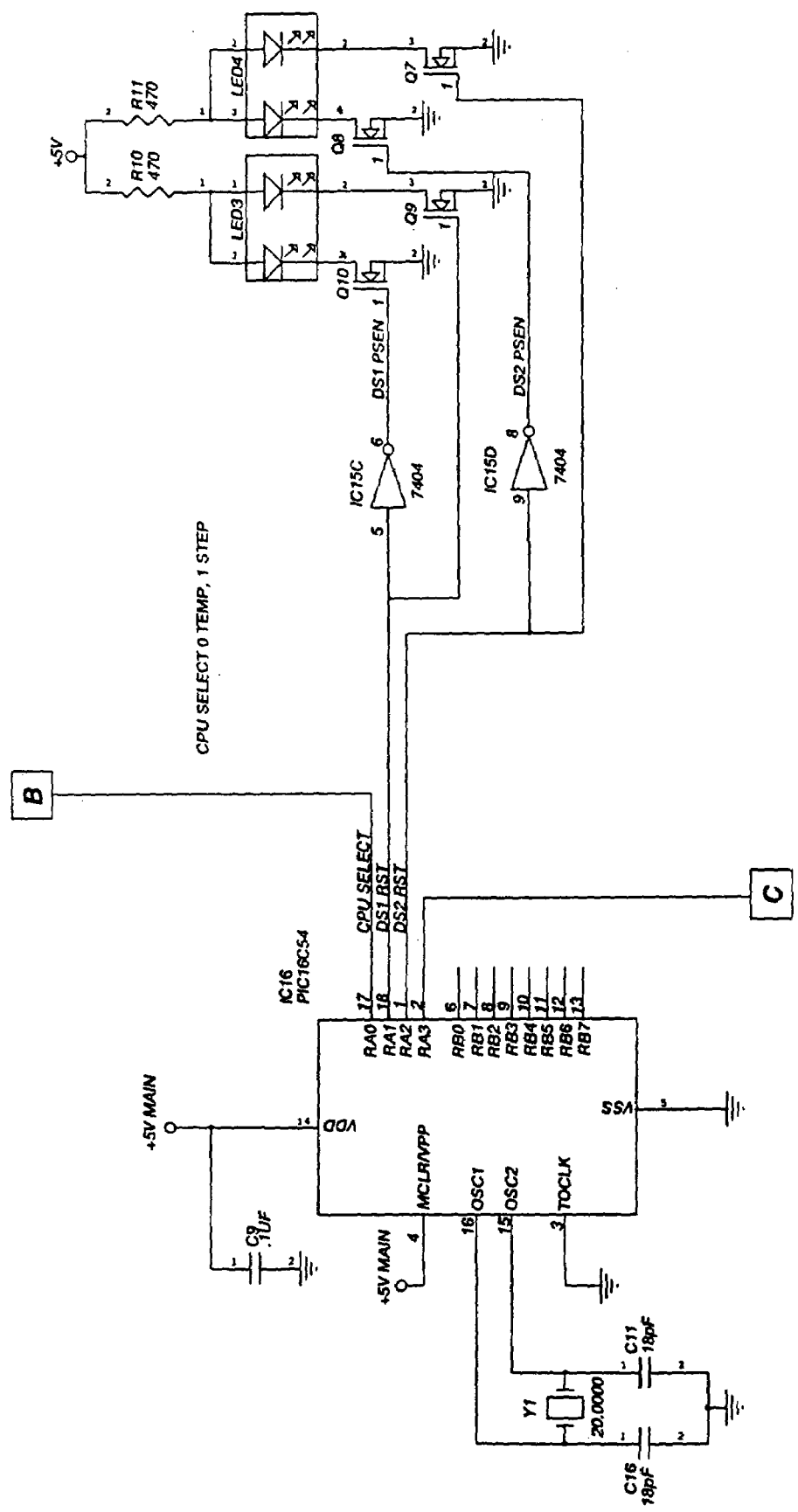
Figure 30N:
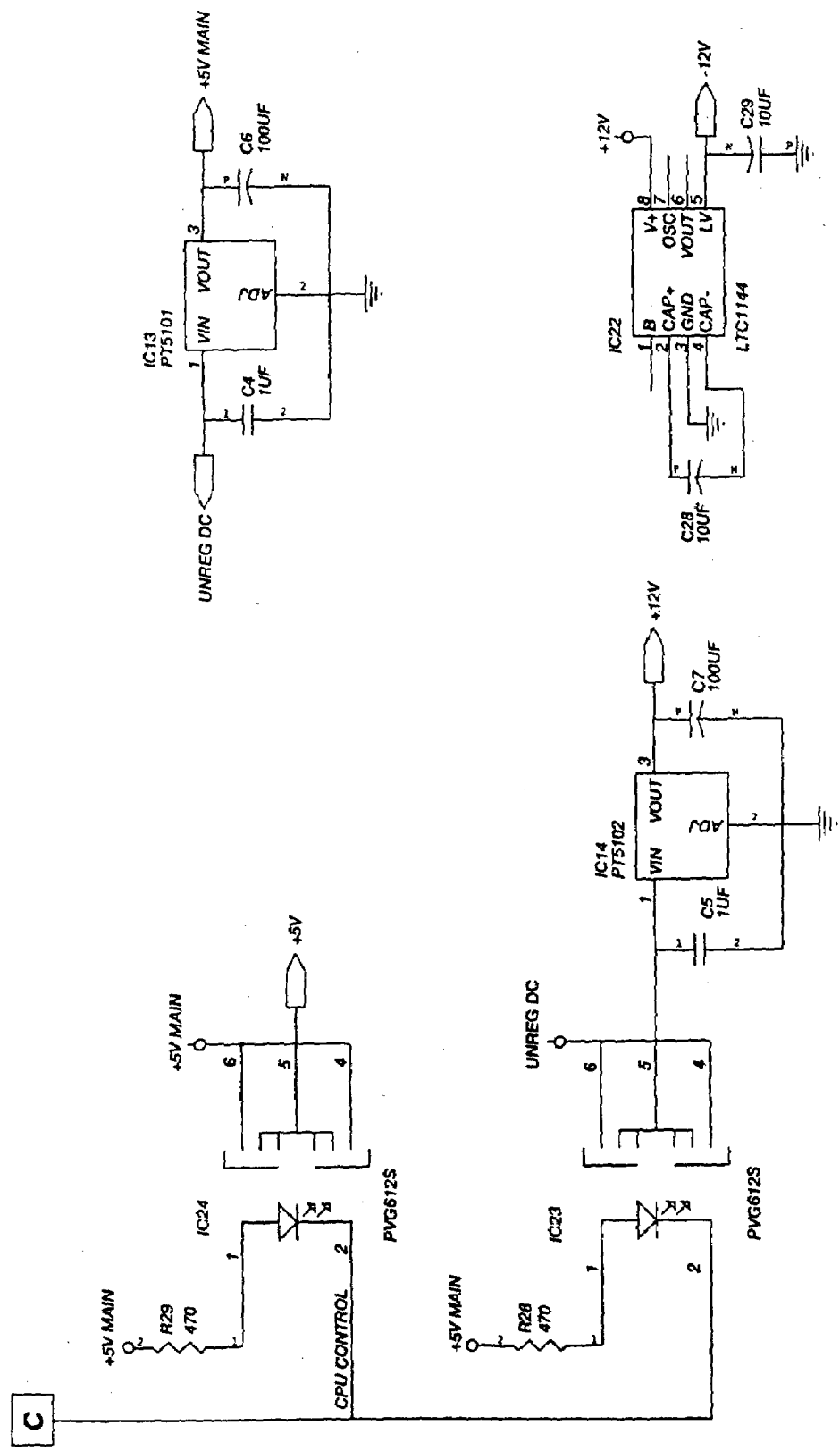
Figure 30O:
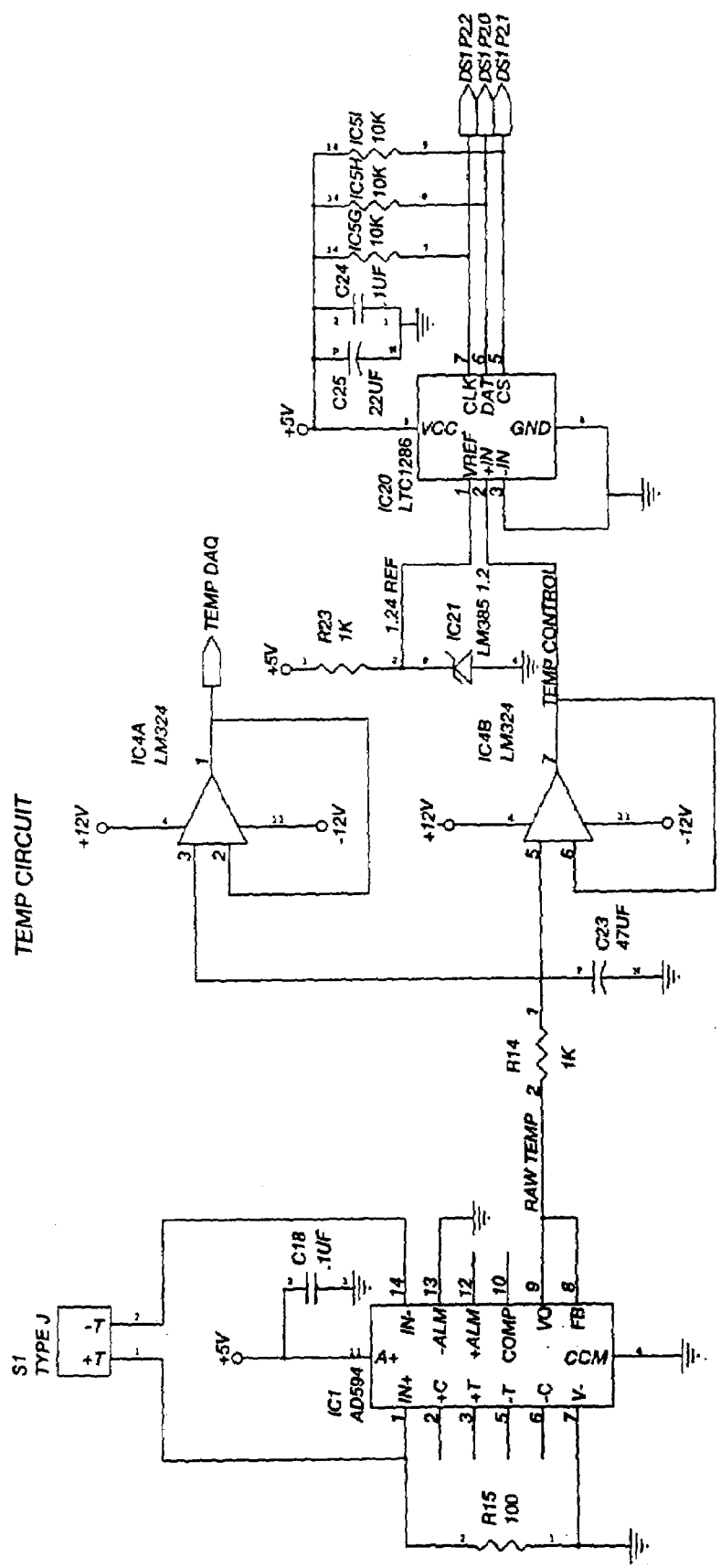
Figure 30P:
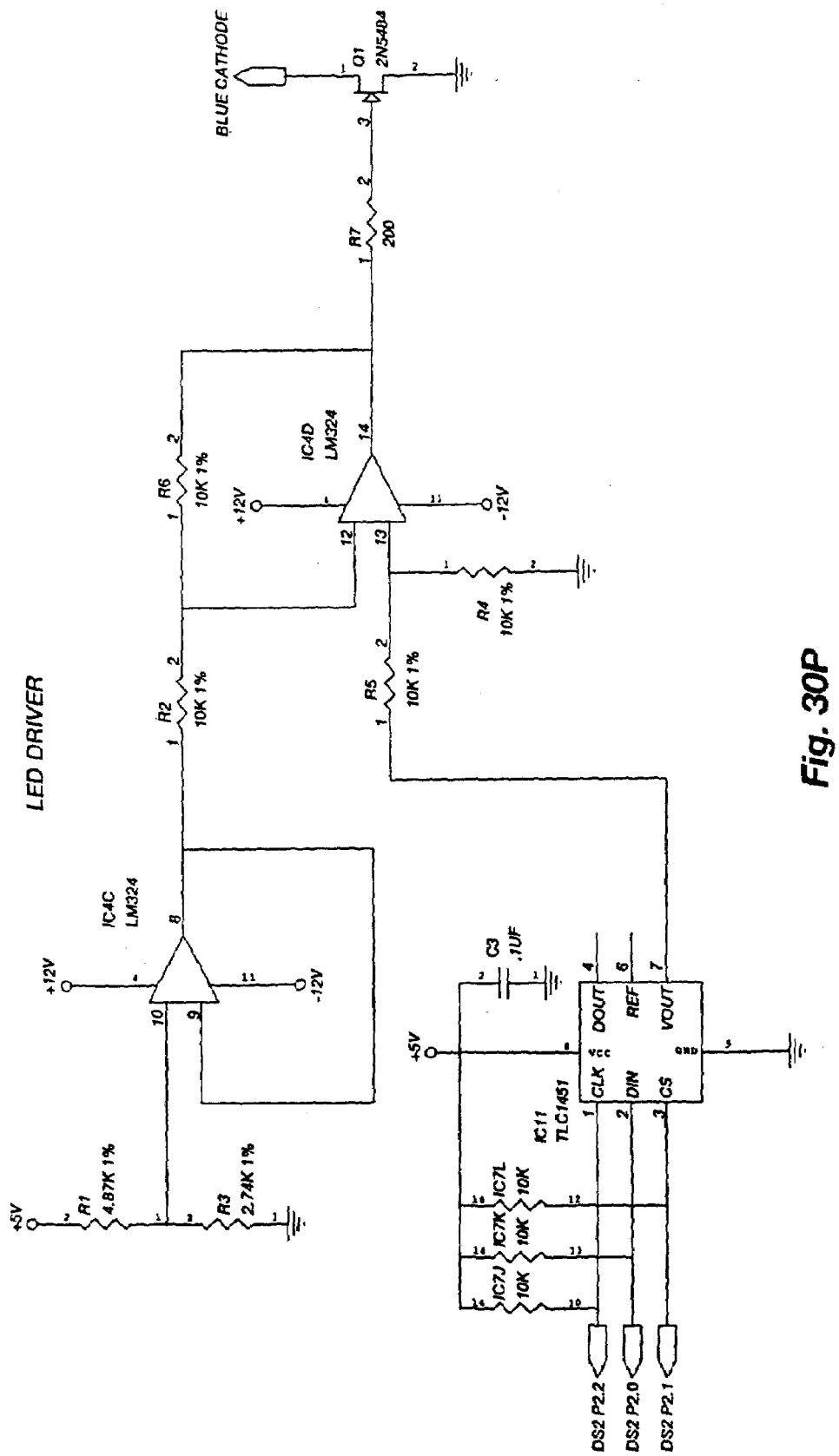
Figure 30Q:
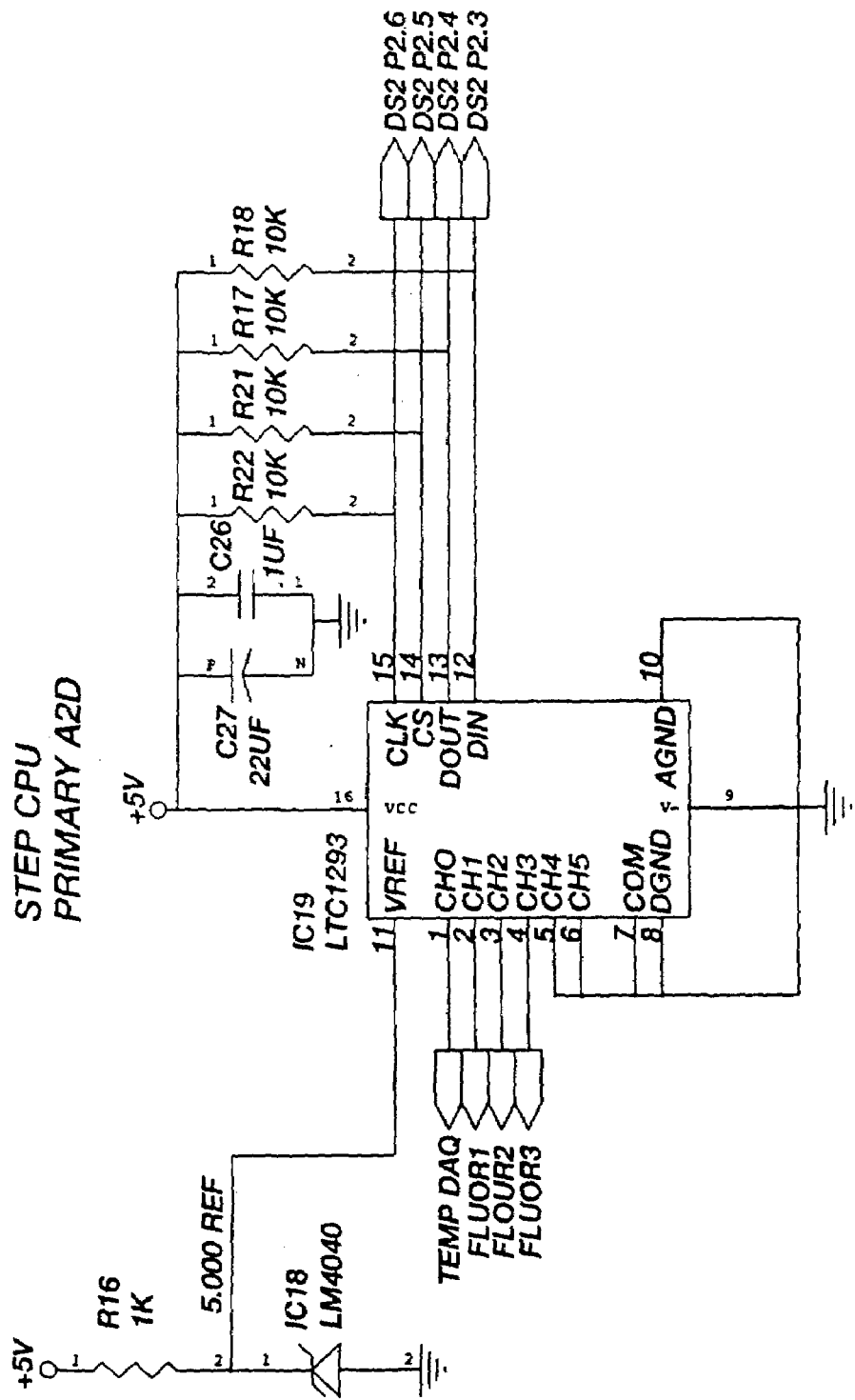
Figure 30R:
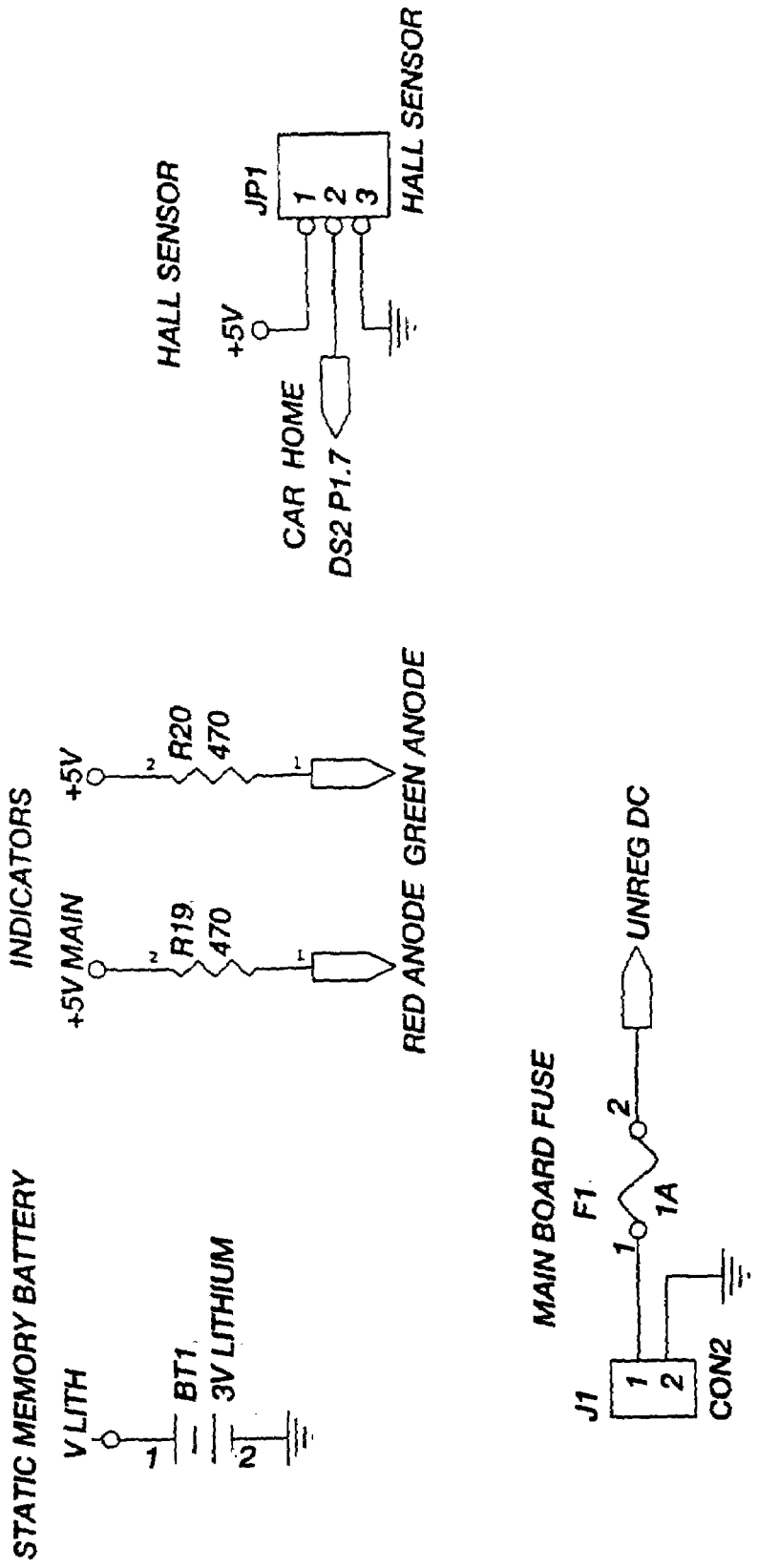
Figure 30S:
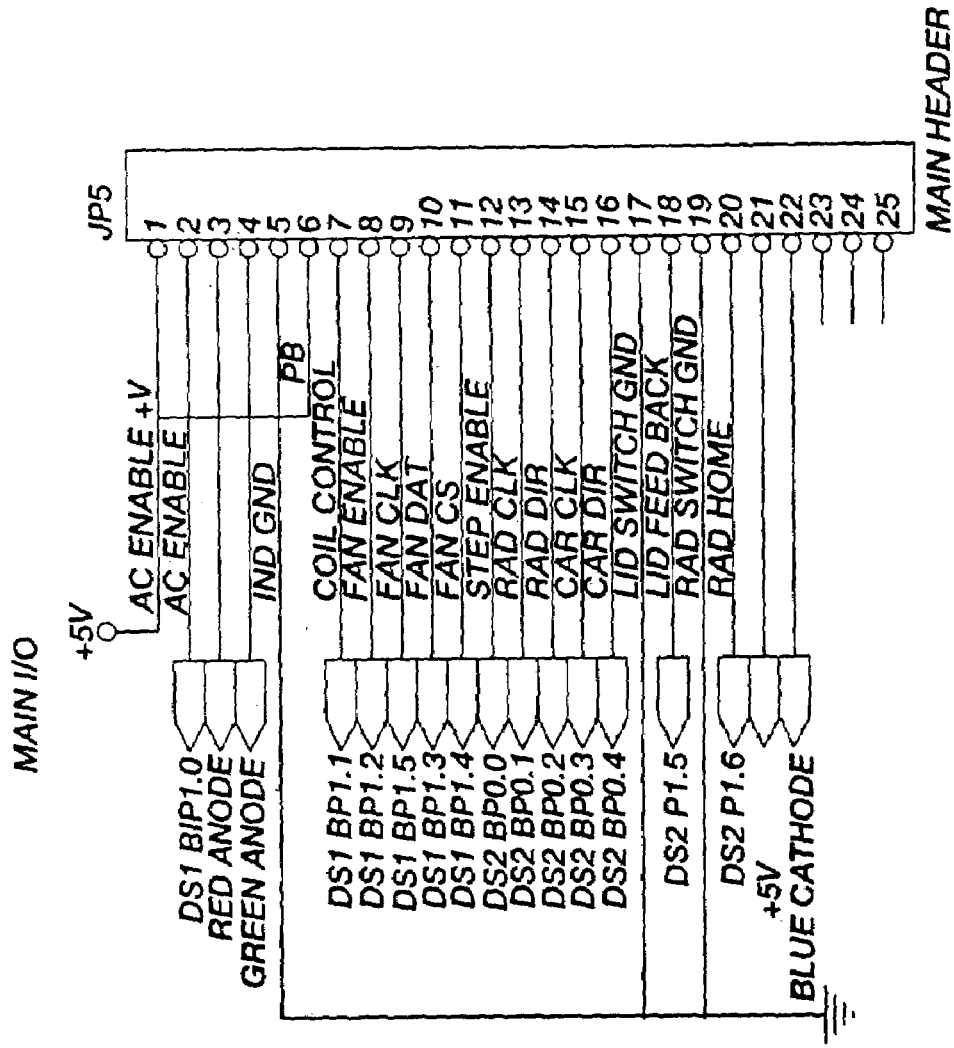
Figure 30T:
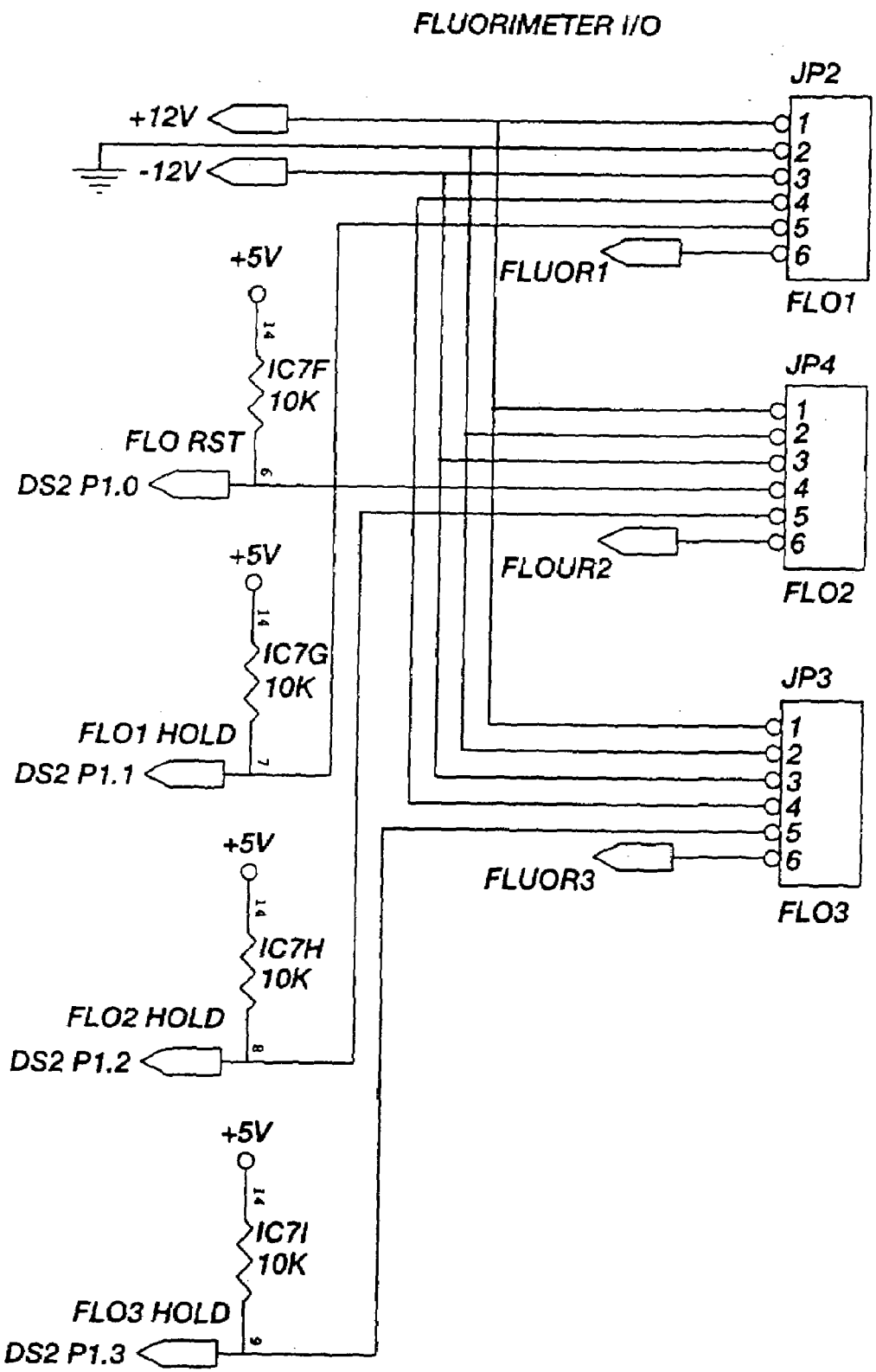
Figure 30U:
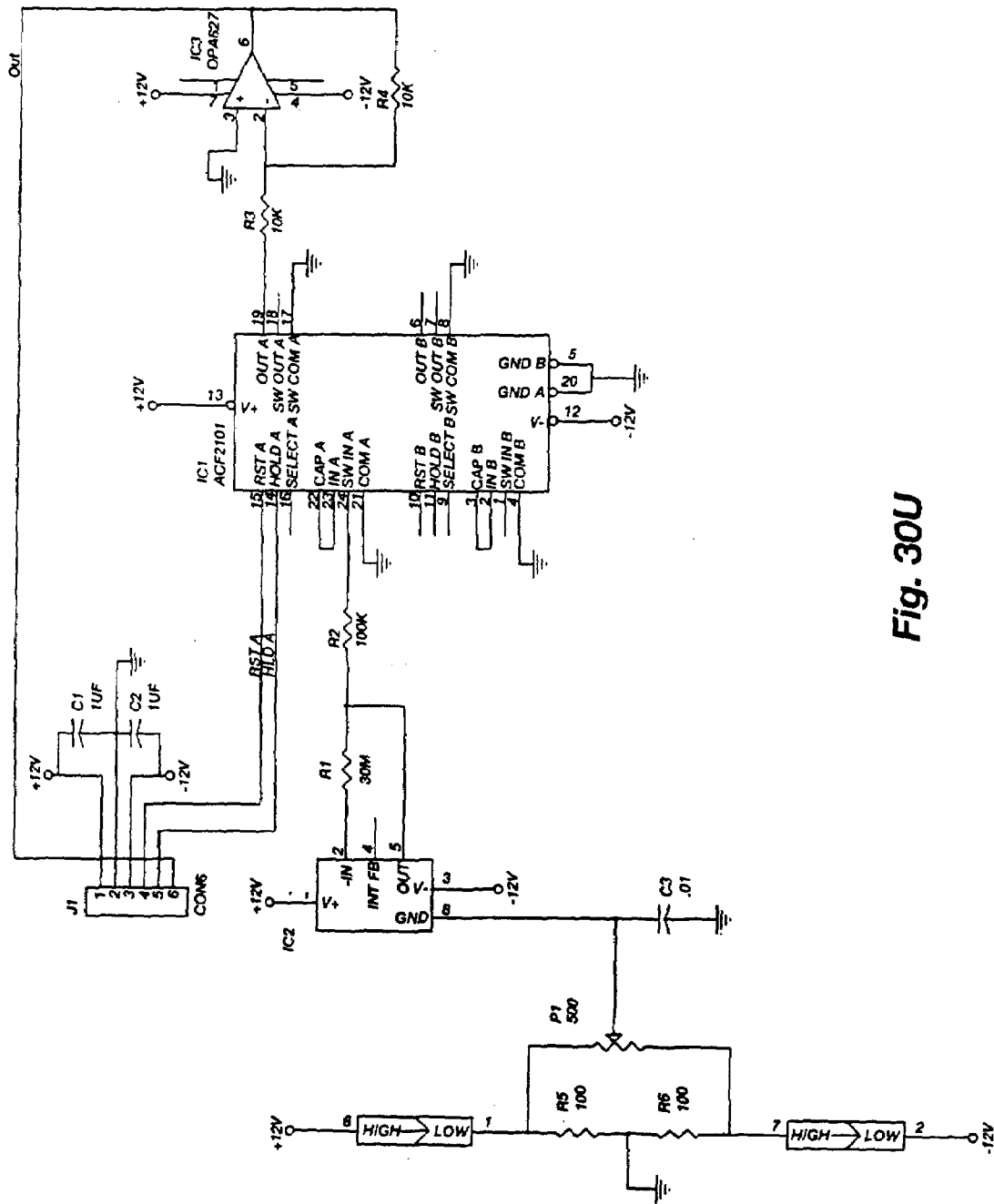
Figure 30V:
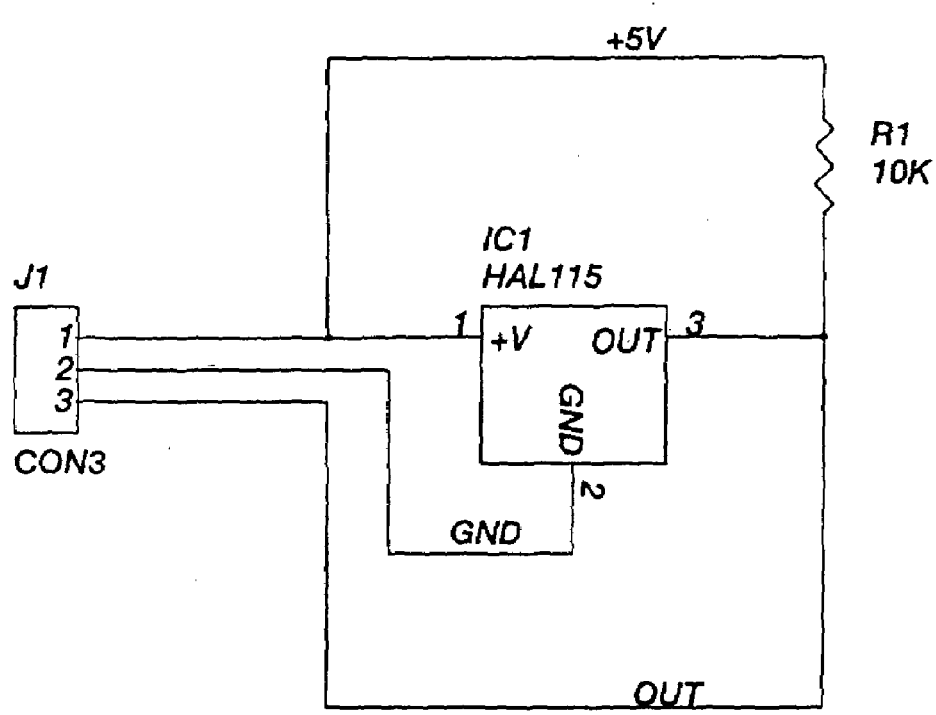

Provided in FIGS. 30A-V are detailed schematic diagrams showing the preferred configuration of the electrical components of the rapid temperature cycler 502 represented in FIGS. 28 and 29. It is to be understood that the diagrams of FIGS. 30A-V are merely one preferred arrangement for carrying out particular aspects of the present invention and these diagrams are not intended to be limiting of the scope of the present invention. In order to improve the clarity of the diagrams, the notations which are commonly used in the industry are maintained on these diagrams and are referenced in the corresponding parts list provided below.

Parts List - MAIN

| Item | Quantity | Reference | Part |
|---|---|---|---|
| 1 | 1 | BT1 | 3 V LITHIUM |
| 2 | 9 | C1, C2, C3, C8, C9, C13, C18, C24, C26 | .1 UF |
| 3 | 7 | C4, C5, C10, C12, C14, C15, C17 | 1 UF |
| 4 | 2 | C7, C6 | 100 UF |
| 5 | 6 | C11, C16, C19, C20, C21, C22 | 18 pF |
| 6 | 1 | C23 | 47 UF |
| 7 | 2 | C25, C27 | 22 UF |
| 8 | 2 | C28, C29 | 10 UF |
| 9 | 1 | F1 | 1 A |
| 10 | 1 | IC1 | AD594 |
| 11 | 2 | IC2, IC3 | DS5000FP |
| 12 | 1 | IC4 | LM324 |
| 13 | 8 | IC5, IC7, IC10, R13, R17, R18, R21, R22 | 10K |
| 14 | 2 | IC6, IC8 | MS62256 |
| 15 | 2 | IC9, IC10 | DS2003 |
| 16 | 1 | IC11 | TLC1451 |
| 17 | 1 | IC12 | 7432 |
| 18 | 1 | IC13 | PT5101 |
| 19 | 1 | IC14 | PT5102 |
| 20 | 1 | IC15 | 7404 |
| 21 | 1 | IC16 | PIC16C54 |
| 22 | 1 | IC17 | MAX232 |
| 23 | 1 | IC18 | LM4040 |
| 24 | 1 | IC19 | LTC1293 |
| 25 | 1 | IC20 | LTC1286 |
| 26 | 1 | IC21 | LM385 1.2 |
| 27 | 1 | IC22 | LTC1144 |
| 28 | 2 | IC23, IC24 | PVG612S |
| 29 | 1 | JP1 | HALL SENSOR |
| 30 | 1 | JP2 | FLO1 |
| 31 | 1 | JP3 | FLO3 |
| 32 | 1 | JP4 | FLO2 |
| 33 | 1 | JP5 | MAIN HEADER |
| 34 | 1 | J1 | CON2 |
| 35 | 1 | LED1 | STEP |
| 36 | 1 | LED2 | TEMP |
| 37 | 2 | LED3, LED4 | RED/GREEN LED |
| 38 | 1 | P1 | SERIAL CONNECTOR |
| 39 | 1 | Q1 | 2N5484 |
| 40 | 10 | Q2, Q3, Q4, Q5, Q6, Q7, Q8, Q9, Q10, Q11 | NDS351 |
| 41 | 1 | R1 | 4.87K 1% |
| 42 | 4 | R2, R4, R5, R6 | 10K 1% |
| 43 | 1 | R3 | 2.74K 1% |
| 44 | 1 | R7 | 200 |
| 45 | 8 | R8, R9, R10, R11, | 470 |

Parts List - MAIN (continued)

| Item | Quantity | Reference | Part |
|---|---|---|---|
| 46 | 2 | R19, R20, R28, R29 R15, R12 | 100 |
| 47 | 3 | R14, R16, R23 | 1K |
| 48 | 4 | R24, R25, R26, R27 | 4.7K |
| 49 | 1 | S1 | TYPE J |
| 50 | 1 | Y1 | 20.0000 |
| 51 | 2 | Y3, Y2 | 14.745600 |

Parts List - POWER BOARD

| Item | Quantity | Reference | Part |
|---|---|---|---|
| 1 | 3 | C1, C5, C6 | 330 UF |
| 2 | 1 | C2 | 47 UF |
| 3 | 1 | C3 | 1000 UF |
| 4 | 1 | C4 | 22 UF |
| 5 | 1 | C7 | 100 UF |
| 6 | 1 | C8 | 220 UF |
| 7 | 5 | C9, C10, C11, C12, C13 | .1 UF |
| 8 | 2 | C15, C14 | 10 UF |
| 9 | 2 | DR1, DR2 | IM481H |
| 10 | 1 | D1 | 1N5232 |
| 11 | 2 | D2, D4 | 1N4756 |
| 12 | 2 | D5, D3 | 11DQ06 |
| 13 | 1 | F1 | 2A |
| 14 | 4 | IC1, IC2, IC3, IC4 | HCPL2630 |
| 15 | 1 | IC5 | LM2574hv8 |
| 16 | 2 | IC7, IC6 | PVG612S |
| 17 | 1 | IC8 | MOC 3020 |
| 18 | 1 | IC9 | TLC1451 |
| 19 | 1 | IC10 | LM324 |
| 20 | 1 | IC11 | BRIDGE |
| 21 | 1 | IC12 | LTC1144 |
| 22 | 1 | JP1 | HEADER 14 |
| 23 | 2 | JP2, JP3 | 4 HEADER |
| 24 | 1 | JP4 | HEADER 12 |
| 25 | 2 | L2, L1 | 330 UH |
| 26 | 1 | Q1 | 4008 |
| 27 | 9 | R1, R2, R4, R5, R6, R7, R8, R9, R10 | 470 |
| 28 | 1 | R3 | 360 |
| 29 | 7 | R11, R13, R14, R16, R17, R18, R19 | 10K |
| 30 | 1 | R12 | 4.7K |
| 31 | 1 | R15 | 1K |
| 32 | 1 | R20 | 261 |
| 33 | 1 | R21 | 866 |
| 34 | 1 | R22 | 650 |
| 35 | 1 | R23 | 180 |
| 36 | 2 | S1, S2 | 110/220 |
| 37 | 1 | T1 | TRANSFORMER FLAT COMPACT |
| 38 | 1 | VR1 | LM2575 |

Parts List - INTEGRATOR

| Item | Quantity | Reference | Part |
|---|---|---|---|
| 1 | 2 | C1, C2 | 1 UF |
| 2 | 1 | C3 | .01 |
| 3 | 1 | IC1 | ACF2101 |
| 4 | 1 | IC2 | OPT301 |
| 5 | 1 | IC3 | OPA627 |
| 6 | 1 | IC4 | REF200 |
| 7 | 1 | J1 | CON6 |
| 8 | 1 | P1 | 500 |

Parts List - INTEGRATOR (continued)

| Item | Quantity | Reference | Part |
|---|---|---|---|
| 9 | 1 | R1 | 30 M |
| 10 | 1 | R2 | 100K |
| 11 | 2 | R3, R4 | 10K |
| 12 | 2 | R5, R6 | 100 |

Parts List - HALL EFFECT

| Item | Quantity | Reference | Part |
|---|---|---|---|
| 1 | 1 | IC1 | HAL115 |
| 2 | 1 | J1 | CON3 |
| 3 | 1 | R1 | 10K |

Exemplary programming code used in connection with the components of FIGS. 28-30 is included in the Programming Code Appendix B attached hereto and incorporated herein by reference.

In accordance with another embodiment of the present invention a handling system is provided for loading small volume sample vessels with liquid samples, particularly samples to analyzed by detection of emitted fluorescence. The sample vessel typically has a volume of less than 1 ml, and it can be in the form of a tube (i.e. a capillary tube) or a "flat capillary" wherein the capillary space is defined by two spaced-apart plates or sheets sealed along their edges. The sample vessel typically has a volume to external surface area ratio of about 1 mm, more typically less than about 0.5. Capillary tubes having an inner diameter of less than 1 mm have a volume to surface area ratio of less than 0.25 mm. The vessel used in accordance with the present invention is preferably formed from an optically transparent material. Preferred materials are optically transmissible for light having a wavelength ranging from about 400 to about 800 nm. The use of such material will allow the detection of a fluorescent signal generated in a liquid sample held by the vessel. Moreover the use of vessels with a low volume to surface area ratio for analyzing fluorescence from a fluorescent sample enables more efficient detection of the fluorescence due to enhanced total internal reflection.

Vessels having a high surface area to volume ratio (or conversely, a low volume to surface area ratio) can be difficult to load with liquid samples. Advantageously, the sample handling system of the present invention helps to overcome such difficulties. In accordance with one embodiment a vessel having a high surface area to volume ratio and an open end is provided with a funnel cap that fits onto the open end of the vessel to facilitate loading of liquid samples into the vessel. The funnel cap includes a first sample receiving port and a second sample transfer port and means for releasably fixing the funnel cap on the vessel so that the sample transfer port of the funnel cap and the open end of the vessel are in alignment. In one embodiment the funnel cap is of plastic or rubber construction and is formed so that the inner diameter of the sample transfer port frictionally engages the outer diameter of the vessel proximal to its open end. However, other means of coupling the funnel cap to the vessel are know to those skilled in the art and are within the scope of the invention, including the use of adhesives, clamps, clasps and the like. In one embodiment the sample handling system further comprises a plug for frictional fit sealing engagement with the sample receiving port of the funnel cap. However any device or material that effectively seals the opening of the funnel to prevent contamination or evaporation of the loaded sample is suitable for use with the present invention.

Advantageously the vessels of the present invention can be used in a method for enhancing detection and efficiency of acquisition of fluorescence in a sample comprising a fluorophore. The method comprises the steps of placing a sample in a vessel having walls composed of an optically transparent material and defining a volume having at least first and second dimensions. The first dimension is less than the second dimension and the ratio of volume to external surface area of the vessel is less than 1 mm. Enhanced detection and efficiency of acquisition of fluorescence generated from the sample is achieved by detecting fluorescence along an axis substantially parallel to a wall along the second dimension of the vessel. In one embodiment, sample fluorescence is induced by fluorophore-excitatory illumination of the sample wherein the sample is illuminated along an axis substantially parallel to a wall along the second dimension of the vessel. In a preferred embodiment, optimum efficiency of fluorescence acquisition is achieved by fluorophore-excitatory illumination of the sample along the fluorescence detection axis (epifluorescent detection), and fluorescence is detected along an axis through a wall of the vessel having the smallest surface area, preferably along an axis through the bottom of the vessel.

In one embodiment, the fluorescence of the biological sample is temperature dependent. For example the vessel may contain a sample comprising nucleic acid sequences and the fluorescent entity may comprise a double strand specific dye. As the temperature of the sample is raised to the denaturation temperature, fluorescence intensity decreases. Alternatively the fluorescent entity may comprise a pair of oligonucleotide probes that hybridize to adjacent regions of a target nucleic acid sequence, wherein one of said probes is labeled with an acceptor fluorophore and the other probe is labeled with a donor fluorophore of a fluorescence energy transfer pair. In this embodiment the vessel and the sample can be heated while monitoring the fluorescence of at least one fluorophore of the fluorescence energy transfer pair.

In accordance with one embodiment the vessel is in the form of a capillary tube or flat capillary that can be used with advantage in procedures that require thermal cycling of a sample, for example, amplification of a target nucleic acid sequence by the polymerase chain reaction. In one embodiment the capillary vessel is formed to be inserted into a sample holder of a device used for thermal cycling or a device used to detect fluorescence. The sample holder of the device may hold only a single vessel, or the sample holder may be in the form of a carousel for holding a plurality of sample vessels.

Figure 31A:
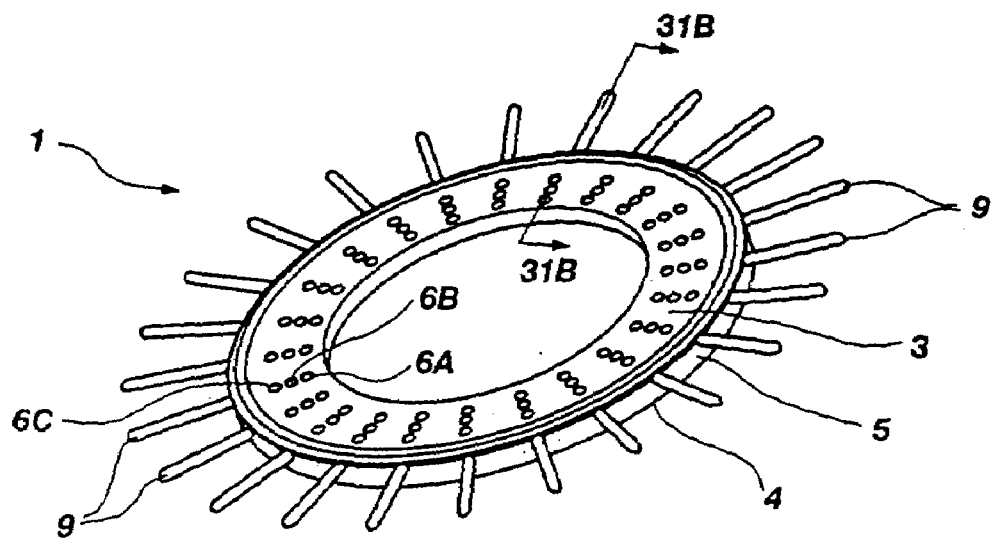
FIGS. 31A and 31B are perspective and cross sectional views, respectively, of a sample handling system in accordance with the present invention.
Figure 31B:
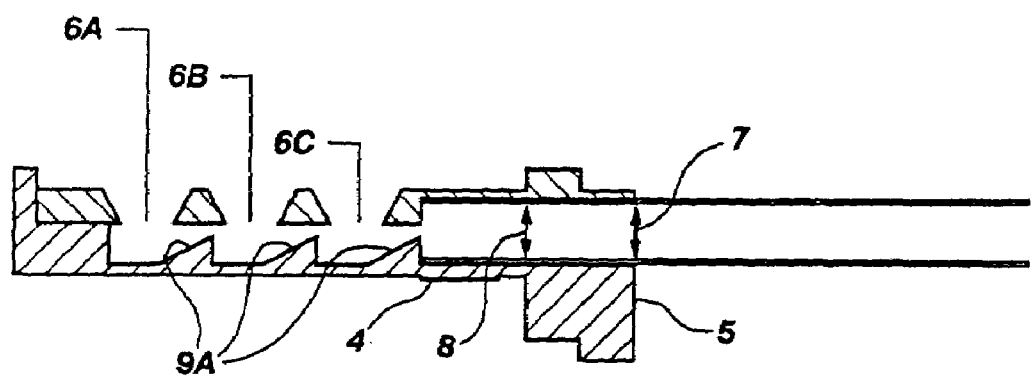

A carousel suitable for use in accordance with the present invention is shown in FIGS. 31A&B. The carousel 1 is generally in the form of a disc 2 having a top surface 3, a bottom surface 4 and an outer edge 5 extending therebetween. The disc 2 has a plurality of sets of radially aligned sample receiving ports 6A, 6B, and 6C in the top surface 3, a sample vessel port 7 in outer edge 5 and a sample passageway 8 communicating with the sample receiving ports 6A, 6B, and 6C and the respective sample vessel port 7. The carousel 1 is shown with fixed sample vessels, some of which are indicated at 9. The sample vessel port 7 and sample passageway 8 are formed for receiving and fixing sample vessel 9 to the disc 2. In one embodiment the sample vessel 9 is releasably fixed to the carousel 1 to allow the removal of the sample vessel and its replacement with another sample vessel to allow for multiple use of the carousel 1. In an alternative embodiment the sample vessels 9 are permanently fixed to, or formed as an integral component of, the disc 2. In one embodiment the sample vessel 9 is fixed to the disc 2 by frictional contact between the sample vessel 9 and at least a portion of the sample passageway 8 proximal to said sample vessel port 7. Other conventional means for fixing the sample vessel in communication with the sample vessel can be used. For example, complementary screw threads can be formed on the surface of the sample passageway 8 and on the exterior surface of the sample vessel 9. In addition adhesives or any other fixation means known to those skilled in the art can be used in accordance with the present invention to fix the sample vessel 9 to the disc 2. The top and bottom surfaces of the carousel of the present invention are preferably formed to allow multiple carousels to be stacked one on top of another so that a stack of multiple carousels can be releasably engaged with a motor drive shaft and rotated simultaneously as a unit as shown in FIG. 32.

Figure 32:
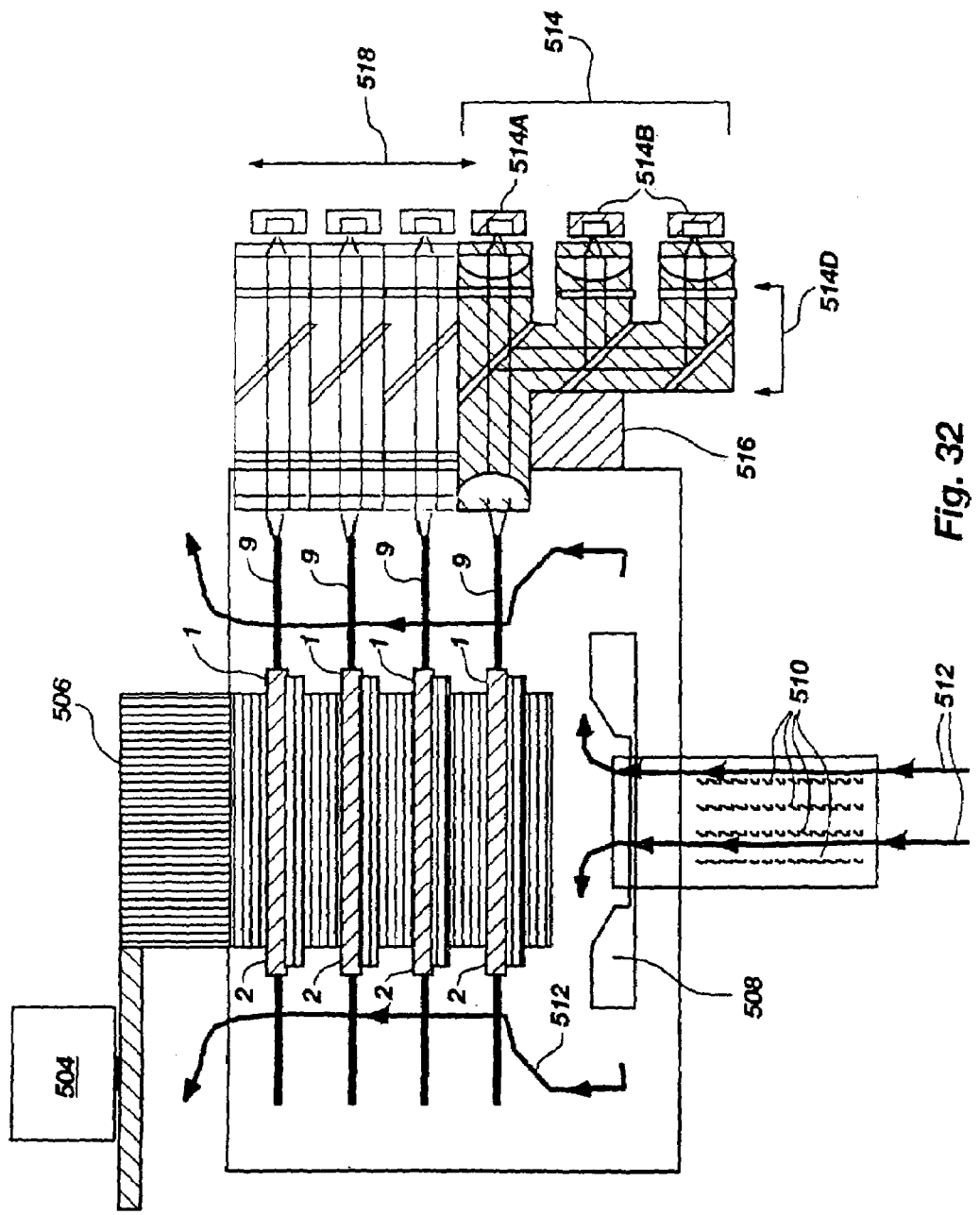
FIG. 32 is a schematic representation of another embodiment of the present invention which accommodates multiple sample handling trays.

The embodiment shown in FIG. 32 includes a stepper motor 504 and a drive shaft 506 which functions to hold and rotate the carousels generally indicated at 1. A chamber fan 508 is used to generate the air flow indicated by the arrows 512. A heating device 510 functions to heat the air which passes by the sample vessels 9. A fluorimeter assembly 514 includes an LED source 514A, photodiodes 514B, focusing lenses 514C, and a filter assembly 514D. A fluorimeter stepper motor 516 functions to move the fluorimeter assembly 514 in the direction of arrow 518. Those skilled in the art can readily fabricate embodiments of the present invention fashioned after the arrangement represented in FIG. 32 using the information set forth herein.

In another embodiment (not shown) the carousel comprises a disc having a top surface, a bottom surface, an outer edge extending therebetween, a sample receiving port in the top surface, a sample vessel port in the bottom surface and a sample passageway communicating with said sample receiving port and the sample vessel port. The sample vessel port and sample passageway are formed for receiving and fixing a sample vessel to the disc. Preferably the sample vessels are held at a radially extending acute angle to the bottom surface of the disc.

In one embodiment the sample passageway of the disc comprises a first portion having a central axis substantively parallel to the top and bottom surfaces of the disc and a second portion having a central axis forming an acute angle with the top and bottom surfaces of the disc. In this embodiment the sample vessel port and sample passageway are formed for receiving and fixing a sample vessel to the disc such that the sample vessel extends from the disc at an acute angle relative to the bottom surface of the disc.

Carousel 1 is further provided with means for closing the sample receiving ports 6A, 6B, and 6C. The closure means can be a plug (not shown) that fits into the sample receiving port 6 and frictionally engages the adjacent walls of the sample passageway, or for example, adhesive backed tape, for application to the top surface to effectively seal the opening of the sample receiving port to prevent contamination or evaporation of a loaded sample. Carousel 1 is releasably engaged with a drive shaft for rotation. Any suitable engagement means well known to those of ordinary skill in the art can be used including frictional engagement, or the use of screws, bolts, locking pins or clamps. In one embodiment, the disc 2 is formed as ring having a center hole formed for receiving a drive shaft (see 506 in FIG. 32). The end of the drive shaft is preferably provided with structures for holding the discs 2 in place.

The carousel 1 of the present invention can be used to deliver a liquid sample to a sample vessel 9. In one embodiment the sample vessel 9 is a capillary vessel containing a predetermined mixture (for example a reagent mixture) that interacts with one or more components of the introduced sample. In accordance with one embodiment the predetermined mixture is added to the sample vessel before positioning a capillary sample vessel into the sample vessel port. Alternatively the sample vessel is prepackaged with a predetermined mixture. The predetermined mixture may comprise reagents that react or interact with the sample to produce a detectable signal or to produce a derivative product.

The sample passageway 8 of the carousel 1 are optionally provided with one or more barriers 10 that prevent a liquid sample delivered through sample receiving ports 6A, 6B, and 6C from flowing to the sample vessel port 7 absent a biasing force on said liquid sample. The term "barrier" is used herein to include any structure that impedes the free flow of a liquid sample delivered into a sample receiving port to the sample vessel port. Examples of suitable barriers for use in the sample passageway of the carousel of the present invention include depressions or wells formed in the sample passageway, sample passageway narrowing projections or annular rims that extend from the surface of the sample passageway, porous membranes, directional valves, or flaps that are biased in a closed position.

The barriers are formed so that the liquid sample can overcome the barrier by application of a biasing force on a liquid sample present in the sample passageway and blocked by the barrier. The application of biasing force on the sample is preferably provided by the centripetal force generated by rotation of the carousel. Therefore, in a carousel having a plurality of sets of sample receiving ports 6A, 6B, and 6C in the top surface, each set with a corresponding sample passageway and sample vessel port, samples can be added individually to the various sample receiving ports and the barrier will localize the liquid sample and prevent the samples from flowing to the respective sample vessel ports. After all of the samples are delivered into the respective receiving ports, the carousel is rotated to deliver the samples to the respective sample vessel port and into an attached sample vessel.

In accordance with one embodiment, each sample passageway of the carousel communicates with a single sample vessel port and a plurality of sample receiving ports. In accordance with that embodiment, the sample passageway can optionally include a central passageway that branches to communicate with multiple sample receiving ports, or alternatively, as illustrated in FIGS. 31A&B multiple sample receiving ports 6A, 6B, and 6C are aligned along a common axis that extends radially from the center of the disc, each of said ports communicating through one passageway with a sample vessel received in the sample vessel port. The sample passageway can be provided with one or more barriers 9A that prevent a sample added to any one of the plurality of sample receiving ports from flowing to the sample vessel port absent a biasing force on said liquid sample. Furthermore, each sample passageway can be provided with multiple barriers, each of which require a different amount of biasing force to transfer a sample over the barrier. In accordance with this embodiment, after delivery of the samples to the respective sample receiving ports, individual samples can be selectively transferred to the sample vessel port and into the sample vessel by controlling the rate of rotation of the carousel.

For example, a first sample can be delivered into a first sample receiving port and a second sample can be delivered to a second sample receiving port wherein the first and second sample receiving ports communicate with a common passageway and the first and second sample receiving ports are each provided with a barrier that prevents flow of the respective first and second sample. The barriers allow the disc to be provided as part of a kit with predetermined amounts of selected reagents, catalysts, enzymes, oils, etc. being preloaded into the sample passageway via one or more of the sample receiving ports.

In one embodiment the barrier for the second sample receiving port is formed so that a greater biasing force must be applied to the sample delivered to the second sample receiving port to pass its associated barrier than is required for a sample delivered to the first sample receiving port to pass its associated barrier. In accordance with this embodiment, rotation of the carousel at a first rate will deliver the first sample to the sample vessel port and into the sample vessel, while the second sample is prevented from flowing to the sample vessel port and into the sample vessel. Rotation at a increased second rate will then enhance the centripetal force on the second sample and result in the delivery of the second sample to the sample vessel port and into the sample vessel. Based on this principle, different samples can be delivered to multiple sample vessel ports that communicate with a common passageway and after all the samples have been loaded, the individual samples can be delivered to the sample vessel port and into the sample vessel one at a time or simultaneously by controlling the rate of rotation of the carousel. In one embodiment a first sample, comprising a fluorophore is added to a first sample vessel port and a second sample comprising oil is delivered to the second vessel port. The carousel is rotated to deliver the first sample into the sample vessel followed by the oil. The oil (or another liquid that effectively seals the first sample within the sample vessel) functions both to decrease evaporation of the first sample and to reduce the risk of contamination of the first sample.

In one example a multiple sample carousel is used to handle multiple samples simultaneously. The carousel is a disc-like structure having a multiplicity of sample receiving ports in the top surface of the disc structure and in fluid communication with corresponding sample vessels attached to the disc. Samples added to the sample receiving ports are transferred to their corresponding sample vessels by rotation of the carousel. The carousel can also have multiple sample receiving ports communicating with each individual sample vessel. Reagents can be placed by the user into a second sample receiving port that communicates with the sample vessel for delivery to the vessel with another sample that was added to the first sample receiving port, or alternatively, predetermined reagents may be located in a second sample receiving port by the manufacturer; i.e. where the carousel, the sample vessels and the predetermined reagent are in a prepackaged form. The reagents, with the sample, are delivered to the sample vessel by rotation of the carousel. An oil for overlay of an aqueous sample may be placed in a third sample receiving port that is in liquid communication with the sample vessel (and the first and second sample receiving ports), or the oil may be added to the carousel by the manufacturer.

Alternatively, a sample, reagents and oil for sample overlays can be delivered to a single sample receiving port.

The carousel can be rotated to deliver each composition or sample to the respective vessel before a second or subsequent sample or other composition is delivered to the sample receiving port.

One preferred sample vessel carousel of this invention includes three sample receiving ports preferably, but optionally, arranged in radial alignment and in fluid communication with a common sample vessel. In accordance with this embodiment, about 1 to about 5 µl of an oil overlay, preferably dyed black, is present in prepackaged form, or delivered to the radially innermost sample receiving port. The oil overlay comprises mineral oil and about 0.01% to about 1% organic black dye such as Waxoline® Black OBP available from Zenica, Inc. of Wilmington, Del. About 1 to abut 9 µl of a reagent master mix is present in prepackaged form or is delivered to the radially outer most sample receiving port. The reagent master mix comprises a portion of, or all the necessary reaction components. A liquid sample containing the template nucleic acid to be tested is delivered manually or robotically into the radially intermediate sample receiving port. The disc is then rotated at a rate that transfers the sample to the reagent compartment, but at a rotated rate insufficient to deliver the mixture into the sample vessel. The sample and reagent can optionally be mixed by rapid changes in the rate of the rotation of the disc. The disc is then rotated at a higher rate that causes the sample and reagent mixture, but not the oil, to move into the sample vessel. The disc is then rotated at still a higher rotation rate to deliver the oil overlay to the sample vessel. The oil will overlay the aqueous sample because of its lower density and will block light passage because of its dye content. The selective transfer of oil, reagents and sample by altering the rate of carousel rotation is achieved by a combination of: 1) varying the diameter of the fluid communication passageways; 2) varying the size or shape of the physical barriers present in the fluid communication passageways; and 3) by using the dependence of centrifugal force on the varying distance (radius) of each sample receiving port from the center of the disc.

The carousel of the present invention can be releasably engaged with the drive shaft and a motor (506 and 504, respectively in FIG. 32) for rotating the carousel. Furthermore, individual carousels of this invention can be stacked upon one another and engaged with a drive shaft for simultaneous rotation (as shown in FIG. 32). In accordance with another aspect of the present invention a device is provided for monitoring the fluorescence of a sample held within a sample vessel (see 514 in FIG. 32). The sample vessel comprises an optically transparent material and has walls defining a volume having at least first and second dimensions wherein the first dimension is less than the second dimension and wherein the ratio of volume to external surface area of the vessel is less than 1 mm. In one embodiment the device comprises a chamber, a sample vessel holder, a light emitting source mounted in said chamber and positioned to illuminate the sample vessel along an axis substantially parallel to a wall along the second dimension of the vessel and a light detector mounted in said chamber and positioned to measure fluorescence from the sample vessel along an axis substantially parallel to a wall along the second dimension of the vessel. The light emitting source and the light detector in accordance with one embodiment are mounted on a platform that can be raised and lowered (as indicated by arrow 518 in FIG. 32). In this embodiment, the light emitting source and the light detector can be positioned to measure fluorescence from the sample vessels (along an axis substantially parallel to a wall along the second dimension of the vessel) of multiple carousels when individual carousels are stacked upon one another and engaged with a drive shaft for simultaneous rotation (see FIG. 32).

In one embodiment the sample vessel holder comprises a carousel for holding a plurality of capillary tubes, and the carousel is rotatably mounted in said chamber. The light emitting source is positioned to illuminate the capillary tube through the bottom of the tube and the light detector is mounted to detect fluorescence through the bottom of the capillary tube. In addition the device is provided with a stepper motor for rotating said carousel and means for coupling the carousel to the motor.

In accordance with one preferred embodiment, the chamber of the fluorescence detecting device is further provided with a heater (see 510 in FIG. 32) and a fan (see 508 in FIG. 32) mounted in said device and in air flow communication with the chamber, and a controller therefor, for rapidly cycling the temperature of the chamber using, at least initially, predetermined time and temperature parameters. The device is capable of conducting polymerase chain reactions in the sample vessels held by the carousel. In particular the device allows for an improved method of conducting PCR reactions because the progress of the reaction can be monitored in real time, and thus allow the adjustment of temperature and time parameters during the course of the reaction to optimize the yield and purity of the amplified target nucleic acid sequence.

Further, in accordance with the present invention, there is provided an improved method of amplifying a targeted nucleic acid sequence of a biological sample comprising the steps of adding to the biological sample an effective amount of two nucleic acid probes that hybridize to adjacent regions of the target sequence, one of said probes being labeled with an acceptor fluorophore and the other probe labeled with a donor fluorophore of a fluorescence energy transfer pair such that upon hybridization of the two probes with the target sequence, the donor and acceptor fluorophores are within 0 to 15 nucleotides, and more preferably within 1-5 nucleotides of one another, amplifying the targeted nucleic acid sequence using polymerase chain reaction, illuminating the biological sample with a selected wavelength of light that is absorbed by said acceptor fluorophore during the polymerase chain reaction monitoring fluorescent emissions from said sample, and adjusting the temperature and time parameters in accordance with the data generated from the monitoring step.

Thus in accordance with the present invention an improved device is provided for conducting PCR reactions. The device comprises a chamber, a heater and a fan mounted in said device and in air flow communication with the chamber, carousel for holding a plurality of sample vessels. The sample vessels used in conjunction with this device comprise an optically transparent material and walls defining a volume having at least first and second dimensions wherein the first dimension is less than the second dimension and wherein the ratio of volume to external surface area of the vessel is less than 1 mm. The carousel is rotatably mounted in the chamber. The device further comprises a light emitting source mounted in said chamber and positioned to illuminate at least one of the sample vessels along an axis substantially parallel to a wall along the second dimension of the vessel and a light detector mounted in said chamber and positioned to measure fluorescence from at least one of the sample vessels along an axis substantially parallel to a wall along the second dimension of the vessel. Furthermore, the device can be equipped with a stepper motor for rotating the carousel to position the respective capillary tubes held by said carousel for illumination and fluorescence detection. Monitoring the PCR reaction in real time and determining at least one reaction parameter in accordance with the detected fluorescence allows for the adjustment of the reaction conditions to optimize the reaction. In a preferred embodiment one or more values representative of the status of the reaction are displayed in a visually perceptible manner in real time.

The carousel of the present invention can also be used for delivering a liquid sample to a capillary sample vessel. The carousel comprises a disc having a top surface, a bottom surface and an outer edge extending therebetween, a sample receiving port in the top surface, a sample vessel port in the outer edge and a sample passageway communicating with the sample receiving port and the sample vessel port. The sample vessel port and the sample passageway are formed for receiving and fixing a sample vessel to the disc. The method of using the carousel to deliver a liquid sample to a capillary sample vessel comprises the steps of selecting a carousel for receiving a liquid sample and holding a sample vessel, delivering the liquid sample into the sample receiving port of the carousel, positioning a capillary sample vessel into the sample vessel port, and rotating the carousel to deliver the sample into the capillary sample vessel.

The present invention is also directed to a system for detecting the presence of a target nucleic acid sequence in a sample. The system comprises a pair of oligonucleotide probes that hybridize to adjacent regions of the target nucleic acid sequence, wherein one of said probes is labeled with an acceptor fluorophore and the other probe labeled with a donor fluorophore of a fluorescence energy transfer pair. Preferably, the donor fluorophore emission and the acceptor fluorophore absorption overlap less than 25%, the acceptor fluorophore has a peak extinction coefficient greater than 100,000 $M^{-1}$ $cm^{-1}$ and upon hybridization of the two probes with the target sequence, the donor and acceptor fluorophores are within 15 nucleotides of one another. In another embodiment the donor fluorophore emission and the acceptor fluorophore absorption overlap less than 20% and upon hybridization of the two probes with the target sequence, the donor and acceptor fluorophores are within 5 nucleotides of one another, and more preferably within 3 nucleotides of one another.

In view of the foregoing, it will be appreciated that the present invention provides an apparatus for accurately submitting biological samples to thermal cycling and for quickly and accurately varying the temperature of biological samples, most advantageously adjusting one or more reaction parameters in real time or according to a predetermined temperature versus time profile. The present invention also provides an apparatus suitable for subjecting a number of different biological samples to rapid thermal cycling and also provides a thermal cycling apparatus having a thermal transfer medium of low thermal mass which can effectively subject samples to a large temperature gradient over a very short period of time.

Moreover, the present invention provides an apparatus which can subject a biological sample to rapid thermal cycling using air as a thermal transfer medium and which provides a system and method for performing PCR rapidly and for simultaneously monitoring the reaction. Still further, the present invention also provides a system and method for performing PCR rapidly and also continuously monitoring the reaction while it is ongoing and for adjusting the reaction parameters while the reaction is ongoing.

Information regarding an On-line DNA Analysis System with Rapid Thermal Cycling is found in U.S. patent application Ser. No. 08/381,703 filed Jan. 31, 1995 which is now incorporated herein in its entirety.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A container for holding a fluidic biological sample while undergoing nucleic acid amplification, the container consisting of:
   a receiving portion having a first volume, the receiving portion being adapted to receive the biological sample therein; and
   a reaction portion consisting of a capillary tube that is closed at one end, has an inner diameter selected from the range of about 0.25 mm to about 1.0 mm, and a capillary tube wall about 0.1 mm thick, said reaction portion being in fluidic communication with the receiving portion such that the biological sample placed in the receiving portion can travel to the reaction portion, the reaction portion having an internal volume not greater than a second volume, the second volume being less than the first volume and not greater than 1 milliliter, said reaction portion comprised of material having a thermal conductivity in the range from about 20 to about 35 in accordance with the formula:

$$\left(\frac{\text{cal cm}}{\text{cm}^2\text{s degree C.}}\right) \times 10^4.$$

2. A container as defined in claim 1 wherein the receiving portion is formed from a plastic material.

3. A container as defined in claim 2 wherein the receiving portion is in the shape of a funnel structure.

4. A container as defined in claim 1 wherein the capillary tube is a glass-capillary tube having an inner diameter of about 0.8 mm and an outer diameter of about 1.0 mm and the second volume is not greater than about 10 µl.

5. A container as defined in claim 1 wherein at least a portion of the reaction portion is transparent.

6. The container of claim 1 wherein the second volume is between about 0.01 µl to about 100 µl.

7. The container of claim 1 wherein the reaction portion comprises a glass capillary tube having a 0.8 mm inner diameter and a 1.0 mm outer diameter.

8. The container of claim 7 wherein the receiving portion is in the shape of a funnel and the capillary tube comprises a closed first end and a flared second end, the flared second end for receiving the funnel shaped portion of the receiving portion.

9. The container of claim 8 wherein the closed first end comprises a flat tip.

10. A container as defined in claim 9 wherein the capillary tube has a length of about 80 mm.

11. The container of claim 1 wherein the reaction portion has a volume to surface ratio of less than 0.25 mm.

12. The container of claim 1 wherein the closed end is formed to optimize optical transmissibility for light having a wavelength of about 400 nm to about 800 nm.

13. A container for holding a fluidic biological sample while undergoing nucleic acid amplification, the container consisting of:
   a receiving portion having a first volume, the receiving portion being adapted to receive the biological sample therein; and
   a reaction portion consisting of a capillary tube that is closed at one end, has an inner diameter in the range from about 0.02 mm to about 0.1 mm, and a capillary tube wall about 0.1 mm thick, said reaction portion being in fluidic communication with the receiving portion such that the biological sample placed in the receiving portion can travel to the reaction portion, the reaction portion having an internal volume not greater than a second volume, the second volume being less than the first volume and not greater than 1 milliliter, said reaction portion comprised of material having a thermal conductivity in the range from about 20 to about 35 in accordance with the formula:

$$\left(\frac{\text{cal cm}}{\text{cm}^2\text{s degree C.}}\right) \times 10^4.$$

14. A container for rapidly heating and cooling a fluidic biological sample contained therein, the container consisting of:
   a receiving portion defining a first internal volume, the receiving portion being adapted to receive the biological sample therein;
   a reaction portion, consisting of a thin walled capillary tube that is closed at one end, and has an inner diameter selected from the range of about 0.25 mm to about 1.0 mm, wherein the closed end is formed for optical transmissibility through the closed end, and the capillary tube wall is about 0.1 mm thick or less, said reaction portion being in fluidic communication with the receiving portion such that the biological sample placed in the receiving portion can travel to the reaction portion, the reaction portion having an internal volume not greater than a second volume, the second volume being less than the first volume and not greater than 100 μl.

15. The container of claim 14 wherein the receiving portion is in the shape of a funnel structure.

16. The container of claim 14 wherein the reaction portion comprises a glass capillary tube having a 0.8 mm inner diameter and a 1.0 mm outer diameter.

17. The container of claim 14 wherein the closed end comprises a flat tip.

* * * * *

SEQUENCE LISTING

<160> NUMBER OF SEQ ID NOS: 6

<210> SEQ ID NO 1
<211> LENGTH: 20
<212> TYPE: DNA
<213> ORGANISM: Hepatitis B virus

<400> SEQUENCE: 1
cgtggtggac ttctctcaat                                          20

<210> SEQ ID NO 2
<211> LENGTH: 20
<212> TYPE: DNA
<213> ORGANISM: Hepatitis B virus

<400> SEQUENCE: 2
agaagatgag gcatagcagc                                          20

<210> SEQ ID NO 3
<211> LENGTH: 35
<212> TYPE: DNA
<213> ORGANISM: Homo sapiens

-continued

```
<400> SEQUENCE: 3
caaacagaca ccatggtgca cctgactcct gagga                              35

<210> SEQ ID NO 4
<211> LENGTH: 30
<212> TYPE: DNA
<213> ORGANISM: Homo sapiens

<400> SEQUENCE: 4
aagtctgccg ttactgccct gtggggcaag                                    30

<210> SEQ ID NO 5
<211> LENGTH: 22
<212> TYPE: DNA
<213> ORGANISM: Homo sapiens

<400> SEQUENCE: 5
ggttggccaa tctactccca gg                                            22

<210> SEQ ID NO 6
<211> LENGTH: 20
<212> TYPE: DNA
<213> ORGANISM: Homo sapiens

<400> SEQUENCE: 6
gctcactcag tgtggcaaag                                               20
```